(12) United States Patent
Zucherman et al.

(10) Patent No.: US 8,568,460 B2
(45) Date of Patent: Oct. 29, 2013

(54) SPINE DISTRACTION IMPLANT AND METHOD

(75) Inventors: James F. Zucherman, San Francisco, CA (US); Ken Y. Hsu, San Francisco, CA (US); T. Wade Fallin, Hyde Park, UT (US); Henry A. Klyce, Piedmont, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 541 days.

(21) Appl. No.: 11/790,904

(22) Filed: Apr. 27, 2007

(65) Prior Publication Data

US 2007/0203501 A1 Aug. 30, 2007

Related U.S. Application Data

(60) Continuation of application No. 10/732,589, filed on Dec. 10, 2003, which is a division of application No. 09/842,756, filed on Apr. 26, 2001, now Pat. No. 6,699,247, which is a continuation of application No. 09/474,038, filed on Dec. 28, 1999, now Pat. No. 6,332,882, which is a continuation of application No. 09/175,645, filed on Oct. 20, 1998, now Pat. No. 6,068,630, which is a continuation-in-part of application No. 08/958,281, filed on Oct. 27, 1997, now Pat. No. 5,860,977, which is a continuation-in-part of application No. 08/778,093, filed on Jan. 2, 1997, now Pat. No. 5,836,948.

(51) Int. Cl.
*A61B 17/70* (2006.01)

(52) U.S. Cl.
USPC ............................ 606/279; 606/248; 606/249

(58) Field of Classification Search
USPC .......... 606/61, 248, 249, 86 A, 99, 139, 246, 606/247, 262, 263, 279, 913; 623/17.11–17.16
See application file for complete search history.

(56) References Cited

U.S. PATENT DOCUMENTS

| | | | | |
|---|---|---|---|---|
| 2,677,369 A | * | 5/1954 | Knowles | 606/249 |
| 3,123,077 A | * | 3/1964 | Alcamo | 606/228 |
| 3,397,699 A | | 8/1968 | Kohl | |
| 3,620,216 A | * | 11/1971 | Szymanski | 604/60 |
| 3,648,691 A | * | 3/1972 | Lumb et al. | 606/279 |
| 4,011,602 A | | 3/1977 | Rybicki et al. | |
| 4,257,409 A | | 3/1981 | Bacal et al. | |
| 4,327,736 A | | 5/1982 | Inoue | |

(Continued)

FOREIGN PATENT DOCUMENTS

| DE | 2821678 A1 | 11/1979 |
|---|---|---|
| DE | 3113142 A1 | 1/1982 |

(Continued)

OTHER PUBLICATIONS

Howorth M.B., "Evolution of Spinal Fusion", Feb. 1943, v. 117(2), 278-289.*

(Continued)

*Primary Examiner* — Kevin T Truong
*Assistant Examiner* — Christian Sevilla

(57) ABSTRACT

A spine distraction implant alleviates pain associated with spinal stenosis and facet arthropathy by expanding the volume in the spine canal and/or neural foramen. The implant provides a spinal extension stop while allowing freedom of spinal flexion.

13 Claims, 65 Drawing Sheets

(56) References Cited

U.S. PATENT DOCUMENTS

| | | | |
|---|---|---|---|
| 4,449,532 A * | 5/1984 | Storz | 606/191 |
| 4,554,914 A | 11/1985 | Kapp et al. | |
| 4,557,259 A * | 12/1985 | Wu | 606/103 |
| 4,573,454 A | 3/1986 | Hoffman | |
| 4,604,995 A | 8/1986 | Stephens et al. | |
| 4,686,970 A | 8/1987 | Dove et al. | |
| 4,721,103 A | 1/1988 | Freedland | |
| 4,827,918 A | 5/1989 | Olerud | |
| 4,862,891 A * | 9/1989 | Smith | 606/191 |
| 5,011,484 A * | 4/1991 | Breard | 606/249 |
| 5,047,055 A | 9/1991 | Bao et al. | |
| 5,074,318 A * | 12/1991 | Campbell et al. | 128/899 |
| 5,092,866 A | 3/1992 | Breard et al. | |
| 5,158,543 A * | 10/1992 | Lazarus | 604/164.1 |
| 5,201,734 A | 4/1993 | Cozad et al. | |
| 5,306,275 A | 4/1994 | Bryan | |
| 5,316,422 A | 5/1994 | Coffman | |
| 5,360,430 A | 11/1994 | Lin | |
| 5,366,455 A | 11/1994 | Dove | |
| 5,368,595 A * | 11/1994 | Lewis | 606/151 |
| 5,415,661 A | 5/1995 | Holmes | |
| 5,433,739 A * | 7/1995 | Sluijter et al. | 607/99 |
| 5,437,672 A | 8/1995 | Alleyne | |
| 5,454,812 A | 10/1995 | Lin | |
| 5,472,426 A * | 12/1995 | Bonati et al. | 604/164.1 |
| 5,496,318 A * | 3/1996 | Howland et al. | 606/249 |
| 5,562,684 A * | 10/1996 | Kammerer | 606/139 |
| 5,609,634 A * | 3/1997 | Voydeville | 623/13.11 |
| 5,628,756 A | 5/1997 | Barker, Jr. et al. | |
| 5,645,599 A * | 7/1997 | Samani | 623/17.16 |
| 5,665,096 A * | 9/1997 | Yoon | 606/139 |
| 5,674,295 A | 10/1997 | Ray et al. | |
| 5,676,702 A | 10/1997 | Ratron | |
| 5,690,649 A | 11/1997 | Li | |
| 5,702,452 A | 12/1997 | Argenson et al. | |
| 5,725,582 A * | 3/1998 | Bevan et al. | 606/61 |
| 5,755,797 A * | 5/1998 | Baumgartner | 623/17.16 |
| 5,792,044 A * | 8/1998 | Foley et al. | 600/114 |
| 5,792,085 A * | 8/1998 | Walters | 602/19 |
| 5,797,909 A * | 8/1998 | Michelson | 606/914 |
| 5,810,815 A | 9/1998 | Morales | |
| 5,836,948 A | 11/1998 | Zucherman et al. | |
| 5,860,977 A | 1/1999 | Zucherman et al. | |
| 5,928,242 A * | 7/1999 | Kuslich et al. | 606/96 |
| 5,976,186 A | 11/1999 | Bao et al. | |
| 6,022,376 A | 2/2000 | Assell et al. | |
| 6,048,342 A | 4/2000 | Zucherman et al. | |
| 6,068,630 A | 5/2000 | Zucherman et al. | |
| 6,074,390 A | 6/2000 | Zucherman et al. | |
| 6,132,464 A | 10/2000 | Martin | |
| 6,214,037 B1 | 4/2001 | Mitchell et al. | |
| 6,293,949 B1 | 9/2001 | Justis et al. | |
| 6,352,537 B1 | 3/2002 | Strnad | |
| 6,364,883 B1 | 4/2002 | Santilli | |
| 6,402,750 B1 | 6/2002 | Atkinson et al. | |
| 6,419,703 B1 | 7/2002 | Fallin et al. | |
| 6,440,169 B1 | 8/2002 | Elberg et al. | |
| 6,451,019 B1 | 9/2002 | Zucherman et al. | |
| 6,500,178 B2 | 12/2002 | Zucherman et al. | |
| 6,514,256 B2 | 2/2003 | Zucherman et al. | |
| 6,582,433 B2 | 6/2003 | Yun | |
| 6,626,944 B1 | 9/2003 | Taylor | |
| 6,645,207 B2 | 11/2003 | Dixon et al. | |
| 6,669,729 B2 | 12/2003 | Chin | |
| 6,695,842 B2 | 2/2004 | Zucherman et al. | |
| 6,699,246 B2 | 3/2004 | Zucherman et al. | |
| 6,709,435 B2 | 3/2004 | Lin | |
| 6,723,126 B1 | 4/2004 | Berry | |
| 6,733,534 B2 | 5/2004 | Sherman | |
| 6,761,720 B1 | 7/2004 | Senegas | |
| 6,835,205 B2 | 12/2004 | Atkinson et al. | |
| 6,902,580 B2 | 6/2005 | Fallin et al. | |
| 6,946,000 B2 | 9/2005 | Senegas et al. | |
| 7,041,136 B2 | 5/2006 | Goble et al. | |
| 7,048,736 B2 | 5/2006 | Robinson et al. | |
| 7,087,083 B2 | 8/2006 | Pasquet et al. | |
| 7,097,654 B1 | 8/2006 | Freedland | |
| 7,101,375 B2 | 9/2006 | Zucherman et al. | |
| 7,163,558 B2 | 1/2007 | Senegas et al. | |
| 7,201,751 B2 | 4/2007 | Zucherman et al. | |
| 7,238,204 B2 | 7/2007 | Le Couedic et al. | |
| 7,306,628 B2 | 12/2007 | Zucherman et al. | |
| 7,335,203 B2 | 2/2008 | Winslow et al. | |
| 7,377,942 B2 | 5/2008 | Berry | |
| 7,442,208 B2 | 10/2008 | Mathieu et al. | |
| 7,445,637 B2 | 11/2008 | Taylor | |
| 7,585,316 B2 * | 9/2009 | Trieu | 606/279 |
| 7,604,652 B2 | 10/2009 | Arnin et al. | |
| 7,658,752 B2 | 2/2010 | Labrom et al. | |
| 7,749,252 B2 | 7/2010 | Zucherman et al. | |
| 7,771,456 B2 | 8/2010 | Hartman et al. | |
| 7,862,615 B2 | 1/2011 | Carli et al. | |
| 7,901,430 B2 | 3/2011 | Matsuura et al. | |
| 2001/0016743 A1 | 8/2001 | Zucherman et al. | |
| 2003/0045940 A1 | 3/2003 | Eberlein et al. | |
| 2003/0065330 A1 | 4/2003 | Zucherman et al. | |
| 2003/0153915 A1 | 8/2003 | Nekozuka et al. | |
| 2004/0097931 A1 | 5/2004 | Mitchell | |
| 2004/0106995 A1 | 6/2004 | LeCoudeic et al. | |
| 2004/0117017 A1 | 6/2004 | Pasquet et al. | |
| 2004/0133280 A1 | 7/2004 | Trieu | |
| 2004/0199255 A1 | 10/2004 | Mathieu et al. | |
| 2005/0010293 A1 | 1/2005 | Zucherman et al. | |
| 2005/0033434 A1 | 2/2005 | Berry | |
| 2005/0049708 A1 | 3/2005 | Atkinson et al. | |
| 2005/0165398 A1 | 7/2005 | Reiley | |
| 2005/0203512 A1 | 9/2005 | Hawkins et al. | |
| 2005/0203624 A1 | 9/2005 | Serhan et al. | |
| 2005/0228391 A1 | 10/2005 | Levy et al. | |
| 2005/0261768 A1 * | 11/2005 | Trieu | 623/17.11 |
| 2005/0267579 A1 | 12/2005 | Reiley et al. | |
| 2005/0288672 A1 | 12/2005 | Ferree | |
| 2006/0004447 A1 | 1/2006 | Mastrorio et al. | |
| 2006/0015181 A1 | 1/2006 | Elberg | |
| 2006/0064165 A1 | 3/2006 | Zucherman et al. | |
| 2006/0084983 A1 | 4/2006 | Kim | |
| 2006/0084985 A1 | 4/2006 | Kim | |
| 2006/0084987 A1 | 4/2006 | Kim | |
| 2006/0084988 A1 | 4/2006 | Kim | |
| 2006/0085069 A1 | 4/2006 | Kim | |
| 2006/0085070 A1 | 4/2006 | Kim | |
| 2006/0085074 A1 | 4/2006 | Raiszadeh | |
| 2006/0089654 A1 | 4/2006 | Lins et al. | |
| 2006/0089719 A1 | 4/2006 | Trieu | |
| 2006/0106381 A1 | 5/2006 | Ferree et al. | |
| 2006/0106397 A1 | 5/2006 | Lins | |
| 2006/0111728 A1 | 5/2006 | Abdou | |
| 2006/0122620 A1 | 6/2006 | Kim | |
| 2006/0129239 A1 | 6/2006 | Kwak | |
| 2006/0136060 A1 | 6/2006 | Taylor | |
| 2006/0149242 A1 | 7/2006 | Kraus et al. | |
| 2006/0182515 A1 | 8/2006 | Panasik et al. | |
| 2006/0184247 A1 | 8/2006 | Edidin et al. | |
| 2006/0184248 A1 | 8/2006 | Edidin et al. | |
| 2006/0195102 A1 | 8/2006 | Malandain | |
| 2006/0217726 A1 | 9/2006 | Maxy et al. | |
| 2006/0224159 A1 | 10/2006 | Anderson | |
| 2006/0235387 A1 | 10/2006 | Peterman | |
| 2006/0235532 A1 | 10/2006 | Meunier et al. | |
| 2006/0241613 A1 | 10/2006 | Bruneau et al. | |
| 2006/0241757 A1 | 10/2006 | Anderson | |
| 2006/0247623 A1 | 11/2006 | Anderson et al. | |
| 2006/0247640 A1 | 11/2006 | Blackwell et al. | |
| 2006/0264938 A1 | 11/2006 | Zucherman et al. | |
| 2006/0271044 A1 | 11/2006 | Petrini et al. | |
| 2006/0271049 A1 | 11/2006 | Zucherman et al. | |
| 2006/0282075 A1 | 12/2006 | Labrom et al. | |
| 2006/0282079 A1 | 12/2006 | Labrom et al. | |
| 2006/0293662 A1 | 12/2006 | Boyer, II et al. | |
| 2006/0293663 A1 | 12/2006 | Walkenhorst et al. | |
| 2007/0005064 A1 | 1/2007 | Anderson et al. | |
| 2007/0010813 A1 | 1/2007 | Zucherman et al. | |
| 2007/0043362 A1 | 2/2007 | Malandain et al. | |
| 2007/0043363 A1 | 2/2007 | Malandain et al. | |

(56) References Cited

U.S. PATENT DOCUMENTS

| | | |
|---|---|---|
| 2007/0100340 A1 | 5/2007 | Lange et al. |
| 2007/0123861 A1 | 5/2007 | Dewey et al. |
| 2007/0162000 A1 | 7/2007 | Perkins |
| 2007/0167945 A1 | 7/2007 | Lange et al. |
| 2007/0173822 A1 | 7/2007 | Bruneau et al. |
| 2007/0173823 A1 | 7/2007 | Dewey et al. |
| 2007/0191833 A1 | 8/2007 | Bruneau et al. |
| 2007/0191834 A1 | 8/2007 | Bruneau et al. |
| 2007/0191837 A1 | 8/2007 | Trieu |
| 2007/0198091 A1 | 8/2007 | Boyer et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233081 A1 | 10/2007 | Pasquet et al. |
| 2007/0233089 A1 | 10/2007 | DiPoto et al. |
| 2007/0250060 A1 | 10/2007 | Anderson et al. |
| 2007/0270823 A1 | 11/2007 | Trieu et al. |
| 2007/0270824 A1 | 11/2007 | Lim et al. |
| 2007/0270825 A1 | 11/2007 | Carls et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0270874 A1 | 11/2007 | Anderson |
| 2007/0272259 A1 | 11/2007 | Allard et al. |
| 2007/0276368 A1 | 11/2007 | Trieu et al. |
| 2007/0276496 A1 | 11/2007 | Lange et al. |
| 2007/0276497 A1 | 11/2007 | Anderson |
| 2008/0021460 A1 | 1/2008 | Bruneau et al. |
| 2008/0097446 A1 | 4/2008 | Reiley et al. |
| 2008/0114357 A1 | 5/2008 | Allard et al. |
| 2008/0114358 A1 | 5/2008 | Anderson et al. |
| 2008/0114456 A1 | 5/2008 | Dewey et al. |
| 2008/0147190 A1 | 6/2008 | Dewey et al. |
| 2008/0161818 A1 | 7/2008 | Kloss et al. |
| 2008/0167685 A1 | 7/2008 | Allard et al. |
| 2008/0195152 A1 | 8/2008 | Altarac et al. |
| 2008/0215094 A1 | 9/2008 | Taylor |
| 2008/0271360 A1 | 11/2008 | Barfield |
| 2008/0281361 A1 | 11/2008 | Vittur et al. |
| 2009/0062915 A1 | 3/2009 | Kohm et al. |
| 2009/0105773 A1 | 4/2009 | Lange et al. |
| 2009/0240283 A1 | 9/2009 | Carls et al. |
| 2010/0121379 A1 | 5/2010 | Edmond |
| 2010/0204732 A1 | 8/2010 | Aschmann et al. |
| 2010/0211101 A1 | 8/2010 | Blackwell et al. |

FOREIGN PATENT DOCUMENTS

| | | |
|---|---|---|
| EP | 0322334 B1 | 2/1992 |
| EP | 1138268 A1 | 10/2001 |
| EP | 1330987 A1 | 7/2003 |
| EP | 1854433 A1 | 11/2007 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2722980 A1 | 2/1996 |
| FR | 2724554 A1 | 3/1996 |
| FR | 2725892 A1 | 4/1996 |
| FR | 2730156 A1 | 8/1996 |
| FR | 2775183 A1 | 8/1999 |
| FR | 2799948 A1 | 4/2001 |
| FR | 2816197 A1 | 5/2002 |
| JP | 02-224660 | 9/1990 |
| JP | 09-075381 | 3/1997 |
| JP | 2003079649 | 3/2003 |
| SU | 988281 | 1/1983 |
| SU | 1484348 A1 | 6/1989 |
| WO | WO 94/26192 | 11/1994 |
| WO | WO 94/26195 | 11/1994 |
| WO | WO 98/20939 | 5/1998 |
| WO | WO 2004/047691 A1 | 6/2004 |
| WO | 2004/084743 A1 | 10/2004 |
| WO | WO 2005/009300 A1 | 2/2005 |
| WO | WO 2005/044118 A1 | 5/2005 |
| WO | WO 2005/110258 A1 | 11/2005 |
| WO | 2006/064356 A1 | 6/2006 |
| WO | 2007/034516 A1 | 3/2007 |

OTHER PUBLICATIONS

"Dispositivo Intervertebrale Ammortizzante DIAM," date unknown, p. 1.

"Tecnica Operatoria Per Il Posizionamento Della Protesi DIAM," date unknown, pp. 1-3.

"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.

Benzel et al., "Posterior Cervical Interspinous Compression Wiring and Fusion for Mid to Low Cervical Spinal Injuries," J. Neurosurg., Jun. 1989, ppp. 893-899, vol. 70.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," SPINE, 2005, pp. S73-S78, vol. 30, No. 16S.

Cousin Biotech, "Analysis of Clinical Experience with a Posterior Shock-Absorbing Implant," date unknown, pp. 2-9.

Cousin Biotech, Dispositif Intervertébral Amortissant, Jun. 1998, pp. 1-4.

Cousin Biotech, Technique Operatoire de la Prothese DIAM, date unknown, Annexe 1, pp. 1-8.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," SPINE, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," SPINE, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

(56) References Cited

OTHER PUBLICATIONS

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.
McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.
Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.
Müller, "Restauration Dynamique de la Stabilité Rachidienne," Tiré de la Sulzer Technical Review, Jan. 1999, Sulzer Management Ltd, Winterthur, Switzerland.
Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.
Petrini et al., "Analisi Di Un'Esperienza Clinica Con Un Implanto Posteriore Ammortizzante," S.O.T.I.M.I. Società di Ortopedia e Traumatologia dell'Italia Meridionale e Insulare 90° Congresso, Jun. 21-23, 2001, Paestum.
Petrini et al., "Stabilizzazione Elastica," Patologia Degenerativa del Rachide Lombare, Oct. 5-6, 2001, Rimini.
Porter, "Spinal Stenosis and Neurogenic Claudication," SPINE, Sep. 1, 1996, pp. 2046-2052, vol. 21, No. 17.
Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.
Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.
Richards et al., "The Treatment Mechanism of an Interspinous Process Implant for Lumbar Neurogenic Intermittent Claudication," SPINE, 2005, pp. 744-749, vol. 30, No. 7.
Scarfò, "Instability/Stenosis: Holistic Approach for Less Invasive Surgery," date unknown, University of Siena, Siena, Italy.
Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.
Schlegel et al., "The Role of Distraction in Improving the Space Available in the Lumbar Stenotic Canal and Foramen," SPINE, 1994, pp. 2041-2047, vol. 19, No. 18.
Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.
Senegas et al., "Stabilisation Lombaire Souple," Instabilité Vertébrales Lombaires, Gastambide, ed., 1995, pp. 122-132, Expansion Scientifique Française, Paris, France.
Senegas, "La Ligamentoplastie Inter Vertébrale Lombaire, Alternative a L'Arthrodese," La Revue de Medécine Orthopédique, Jun. 1990, pp. 33-35, No. 20.
Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.
Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.
Senegas, "Rencontre," Maîtrise Orthopédique, May 1995, pp. 1-3, No. 44.
Serhan, "Spinal Implants: Past, Present, and Future," 19th International IEEE/EMBS Conference, Oct. 30-Nov. 2, 1997, pp. 2636-2639, Chicago, Illinois.
Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.
Sulzer Innotec, "DIAM—Modified CAD Geometry and Meshing," date unknown.
Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.
Taylor et al., "Surgical Requirement for the Posterior Control of the Rotational Centers," date unknown.
Taylor et al., "Technical and Anatomical Considerations for the Placement of a Posterior Interspinous Stabilizer," 2004, pp. 1-10, Medtronic Sofamor Danek USA, Inc., Memphis, Tennessee.
Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.
Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.
Taylor, "Posterior Dynamic Stabilization using the DIAM (Device for Intervertebral Assisted Motion)," date unknown, pp. 1-5.
Taylor, "Présentation à un an d'un dispositif amortissant d'assistance discale," 5èmes journées Avances & Controverses en pathologie rachidienne, Oct. 1-2, 1998, Faculté Libre de Medecine de Lille.
Tsuji et al., "Ceramic Interspinous Block (CISB) Assisted Anterior Interbody Fusion," J. Spinal Disorders, 1990, pp. 77-86, vol. 3, No. 1.
Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.
Voydeville et al., "Experimental Lumbar Instability and Artificial Ligament," Eur. J. Orthop. Surg. Traumatol., Jul. 15, 2000, pp. 167-176, vol. 10.
Voydeville et al., "Lumbar Instability Treated by Intervertebral Ligamentoplasty with Smooth Wedges," Orthopédie Traumatologie, 1992, pp. 259-264, vol. 2, No. 4.
Waldemar Link, "Spinal Surgery: Instrumentation and Implants for Spinal Surgery," 1981, Link America Inc., New Jersey.
Wiltse et al., "The Treatment of Spinal Stenosis," Clinical Orthopaedics and Related Research, Urist, ed., Mar.-Apr. 1976, pp. 83-91, No. 115.
Wisneski et al., "Decompressive Surgery for Lumbar Spinal Stenosis," Seminars in Spine Surgery, Wiesel, ed., Jun. 1994, pp. 116-123, vol. 6, No. 2.
Zucherman et al., "Clinical Efficacy of Spinal Instrumentation in Lumbar Degenerative Disc Disease," SPINE, Jul. 1992, pp. 834-837, vol. 17, No. 7.
Bellini et al., "Biomechanics of the Lumbar Spine After Dynamic Stabilization," J. Spinal Discord Tech., 2006, vol. 00, No. 00, pp. 1-7.
Buric et al., "DIAM Device for Low Back Pain in Degenerative Disc Disease 24 Months Follow-up," Advances in Minimally Invasive Surgery and Therapy for Spine and Nerves, Alexandre et al., eds., 2011, pp. 177-182, Spinger-Verlat/Wien.
Kramer et al., "Intervetertebral Disk Diseases: Causes, Diagnosis, Treatment and Prophylaxis," pp. 244-249, Medical, 1990.
Phillips et al., "Biomechanics of Posterior Dynamic Stabiling Device (DIAM) After Facetectomy and Disectomy," The Spine Journal, 2006, vol. 6, pp. 714-722.
Taylor et al., "Device for Intervertebral Assisted Motion: Technique and Intial Results," 22 Neurosurg. Focus, Jan. 2007, vol. 22, No. 1, pp. 1-6.
Wilke et al., "Biomedical Effect of Different Lumbar Interspinous Implants on Flexibilty and Intradiscal Pressure," Eur Spine J., Vo. 17, published online Jun. 27, 2008, pp. 1049-1056.
Zdeblick et al., "Two-Point Fixation of the Lumbar Spine Differential Stability in Rotation," Spine, 1991, pp. S298-S301, vol. 16, No. 6, Supplement.
Zhao et al., "Efficacy of the Dynamic Interspinous Assisted Motion System in Clinical Treatment of Degenerative Lumbar Disease," Chin. Med. J., 2010, vol. 123, No. 21, pp. 2974-2977.
European Search Report for EP07018876.8 the counterpart application mailed on Jan. 14, 2013.

* cited by examiner

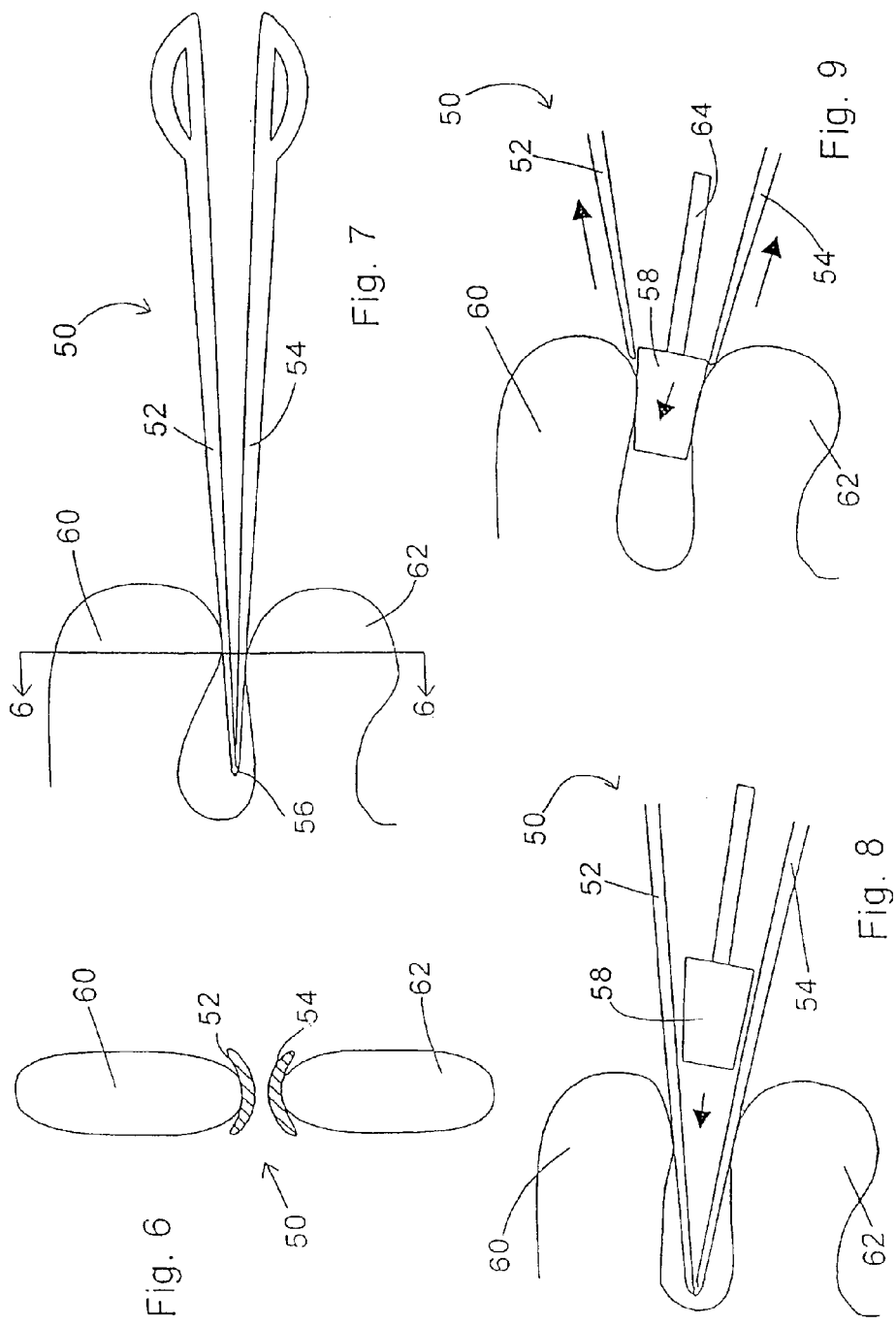

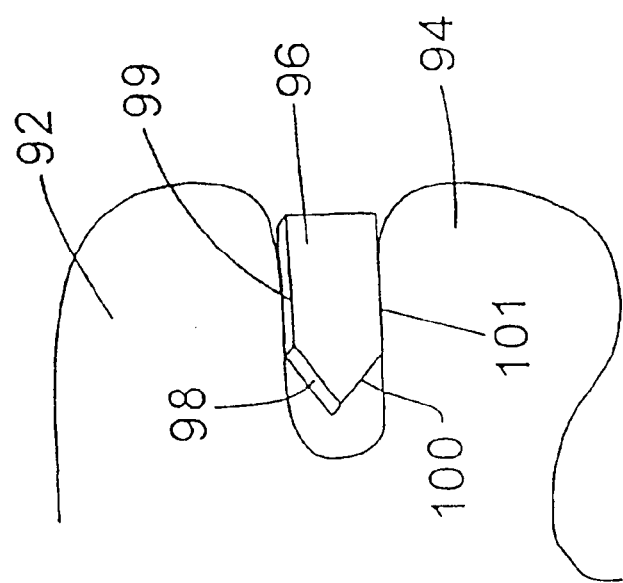
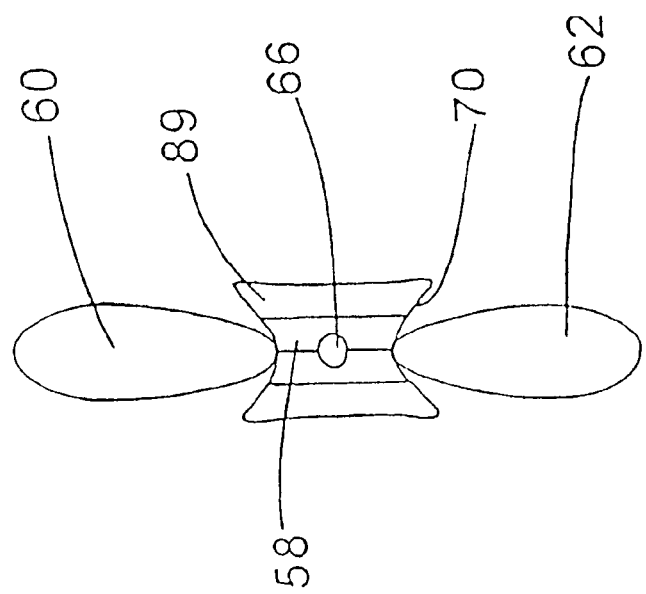

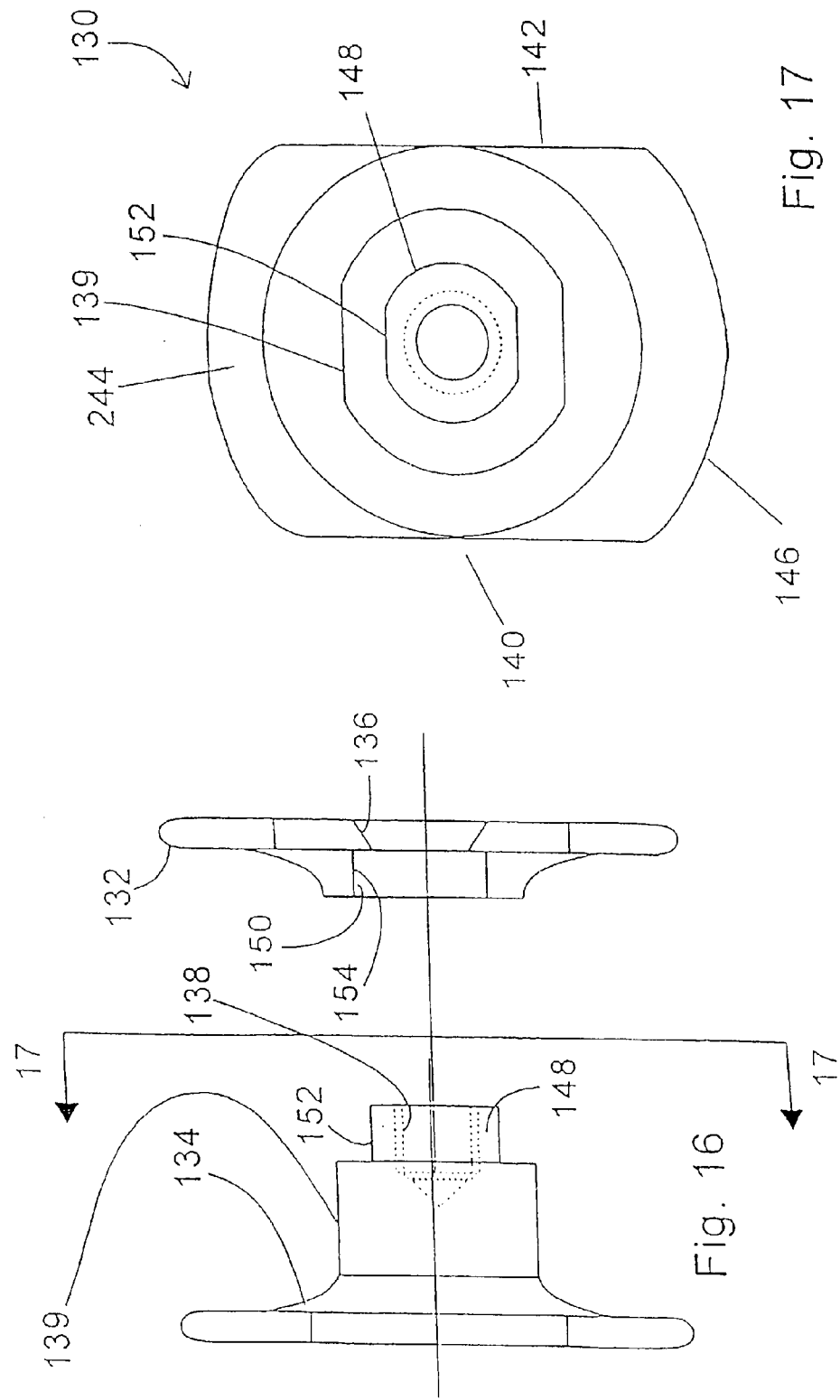

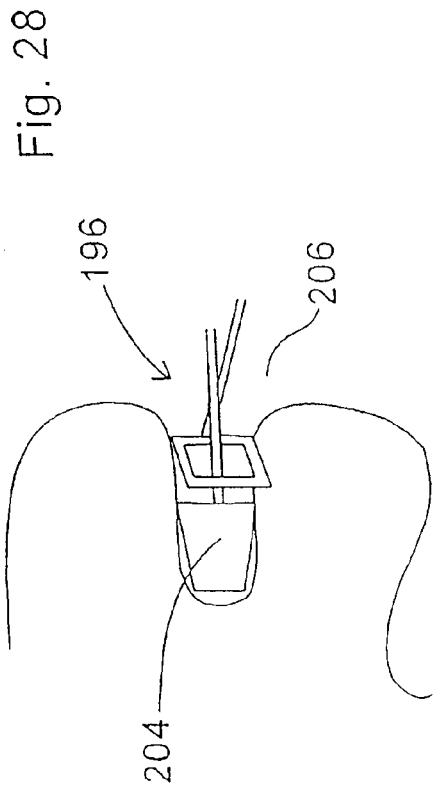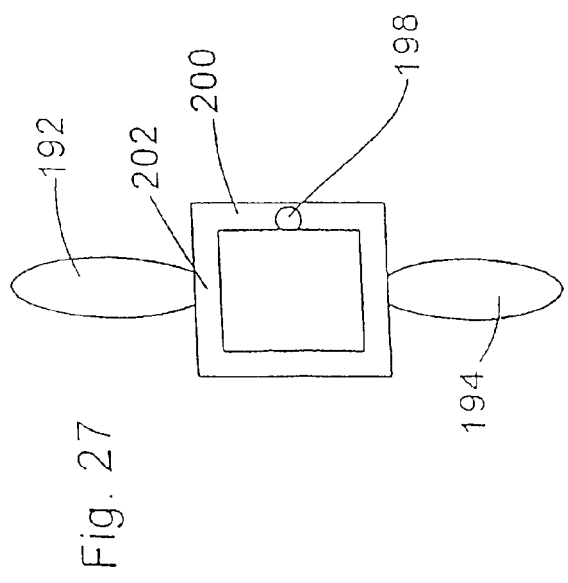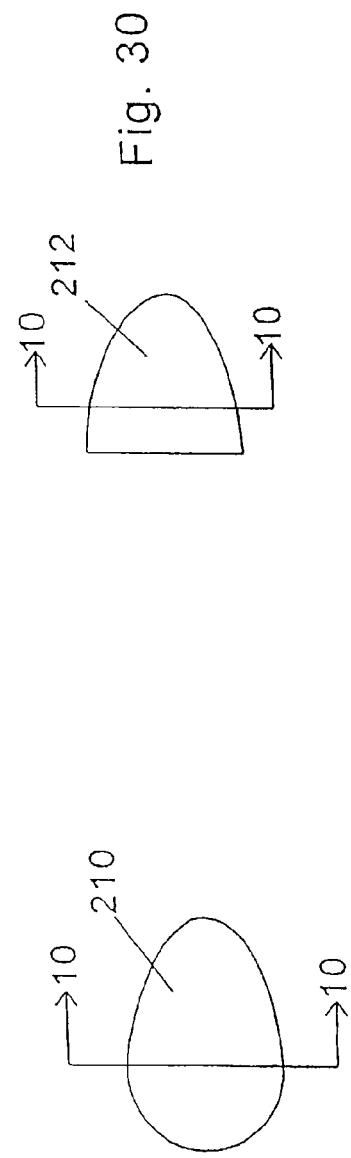

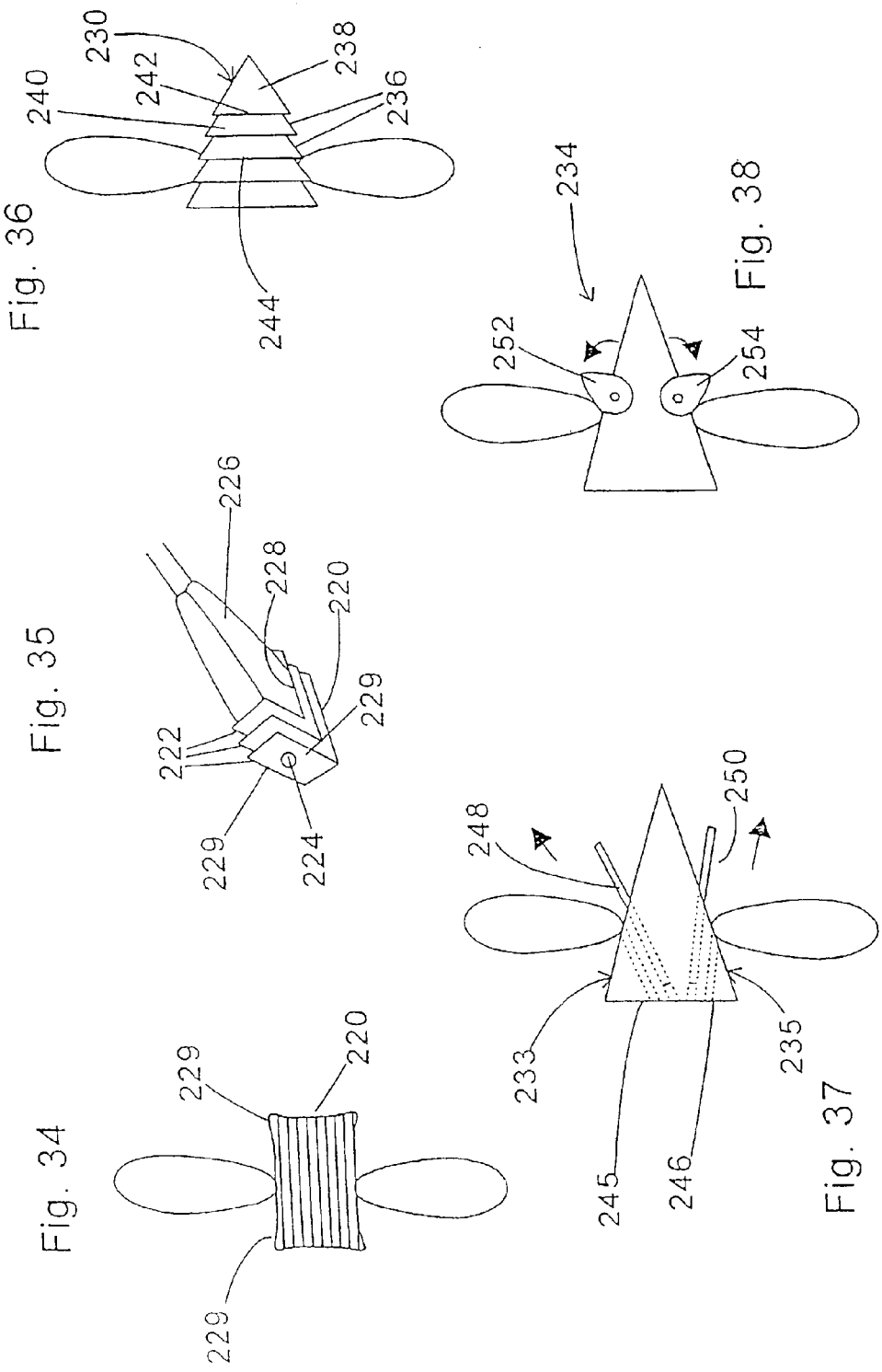

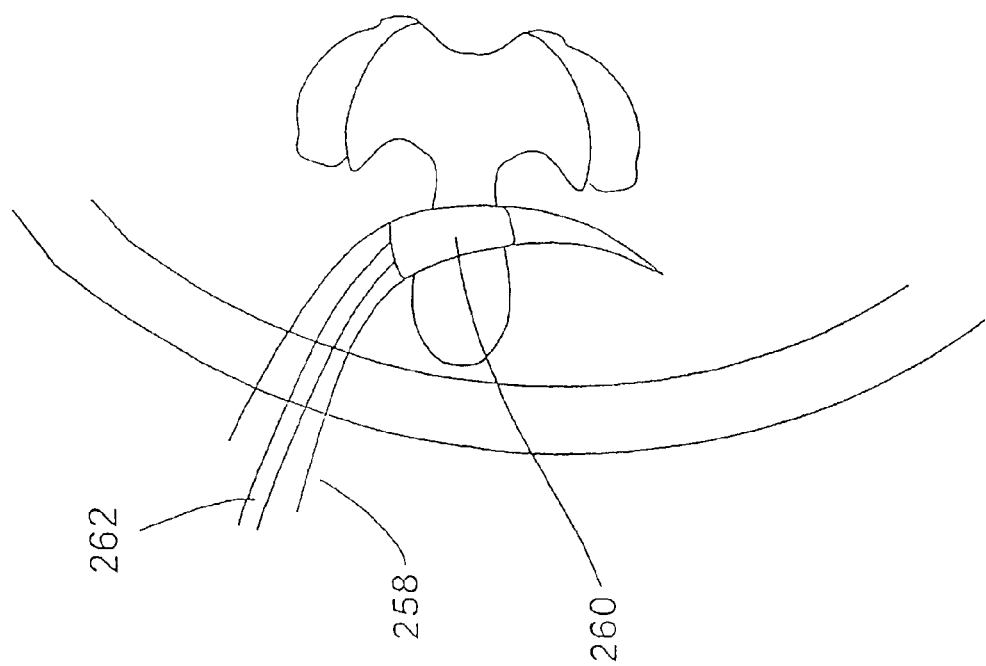

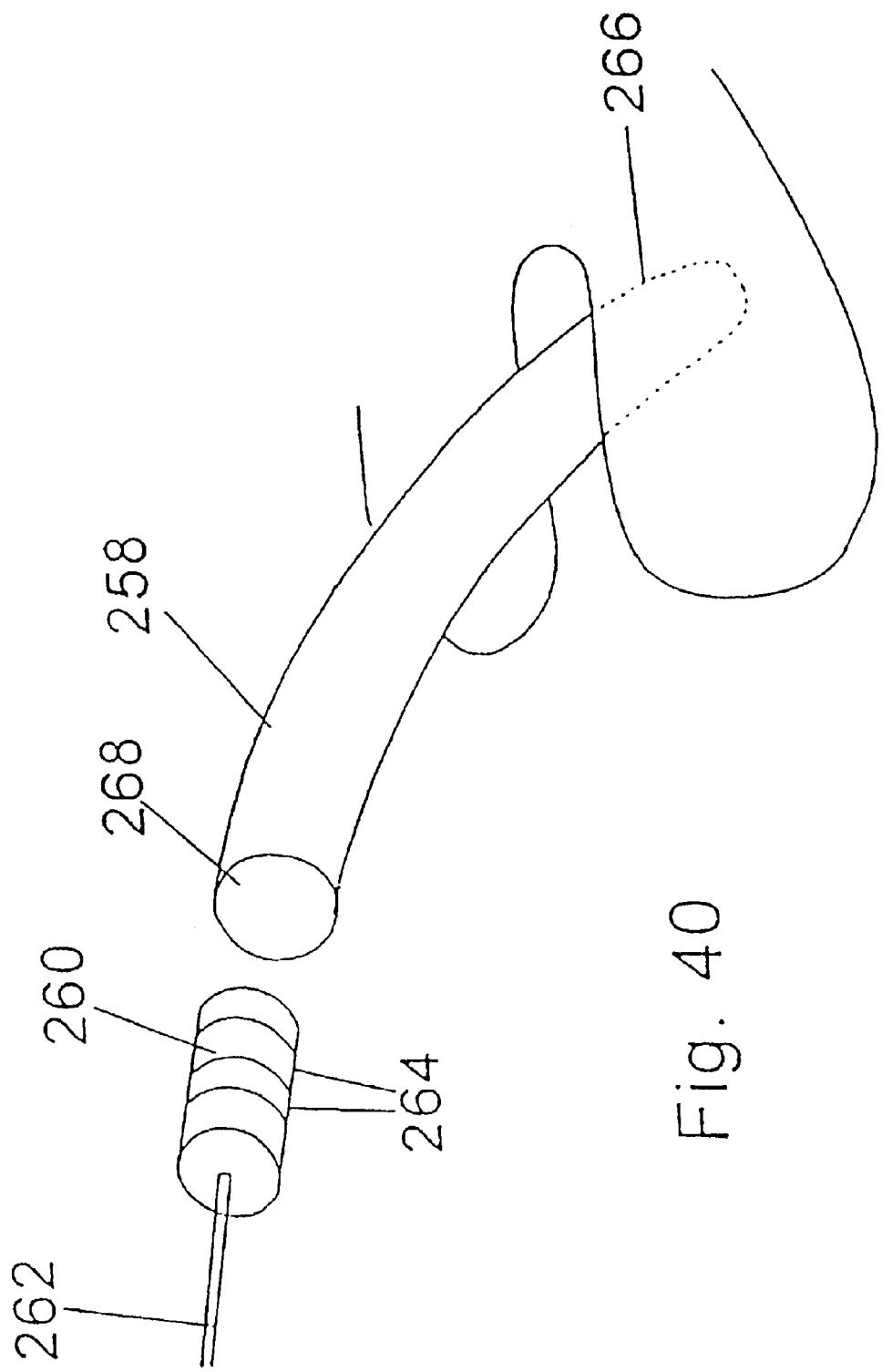

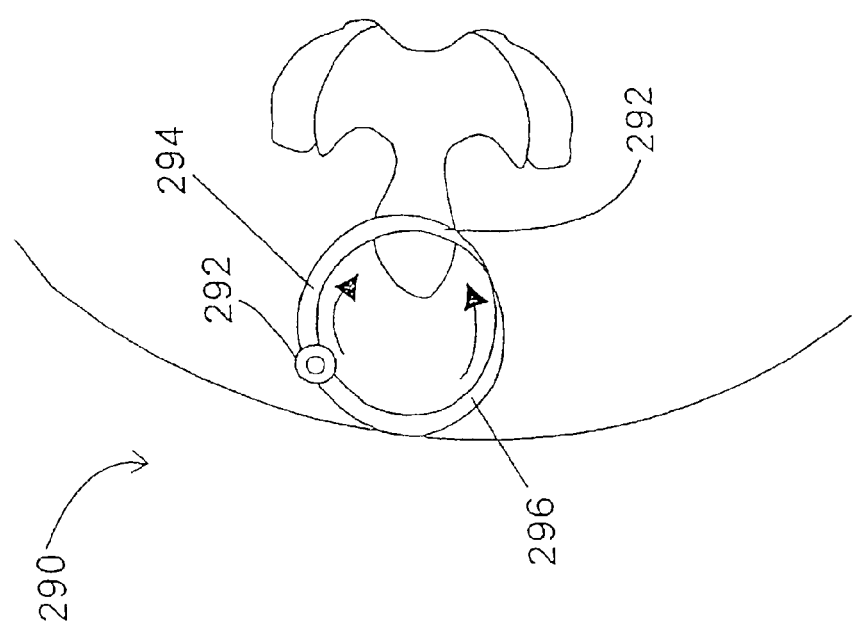

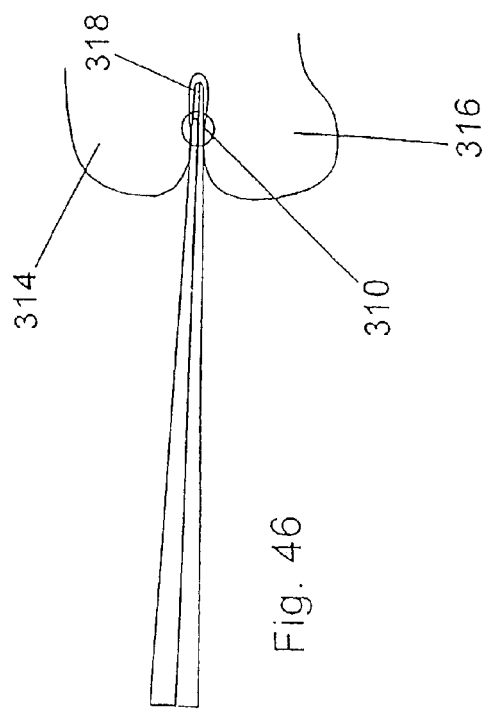
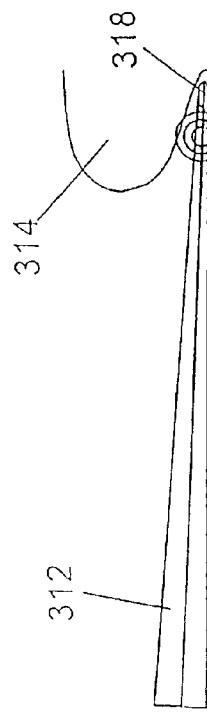
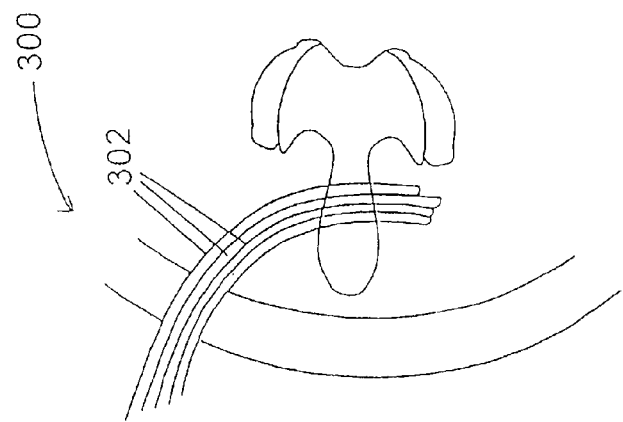
Fig. 47
Fig. 46
Fig. 45

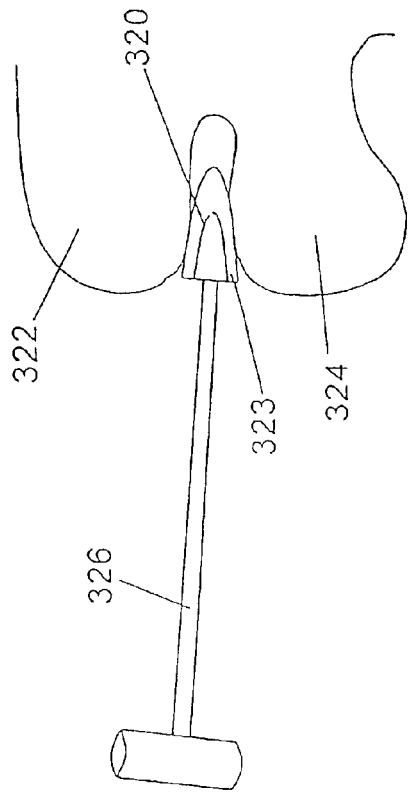
Fig. 48
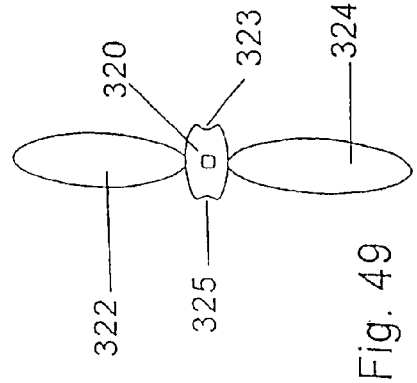
Fig. 49
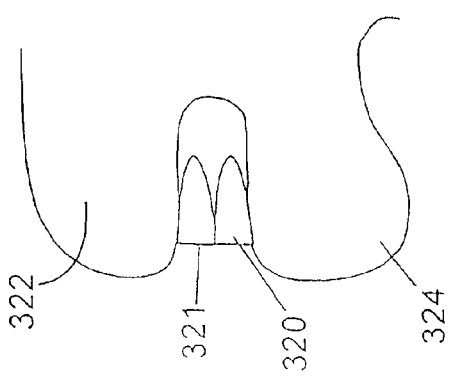
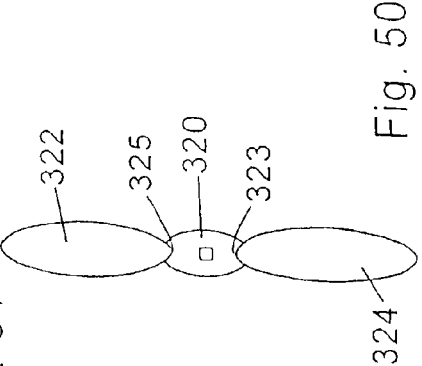
Fig. 51
Fig. 50

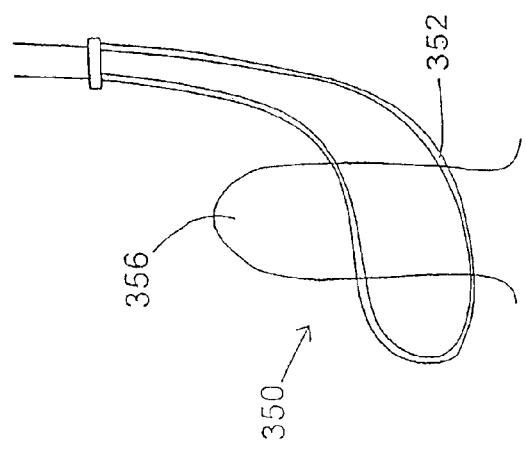
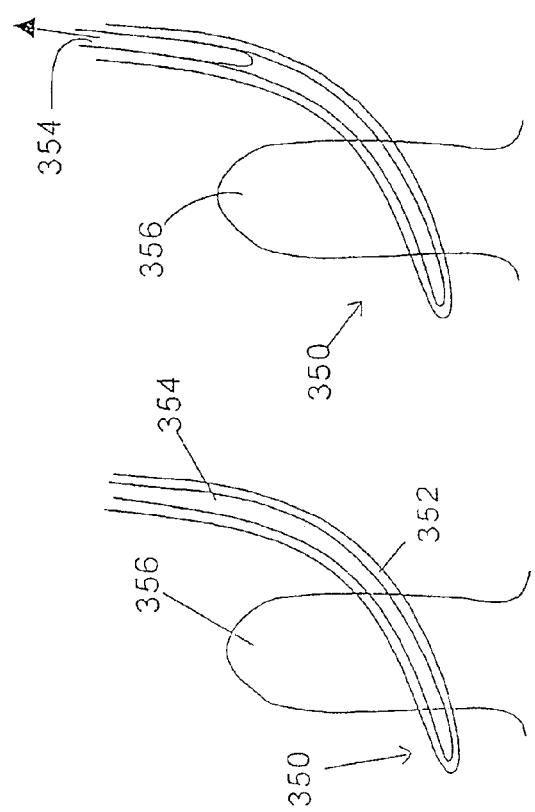
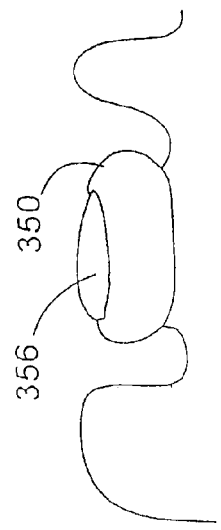
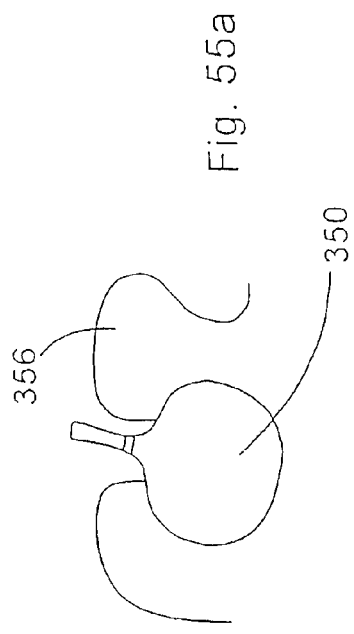

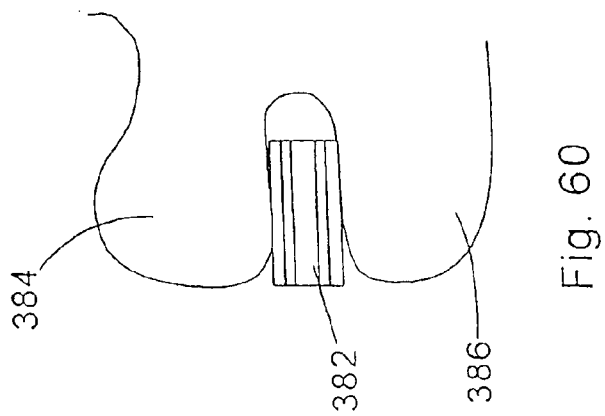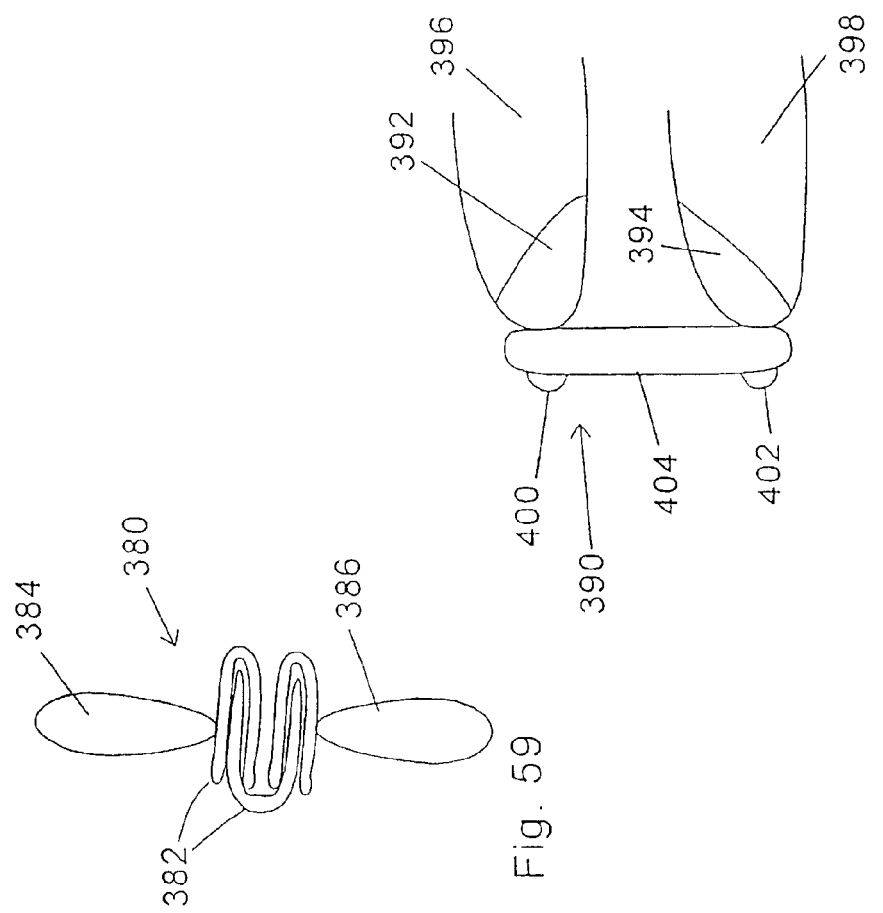

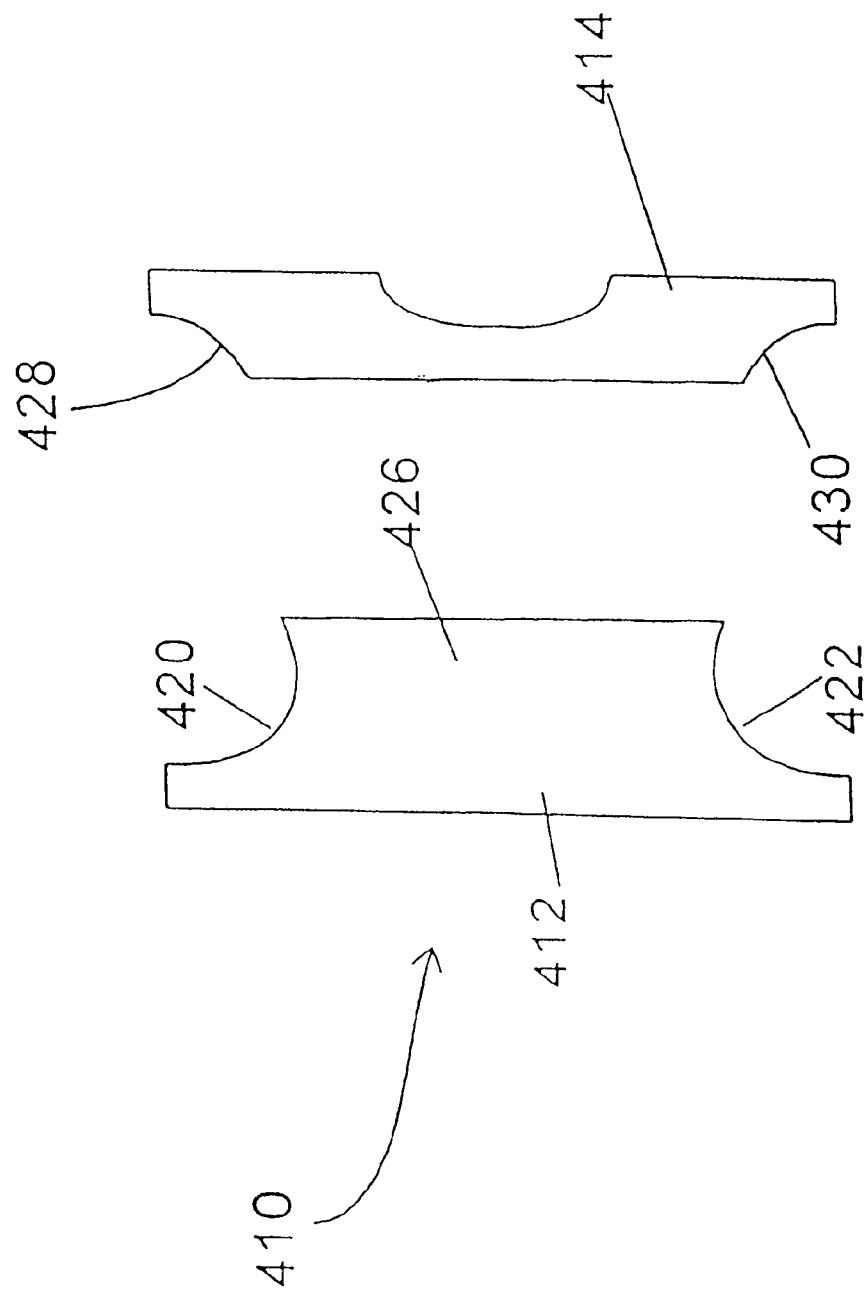

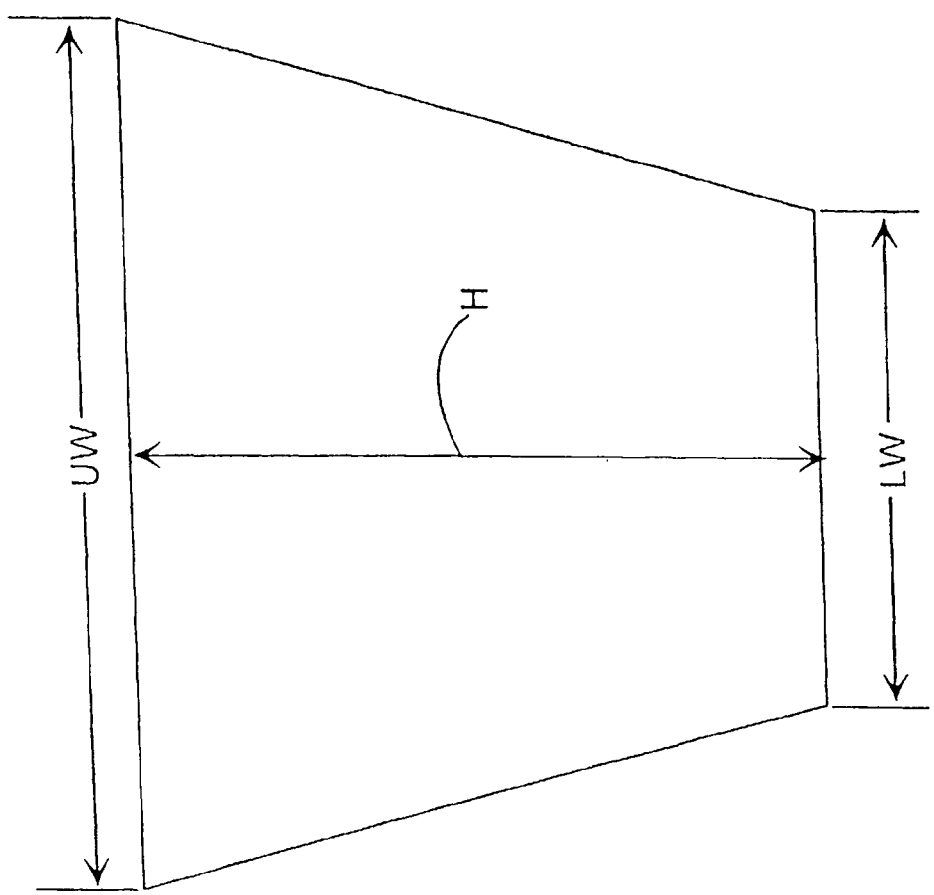

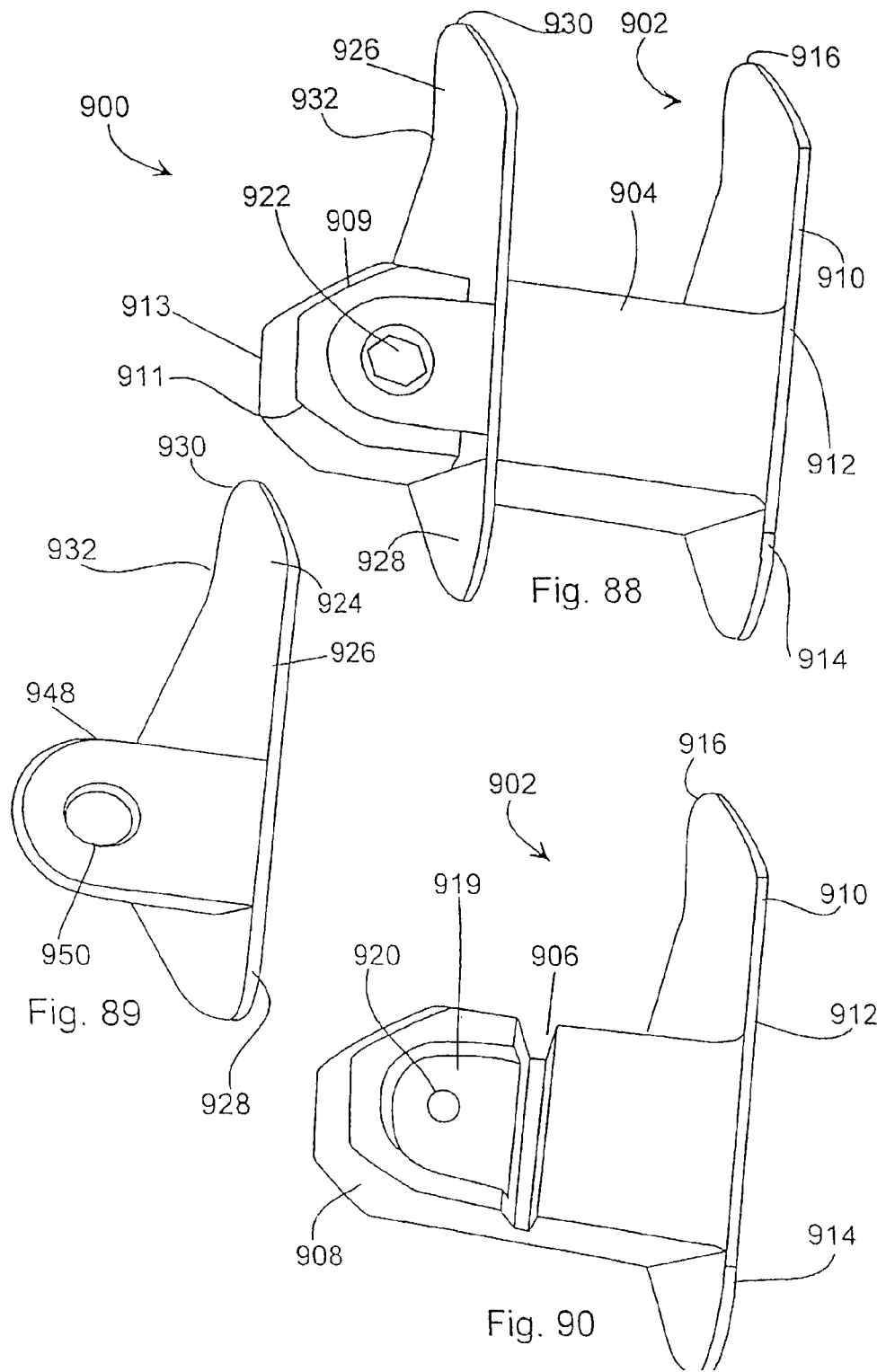

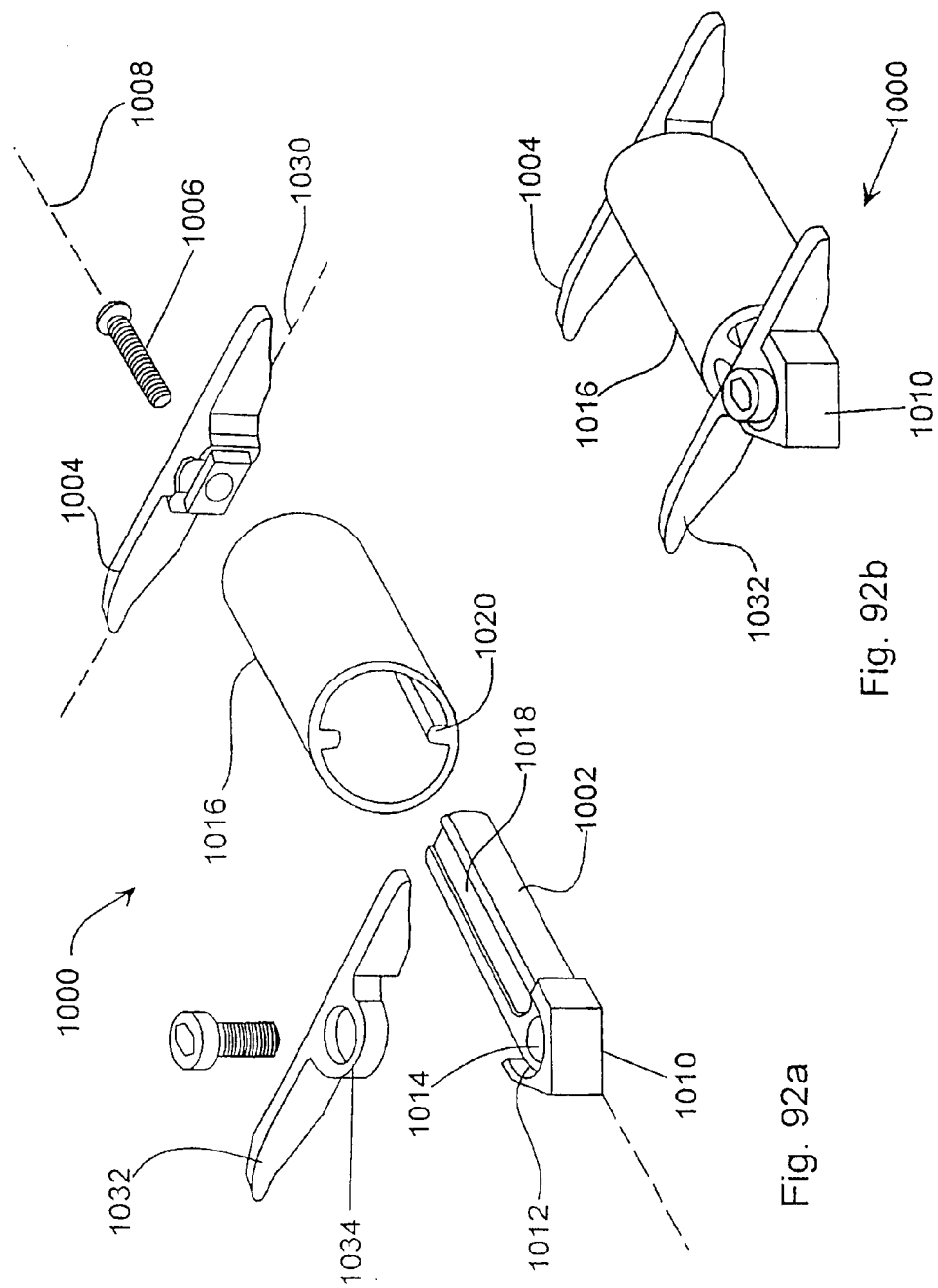

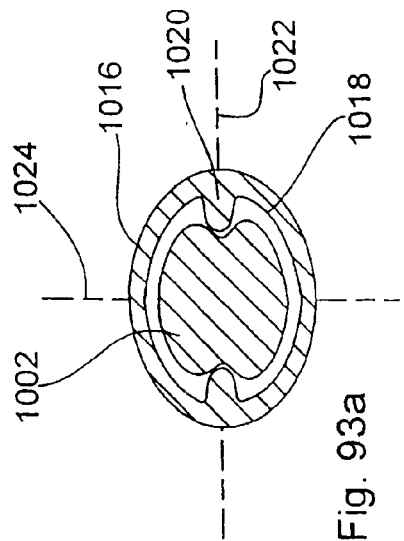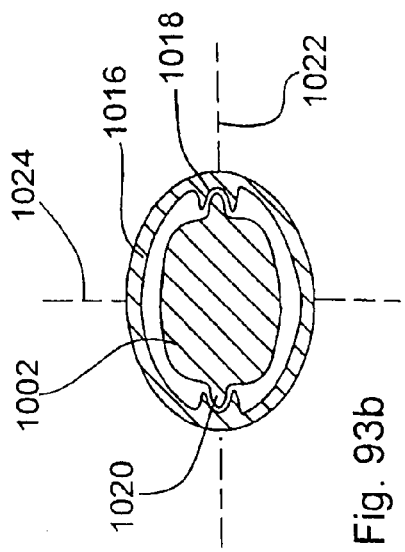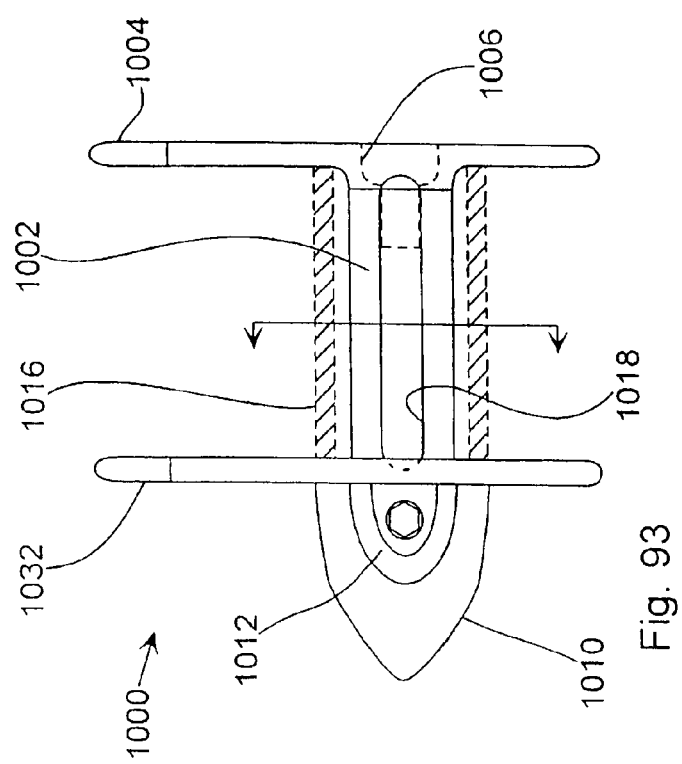

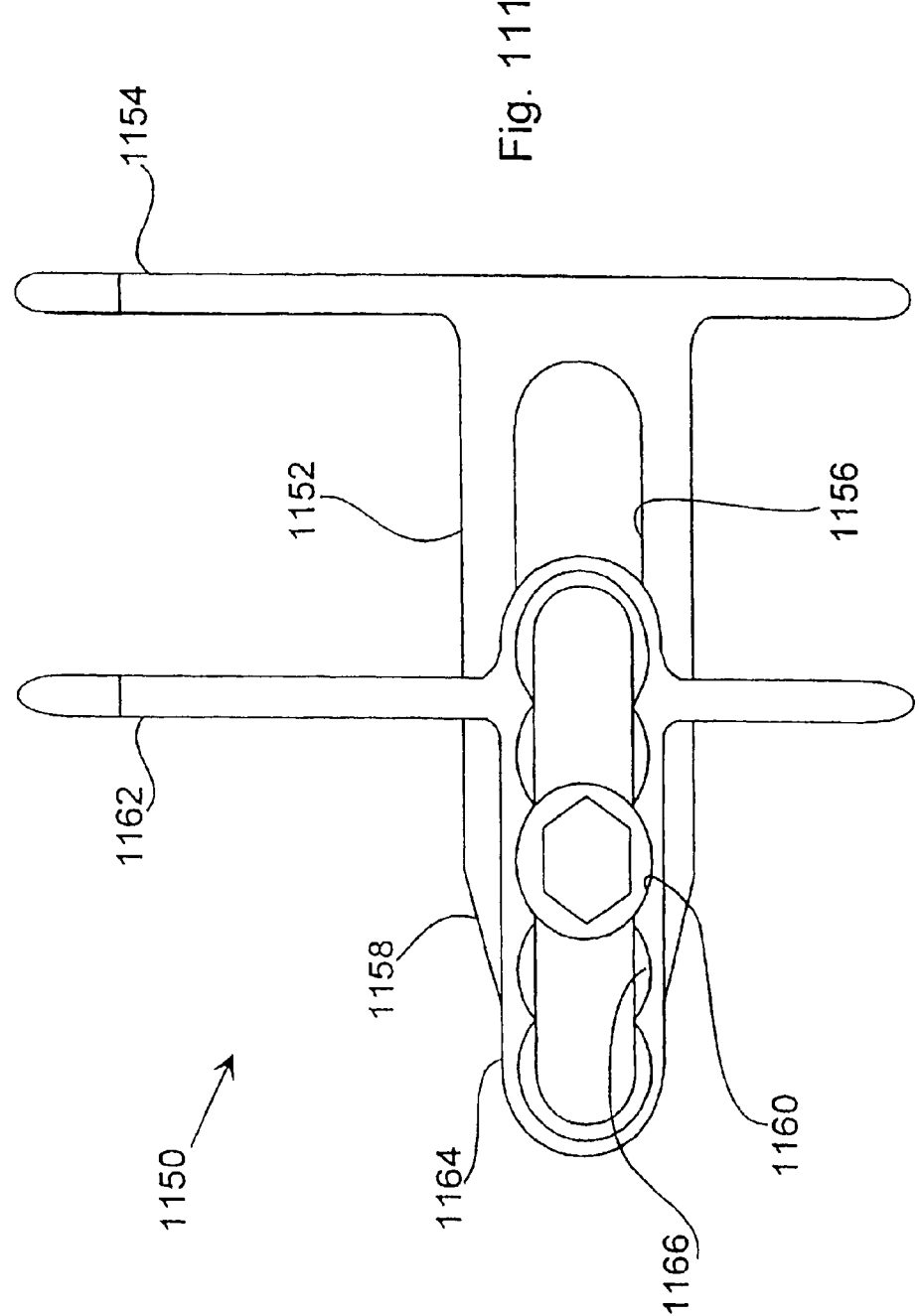

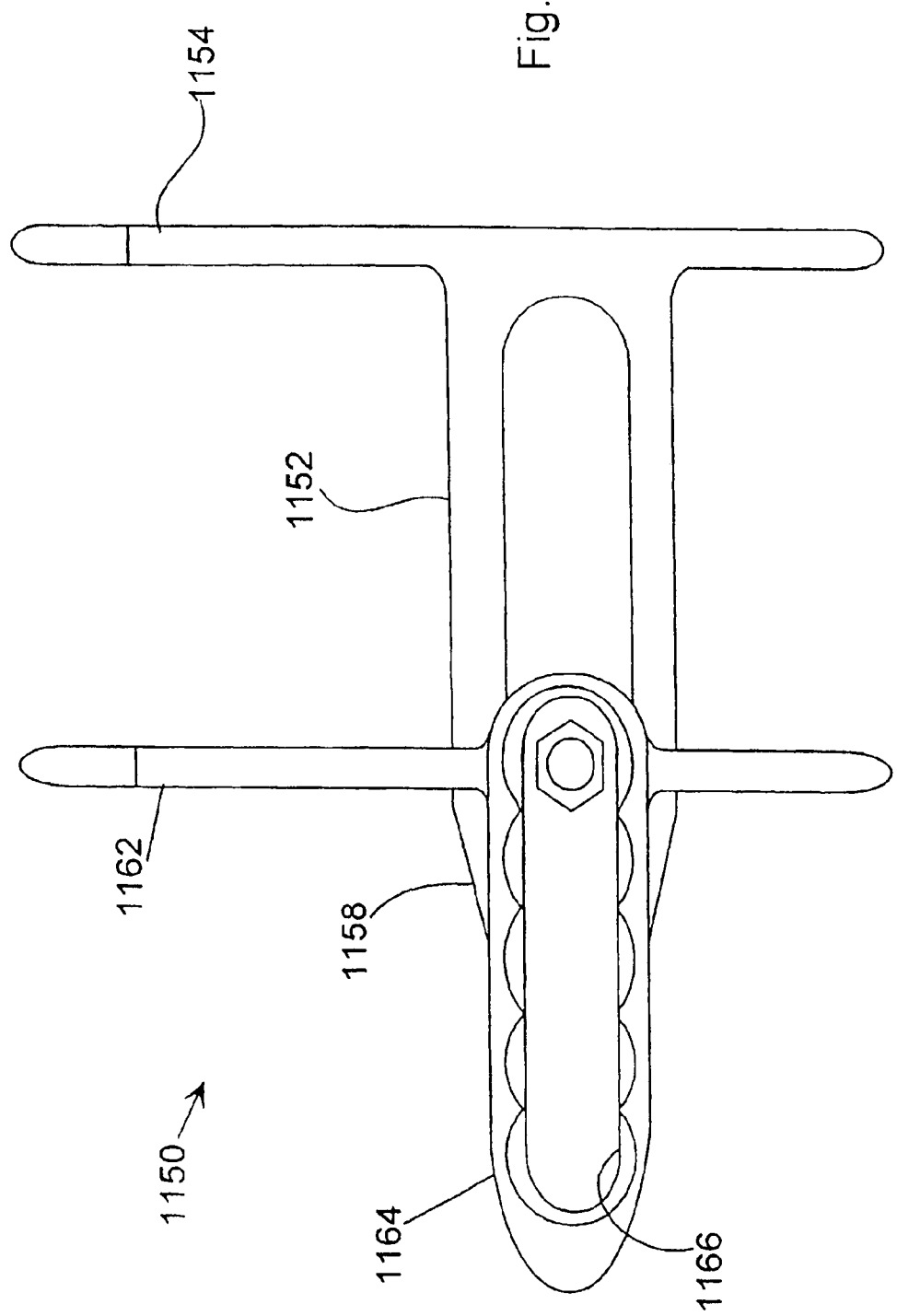

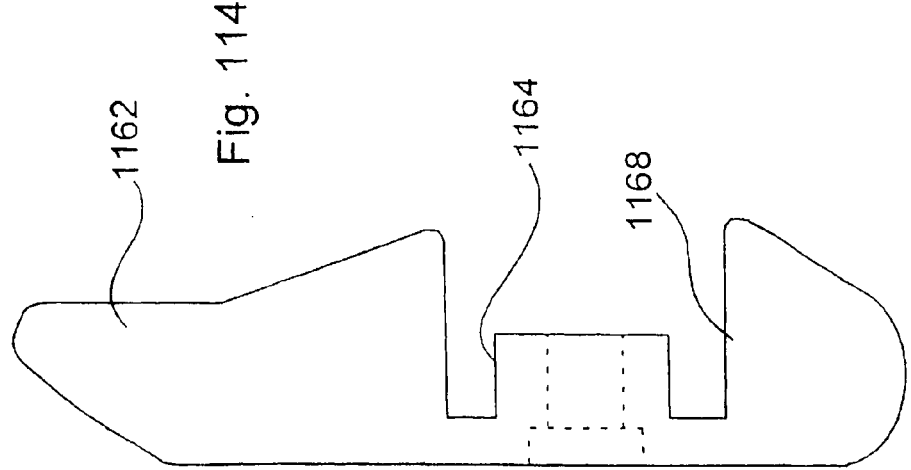
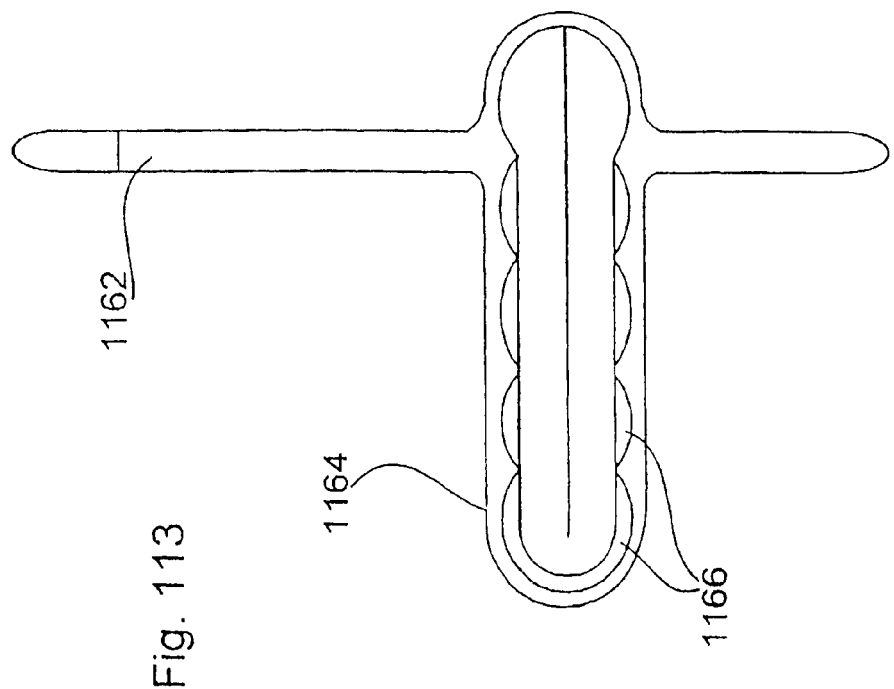

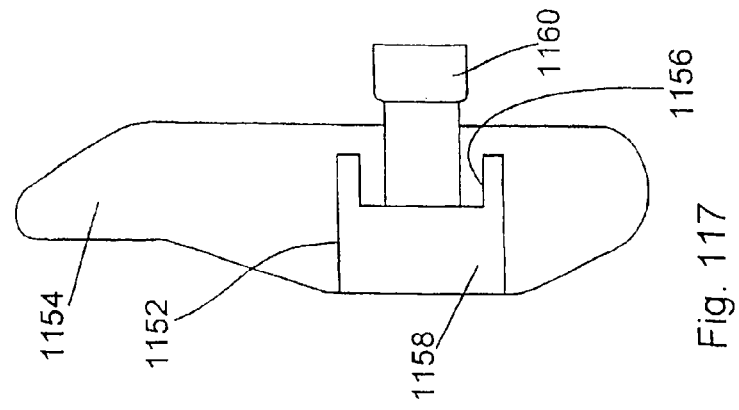
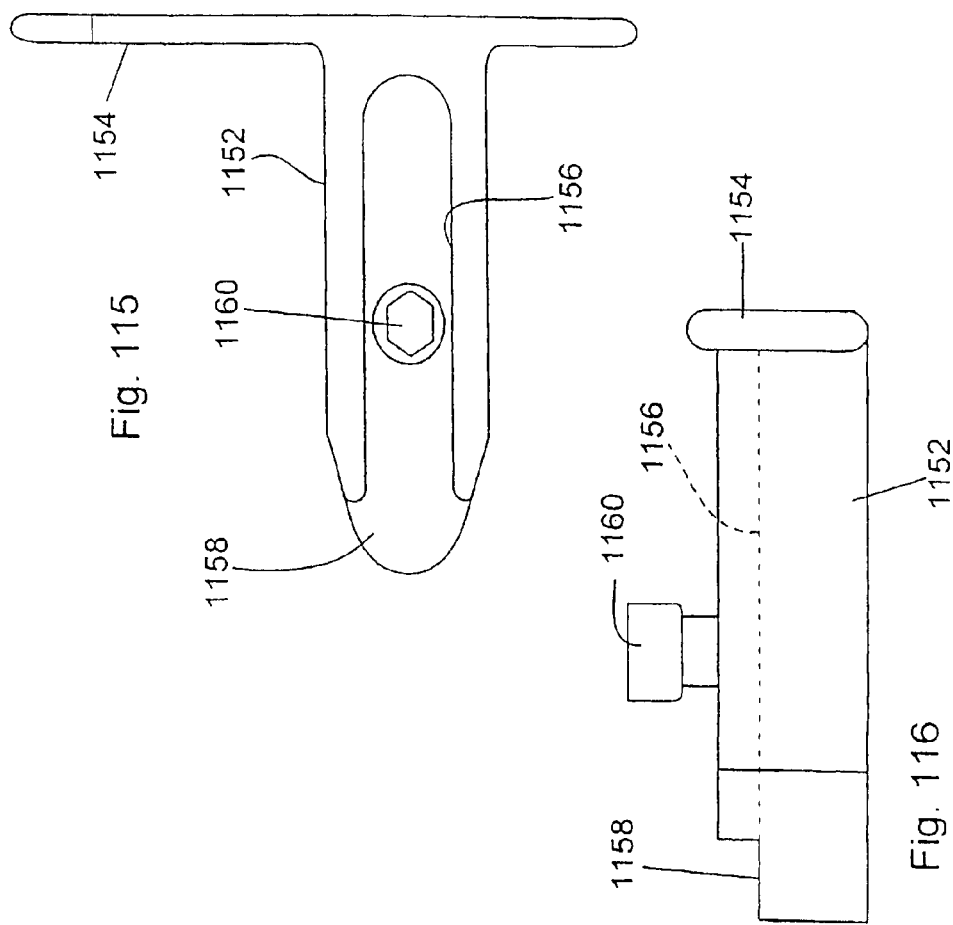

SPINE DISTRACTION IMPLANT AND METHOD

CROSS-REFERENCE TO RELATED APPLICATIONS

This application is a continuation of U.S. patent application Ser. No. 10/732,589, entitled "Spine Distraction Implant," filed Dec. 10, 2003, which is a divisional application of U.S. patent application Ser. No. 09/842,756, entitled "Spine Distraction Implant," filed Apr. 26, 2001, now U.S. Pat. No. 6,699,247, which is a continuation of U.S. patent application Ser. No. 09/474,038, entitled "Spine Distraction Implant," filed Dec. 28, 1999, now U.S. Pat. No. 6,332,882, which is a continuation of U.S. patent application Ser. No. 09/175,645, entitled "Spine Distraction Implant," filed Oct. 20, 1998, now U.S. Pat. No. 6,068,630, which is a continuation-in-part of U.S. patent application Ser. No. 08/958,281, entitled "Spine Distraction Implant and Method," filed Oct. 27, 1997, now U.S. Pat. No. 5,860,977, which is a continuation-in-part of U.S. patent application Ser. No. 08/778,093, entitled "Spine Distraction Implant and Method," filed Jan. 2, 1997, now U.S. Pat. No. 5,836,948, each of which is incorporated herein by reference in its entirety.

BACKGROUND

As the present society ages, it is anticipated that there will be an increase in adverse spinal conditions which are characteristic of older people. By way of example, with aging comes increases in spinal stenosis (including but not limited to central canal and lateral stenosis), the thickening of the bones which make up the spinal column and facet arthropathy. Spinal stenosis is characterized by a reduction in the available space for the passage of blood vessels and nerves. Pain associated with such stenosis can be relieved by medication and/or surgery. Of course, it is desirable to eliminate the need for major surgery for all individuals and in particular for the elderly.

Accordingly, there needs to be developed procedures and implants for alleviating such condition which are minimally invasive, can be tolerated by the elderly and can be performed preferably on an outpatient basis.

SUMMARY

The present invention is directed to providing a minimally invasive implant and method for alleviating discomfort associated with the spinal column.

The present invention provides for apparatus and method for relieving pain by relieving the pressure and restrictions on the aforementioned blood vessels and nerves. Such alleviation of pressure is accomplished in the present invention through the use of an implant and method which distract the spinous process of adjacent vertebra in order to alleviate the problems caused by spinal stenosis and facet arthropathy and the like. While the implant and method particularly address the needs of the elderly, the invention can be used with individuals of all ages and sizes where distraction of the spinous process would be beneficial.

In one aspect of the invention, an implant is provided for relieving pain comprising a device positioned between a first spinous process and a second spinous process. The device includes a spinal column extension stop and a spinal column flexion non-inhibitor.

In another aspect of the invention, the implant is positioned between the first spinous process and the second spinous process and includes a distraction wedge that can distract the first and second spinous processes as the implant is positioned between the spinous processes.

In yet another aspect of the present invention, the implant includes a device which is adapted to increasing the volume of the spinal canal and/or the neural foramen as the device is positioned between adjacent spinous processes.

In yet a further aspect of the present invention, a method is presented for relieving pain due to the development of, by way of example only, spinal stenosis and facet arthropathy. The method is comprised of the steps of accessing adjacent first and second spinal processes of the spinal column and distracting the processes a sufficient amount in order to increase the volume of the spinal canal in order to relieve pain. The method further includes implanting a device in order to maintain the amount of distraction required to relieve such pain.

In yet a further aspect of the invention, the method includes implanting a device in order to achieve the desired distraction and to maintain that distraction.

In yet a further aspect of the invention, the implant includes a first portion and a second portion. The portions are urged together in order to achieve the desired distraction.

In still a further aspect of the invention, the implant includes a distracting unit and a retaining unit. The distracting unit includes a body which can be urged between adjacent spinous processes. The body includes a slot. After the distracting unit is positioned, the retaining unit can fit into the slot of the retaining unit and be secured thereto.

In yet a further aspect of the invention, the implant includes a first unit with a central body. A sleeve is provided over the central body and is at least partially spaced from the central body in order to allow for deflection toward the central body.

In a further aspect of the invention, the implant includes a first unit having a central body with a guide and a first wing, with the first wing located at first end of the body. The guide extends from a second end of the body located distally from the first wing. The implant further includes a sleeve provided over said central body. The sleeve is at least partially spaced from the central body in order to allow for deflection of the sleeve toward the central body. The implant further includes a second wing and a device for securing the second wing to the first unit, wherein the sleeve is located between the first and second wings.

In yet another aspect of the invention, an implant system includes a cylindrical sleeve which is inwardly deflectable. The system further includes an insertion tool which includes an insertion guide, a central body, a stop and a handle. The guide and the stop extend from opposite sides of the central body and the handle extend from the stop. A sleeve fits over the guide and against the stop preparatory to being positioned between the two adjacent vertebrae with the insertion tool.

In yet a further aspect of the invention, the implant includes central body and first and second wings and a means for selectively positioning one of the first and second wings relative to the other in order to accommodate spinous processes of different sizes.

Other implants and methods within the spirit and scope of the invention can be used to increase the volume of the spinal canal thereby alleviating restrictions on vessels and nerves associated therewith, and pain.

BRIEF DESCRIPTION OF THE DRAWINGS

FIG. 1 depicts the implant in a more extended configuration than does FIG. 2.

FIGS. 6, 7, 8, 9 and 10 depict apparatus and method for another embodiment of the present invention for creating distraction between adjacent spinous processes.

FIGS. 11, 12 and 13 depict yet a further embodiment of the invention for creating distraction between adjacent spinous processes.

FIGS. 16, 16a, and 17 depict yet another embodiment of the present invention.

FIGS. 26, 27 and 28 depict another embodiment of the invention.

FIGS. 29 and 30 depict side elevational views of differently shaped implants of embodiments of the present invention.

FIGS. 34 and 35 depict yet another apparatus and method of the present invention.

FIGS. 36, 37 and 38 depict three different embodiments of the present invention.

FIGS. 39 and 40 depict yet another apparatus and method of an embodiment of the present invention.

FIG. 44 is still a further embodiment of an implant of the invention.

FIG. 45 is yet another depiction of an apparatus and method of the invention.

FIGS. 46 and 47 depict still a further apparatus and method of an embodiment of the invention.

FIGS. 48, 49, 50 and 51 depict yet a further apparatus and method of the invention.

FIGS. 52, 53, 54, 55a and 55b depict another apparatus and method of the invention.

FIGS. 59 and 60 depict still a further embodiment of the invention.

FIG. 61 depict another embodiment of the invention.

FIGS. 62 and 63 depict yet another embodiment of the present invention.

FIGS. 79, 80, 80a, 81, 82, 83, 83a, 84, 85, 86 and 87 depict still a further embodiment of the present invention.

FIGS. 88, 89, 90 and 91 depict yet another embodiment of the present invention.

FIGS. 92, 92a, 92b, 93, 93a, 93b, 93c, 93d, 94, 94a, 94b, 95, 95a, and 96, depict still a further embodiment of the present invention wherein a sleeve is provided which is capable of deflecting response to relative motion between the spinous processes.

FIGS. 111, 112, 113, 114, 115, 116, and 117 depict yet another embodiment of the present invention.

For simplicity in description, identical components are labeled by the same numerals in this application.

DETAILED DESCRIPTION

Embodiment of FIGS. 1-5a, 5b

Figure 1:
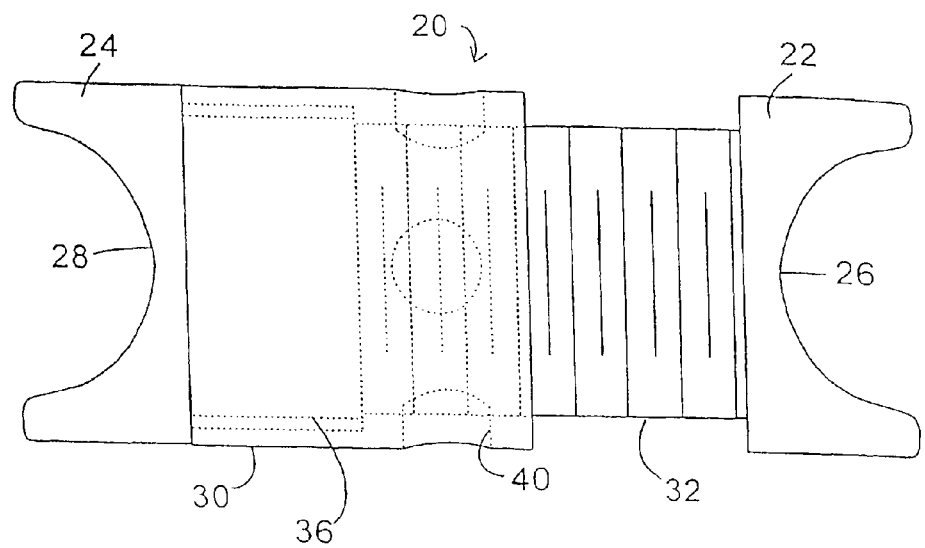
FIGS. 1 and 2 depict an embodiment of an implant of the invention which is adjustable in order to select the amount of distraction required.

A first embodiment of the invention is shown in FIGS. 1-5a, 5b. Implant 20 includes first and second forked ends 22 and 24, each defining a saddle 26, 28 respectively. The forked ends 22, 24 are mated using an interbody piece 30. As can be seen in FIGS. 3a, 3b, the first forked end 22 includes a threaded shaft 32 which projects rearwardly from the saddle 26. The threaded shaft 32 fits into the threaded bore 34 (FIG. 4a) of the interbody piece 30.

The second forked end 24 (FIGS. 5a, 5b) includes a smooth cylindrical shaft 36 which can fit into the smooth bore 38 of the interbody piece 30.

Figure 2:
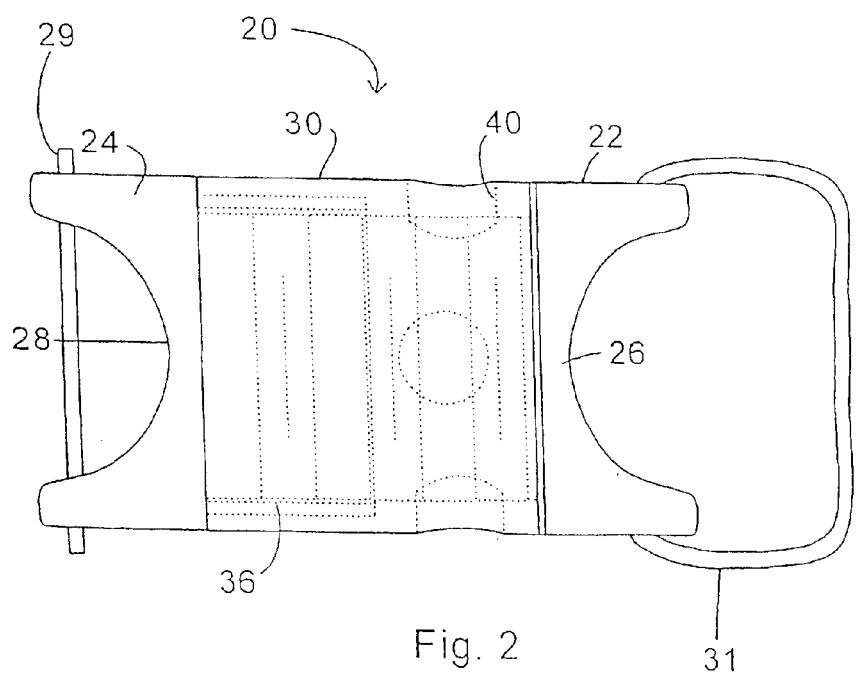
Figure 3A:
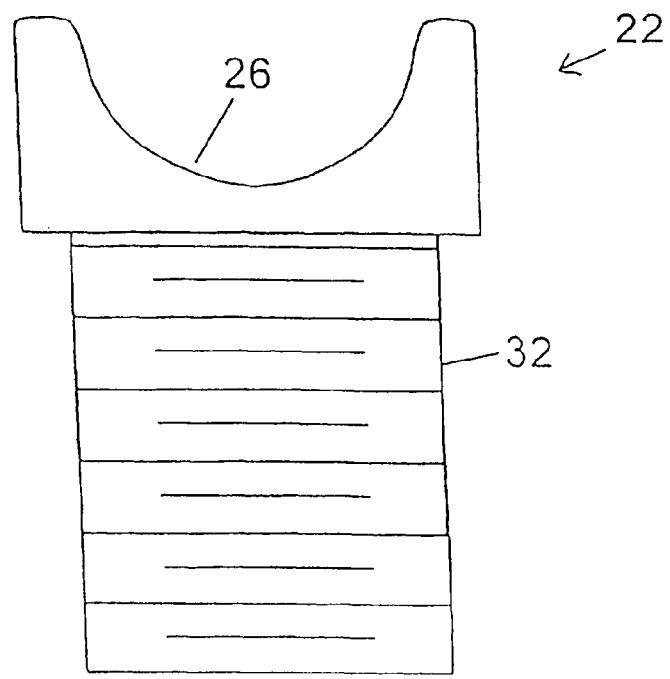
FIGS. 3a and 3b depict side and end views of a first forked and of the embodiment of FIG. 1.
Figure 3B:
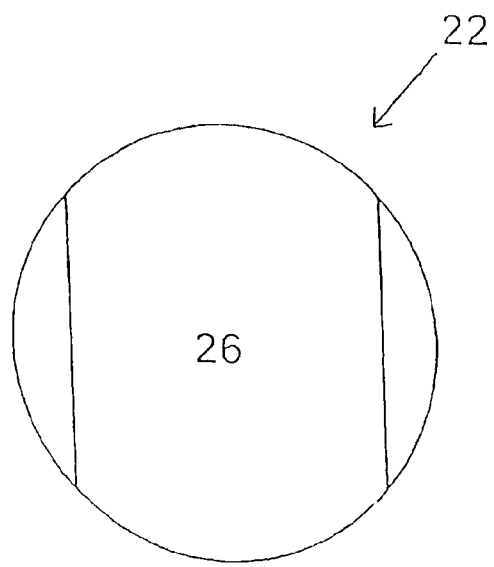
Figure 4A:
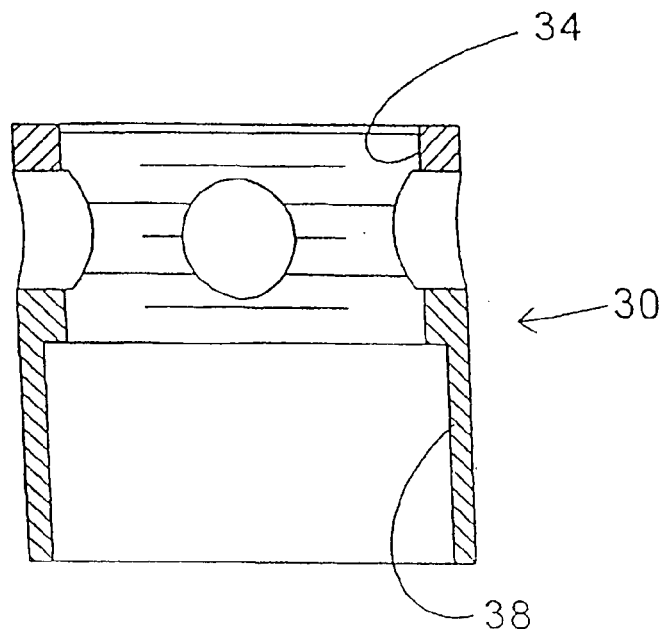
FIGS. 4a and 4b depict side sectioned and end views of an interbody piece of the implant of FIG. 1.
Figure 4B:
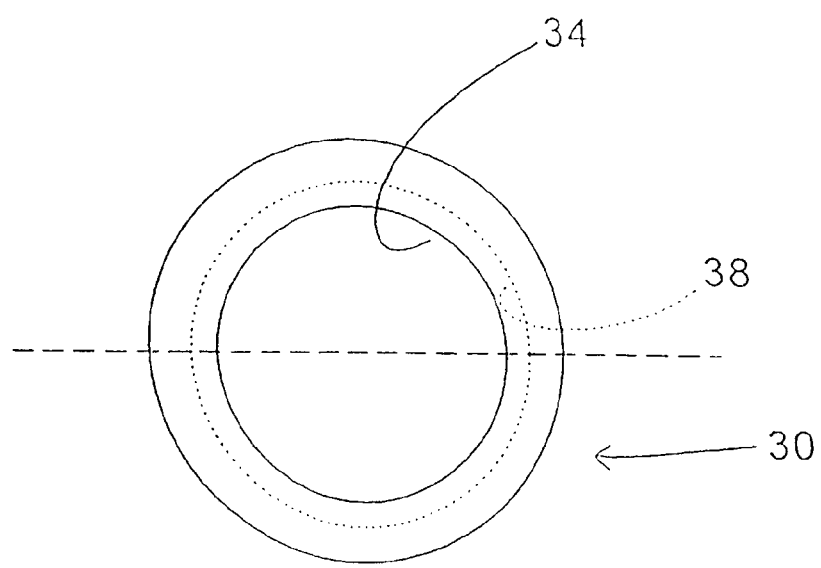
Figure 5A:
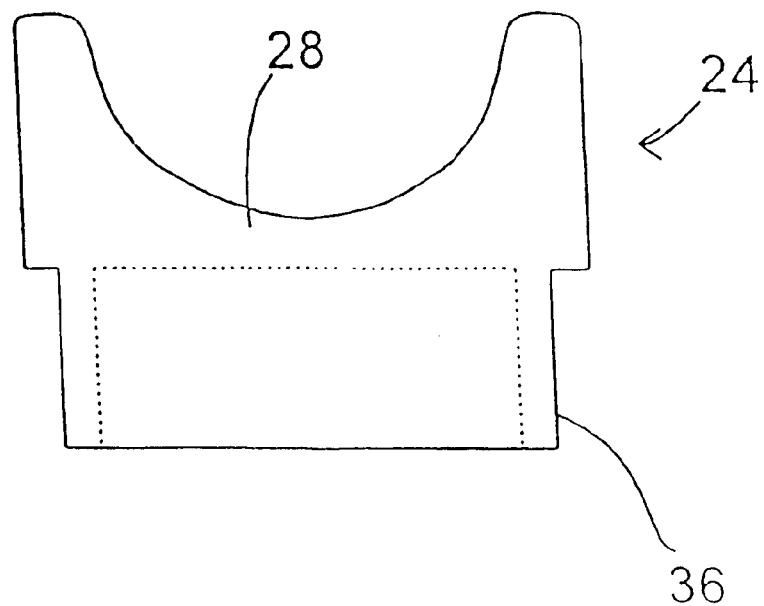
FIGS. 5a and 5b depict side and end views of a second forked end of the embodiment of FIG. 1.
Figure 5B:
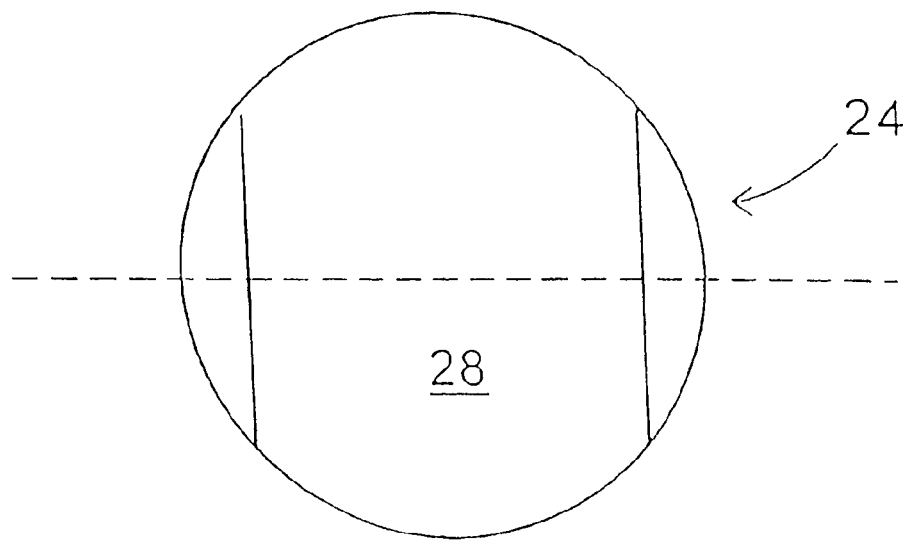

FIG. 1 shows the implant 20 in a fully extended position, while FIG. 2 shows the implant in an unextended position. In the unextended position, it can be seen that the threaded shaft 32 of the first forked end 22 fits inside the hollow cylindrical shaft 36 of the second forked end 24.

For purposes of implantation between adjacent first and second spinous processes of the spinal column, the implant 20 is configured as shown in FIG. 2. The first and second spinous processes are exposed using appropriate surgical techniques and thereafter, the implant 20 is positioned so that saddle 26 engages the first spinous process, and saddle 28 engages the second spinous process. At this point, the interbody piece 30 can be rotated by placing an appropriate tool or pin into the cross holes 40 and upon rotation, the saddle 26 is moved relative to the saddle 28. Such rotation spreads apart or distracts the spinous processes with the resultant and beneficial effect of enlarging the volume of the spinal canal in order to alleviate any restrictions on blood vessels and nerves.

It is noted that this implant as well as the several other implants described herein act as an extension stop. That means that as the back is bent backwardly and thereby placed in extension the spacing between adjacent spinous processes cannot be reduced to a distance less than the distance between the lowest point of saddle 26 and the lowest point of saddle 28.

This implant, however, does not inhibit or in any way limit the flexion of the spinal column, wherein the spinal column is bent forward.

Preferably, such a device provides for distraction in the range of about 5 mm to about 15 mm. However, devices which can distract up to and above 22 mm may be used depending on the characteristics of the individual patient.

With all the ligaments (such as the supraspinous ligament) and tissues associated with the spinous processes left intact, the implant 20 can be implanted essentially floating in position in order to gain the benefits of the aforementioned extension stop and flexion non-inhibitor. If desired, one of the saddles 26 can be laterally pinned with pin 29 to one of the spinous processes and the other saddle can be loosely associated with the other spinous processes by using a tether 31 which either pierces or surrounds the other spinous process and then is attached to the saddle in order to position the saddle relative to the spinous process. Alternatively, both saddles can be loosely tethered to the adjacent spinous process in order to allow the saddles to move relative to the spinous processes.

The shape of the saddles, being concave, gives the advantage of distributing the forces between the saddle and the respective spinous process. This ensures that the bone is not resorbed due to the placement of the implant 20 and that the structural integrity of the bone is maintained.

The implant 20 in this embodiment can be made of a number of materials, including but not limited to, stainless steel, titanium, ceramics, plastics, elastics, composite materials or any combination of the above. In addition, the modulus of elasticity of the implant can be matched to that of bone, so that the implant 20 is not too rigid. The flexibility of the implant can further be enhanced by providing additional apertures or perforations throughout the implant in addition to the holes 40 which also have the above stated purpose of allowing the interbody piece 30 to be rotated in order to expand the distance between the saddle 26, 28.

In the present embodiment, it is understood that the spinous processes can be accessed and distracted initially using appropriate instrumentation, and that the implant 20 can be inserted and adjusted in order to maintain and achieve the desired distraction. Alternatively, the spinous process can be accessed and the implant 20 appropriately positioned. Once positioned, the length of the implant can be adjusted in order to distract the spinous processes or extend the distraction of already distracted spinous processes. Thus, the implant can be used to create a distraction or to maintain a distraction which has already been created.

The placement of implants such as implant 20 relative to the spinous process will be discussed herein with other embodiments. However, it is to be noted that ideally, the implant 20 would be placed close to the instantaneous axis of rotation of the spinal column so that the forces placed on the implant 20 and the forces that the implant 20 places on the spinal column are minimized.

Further, it is noted that during the actual process of installing or implanting the implant 20, that the method uses the approach of extending the length of the implant 20 a first amount and then allowing the spine to creep or adjust to this distraction. Thereafter, implant 20 would be lengthened another amount, followed by a period where the spine is allowed to creep or adjust to this new level of distraction. This process could be repeated until the desired amount of distraction has been accomplished. This same method can be used with insertion tools prior to the installation of an implant. The tools can be used to obtain the desired distraction using a series of spinal distraction and spine creep periods before an implant is installed.

Embodiment of FIGS. 6, 7, 8, 9 and 10

The embodiment of the invention shown in the above FIGS. 6, 7, 8, 9 and 10 includes distraction or spreader tool 50 which has first and second arms 52, 54. Arms 52, 54 are pivotal about pivot point 56 and releaseable from pivot point 56 in order to effect the implantation of implant 58. As can be seen in FIG. 6, in cross-section, the arms 52, 54 are somewhat concave in order to cradle and securely hold the first spinous process 60 relative to arm 52 and the second spinous process 62 relative to arm 54. The distraction tool 50 can be inserted through a small incision in the back of the patient in order to address the space between the first spinous process 60 and the second spinous process 62. Once the tool 50 is appropriately positioned, the arms 52, 54 can be spread apart in order to distract the spinous processes. After this has occurred, an implant 58 as shown in FIGS. 8 and 9, or of a design shown in other of the embodiments of this invention, can be urged between the arms 52, 54 and into position between the spinous processes. After this occurs, the arms 52, 54 can be withdrawn from the spinous processes leaving the implant 58 in place. The implant 58 is urged into place using a tool 64 which can be secured to the implant 58 through a threaded bore 66 in the back of the implant. As can be seen in FIG. 10, the implant 58 includes saddles 68 and 70 which cradle the upper and lower spinous processes 60, 62 in much the same manner as the above first embodiment and also in much the same manner as the individual arms of the tool 50. The saddles as described above tend to distribute the load between the implant and the spinous processes and also assure that the spinous process is stably seated at the lowest point of the respective saddles.

Figure 12:
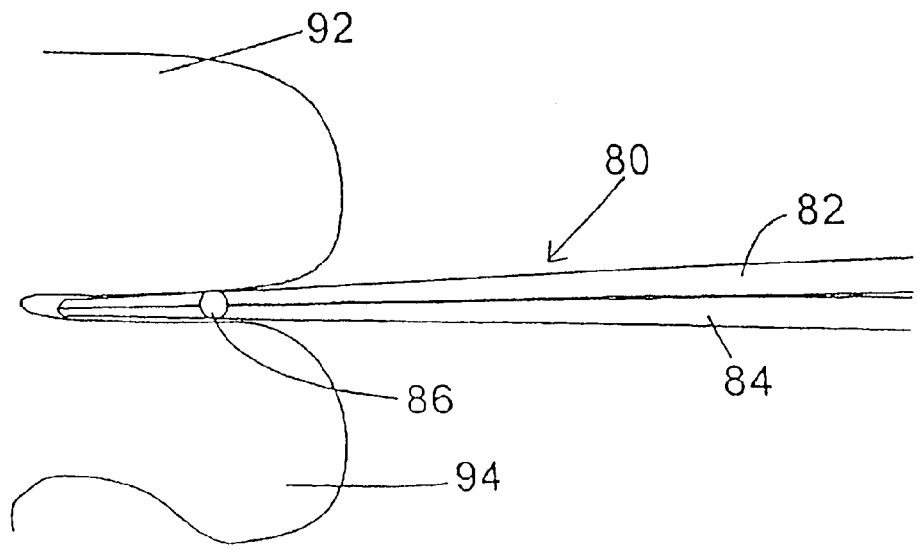
Figure 13:
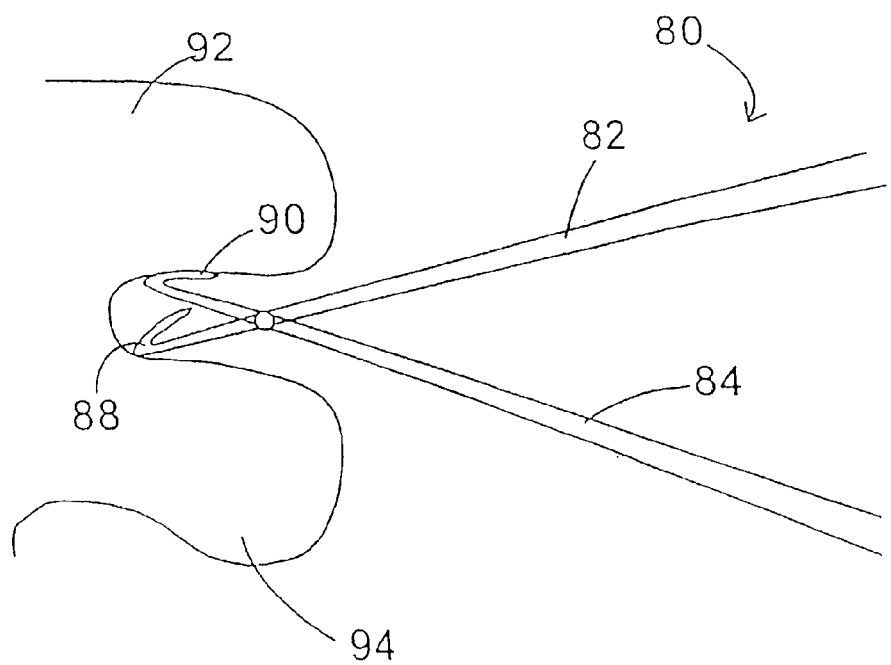

Embodiment of FIGS. 11, 12 and 13

Another embodiment of the apparatus and method of the invention is shown in FIGS. 11, 12 and 13. In this embodiment, the spreader or distraction tool 80 includes first and second arms 82, 84 which are permanently pivoted at pivot point 86. The arms include L-shaped ends 88, 90. Through a small incision, the L-shaped ends 88, 90 can be inserted between the first and second spinous processes 92, 94. Once positioned, the arms 82, 84 can be spread apart in order to distract the spinous processes. The implant 96 can then be urged between the spinous processes in order to maintain the distraction. It is noted that implant 96 includes wedged surfaces or ramps 98, 100. As the implant 96 is being urged between the spinous processes, the ramps further cause the spinous processes to be distracted. Once the implant 96 is fully implanted, the full distraction is maintained by the planar surfaces 99, 101 located rearwardly of the ramps. It is to be understood that the cross-section of the implant 96 can be similar to that shown for implant 58 or similar to other implants in order to gain the advantages of load distribution and stability.

Embodiments of FIGS. 14, 15, 16, 16*a*, and 17

Figure 14:
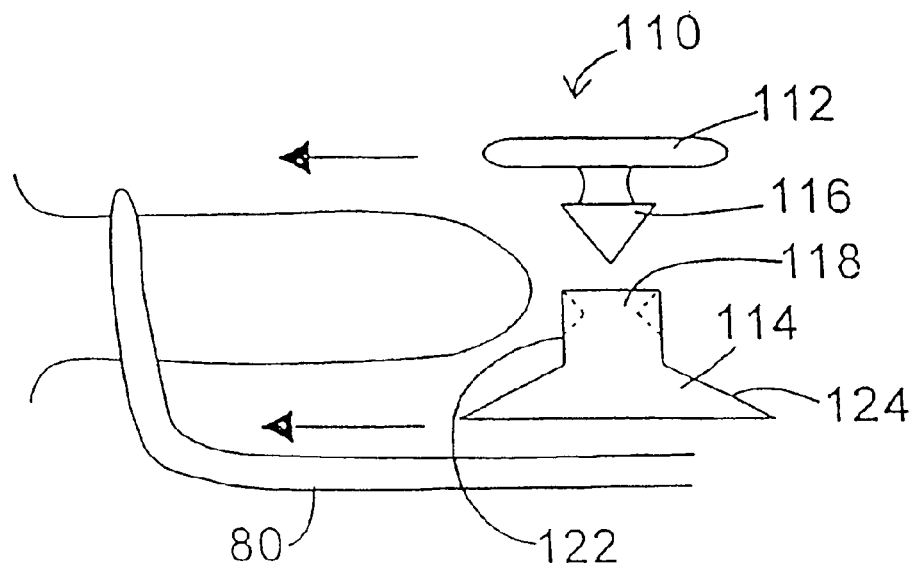
FIGS. 14 and 15 depict a further apparatus and method of an embodiment of the invention for creating distraction.
Figure 15:
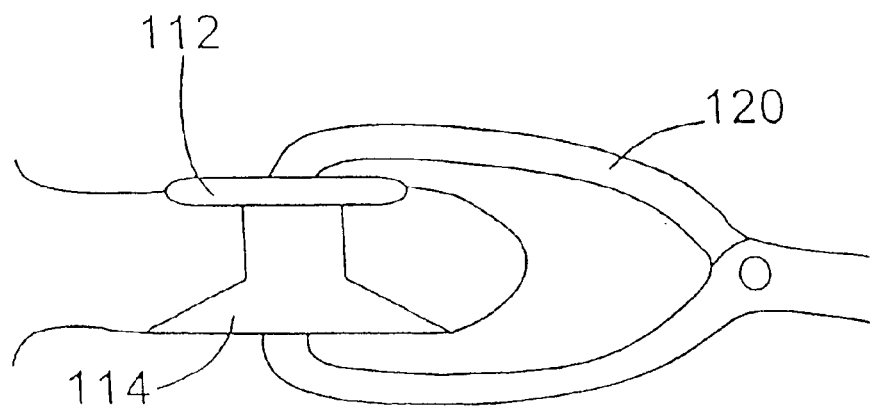

In FIGS. 14 and 15, yet another embodiment of the invention is depicted. In this embodiment, the implant 110 includes first and second conically shaped members 112, 114. Member 112 includes a male snap connector 116 and member 114 includes a female snap connector 118. With male snap connector 116 urged into female snap connector 118, the first member 112 is locked to the second member 114. In this embodiment, a distraction or spreader tool 80 could be used. Once the spinous process has been spread apart, an implantation tool 120 can be used to position and snap together the implant 110. The first member 112 of implant 110 is mounted on one arm and second member 114 is mounted on the other arm of tool 120. The member 112, 114 are placed on opposite sides of the space between adjacent spinous processes. The members 112, 114 are urged together so that the implant 110 is locked in place between the spinous processes as shown in FIG. 15. It is to be noted that the implant 110 can also be made more self-distracting by causing the cylindrical surface 122 to be more conical, much as surface 124 is conical, in order to hold implant 110 in place relative to the spinous processes and also to create additional distraction.

An alternative embodiment of the implant can be seen in FIGS. 16 and 17. This implant 130 includes first and second members 132, 134. In this particular embodiment, the implants are held together using a screw (not shown) which is inserted through countersunk bore 136 and engages a threaded bore 138 of the second member 134. Surfaces 139 are flattened (FIG. 17) in order to carry and spread the load applied thereto by the spinous processes.

The embodiment of implant 130 is not circular in overall outside appearance, as is the embodiment 110 of FIGS. 14 and 15. In particular, with respect to the embodiment of implant 130 of FIGS. 16 and 17, this embodiment is truncated so that the lateral side 140, 142 are flattened with the upper and lower sides 144, 146 being elongated in order to capture and create a saddle for the upper and lower spinous processes. The upper and lower sides, 144, 146 are rounded to provide a more anatomical implant which is compatible with the spinous processes.

If it is desired, and in order to assure that the first member 132 and the second member 134 are aligned, key 148 and keyway 150 are designed to mate in a particular manner. Key 148 includes at least one flattened surface, such as flattened surface 152, which mates to an appropriately flattened surface 154 of the keyway 150. In this manner, the first member is appropriately mated to the second member in order to form appropriate upper and lower saddles holding the implant 130 relative to the upper and lower spinous processes.

Figure 16A:
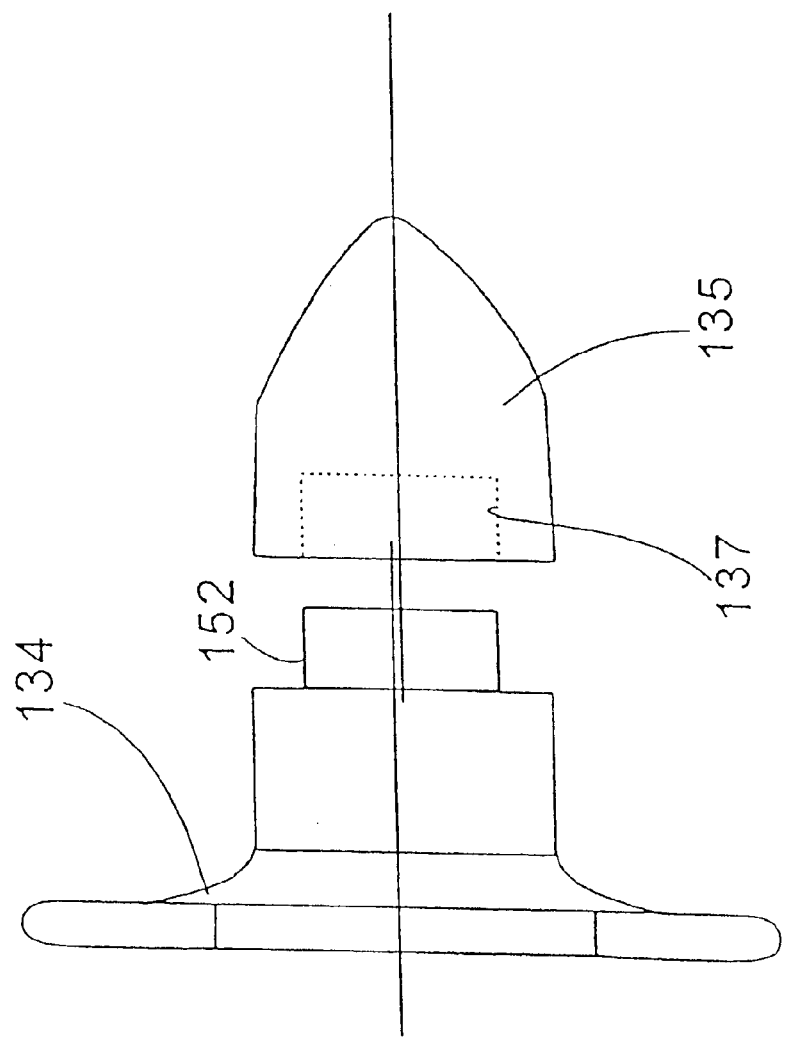

FIG. 16a depicts second member 134 in combination with a rounded nose lead-in plug 135. Lead-in plug 135 includes a bore 137 which can fit snugly over key 148. In this configuration, the lead-in plug 135 can be used to assist in the placement of the second member 134 between spinous processes. Once the second member 134 is appropriately positioned, the lead-in plug 135 can be removed. It is to be understood that the lead-in plug 135 can have other shapes such as pyramids and cones to assist in urging apart the spinous processes and soft tissues in order to position the second member 134.

Figure 18:
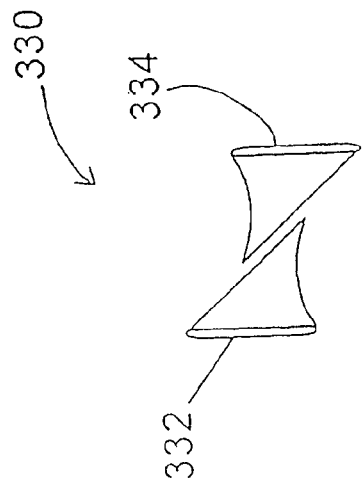
FIGS. 18, 19 and 20 depict yet a further apparatus and method of the present embodiment.
Figure 19:
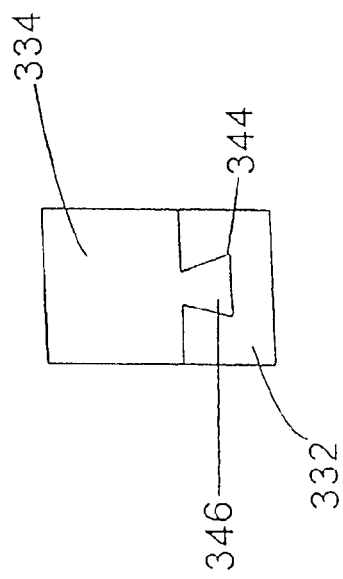
Figure 20:
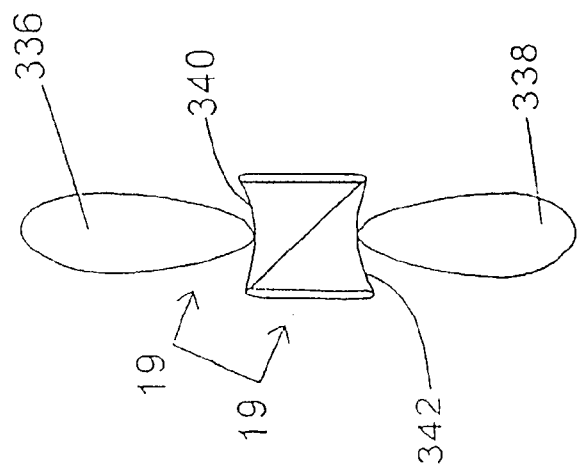

Embodiment of FIGS. 18, 19 and 20

The implant 330 as shown in FIG. 18 is comprised of first and second mating wedges 332 and 334. In order to implant these wedges 332, 334, the spinous processes are accessed from both sides and then a tool is used to push the wedges towards each other. As the wedges are urged towards each other, the wedges move relative to each other so that the combined dimension of the implant 330 located between the upper and lower spinous processes 336, 338 (FIG. 20), increases, thereby distracting the spinous processes. It is noted that the wedges 332, 334 include saddle 340, 342, which receiving the spinous processes 336, 338. These saddles have the advantages as described hereinabove.

The first or second wedges 332, 334 have a mating arrangement which includes a channel 344 and a projection of 346 which can be urged into the channel in order to lock the wedges 332, 334 together. The channel 334 is undercut in order to keep the projection from separating therefrom. Further, as in other devices described herein, a detent can be located in one of the channel and the projection, with a complimentary recess in the other of the channel and the projection. Once these two snap together, the wedges are prevented from sliding relative to the other in the channel 344.

While the above embodiment was described with respect to wedges, the wedges could also have been designed substantially as cones with all the same features and advantages.

Figure 22:
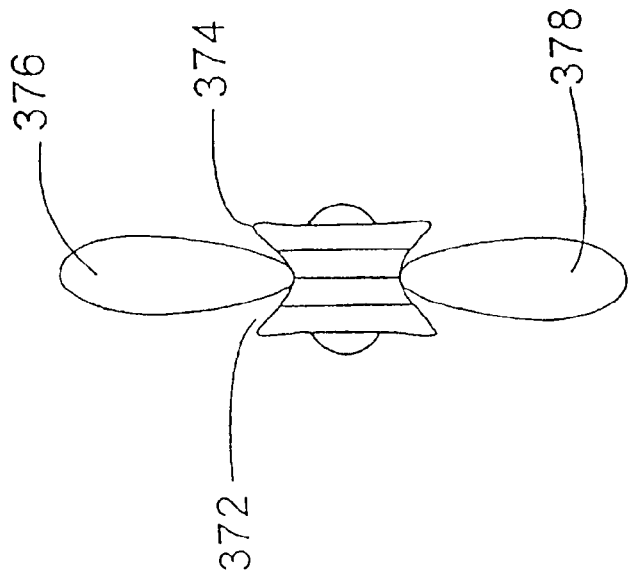
FIGS. 21 and 22 depict still a further embodiment of the present invention.
Figure 21:
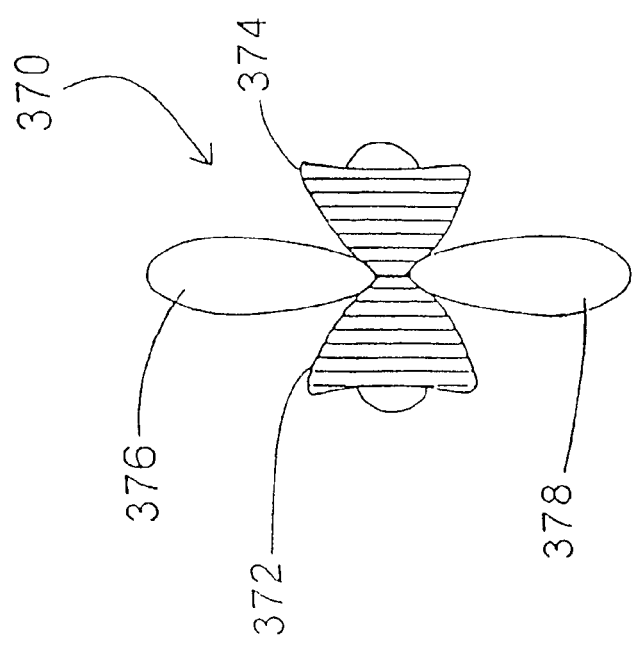

Embodiments of FIGS. 21 and 22

The implant 370 is comprised of first and second distraction cone 372, 374. These cones are made of a flexible material. The cones are positioned on either side of the spinous processes 376, 378 as shown in FIG. 21. Using appropriate tool as shown hereinabove, the distraction cones 372, 374 are urged together. As they are urged together, the cones distract the spinous processes as shown in FIG. 22. Once this has occurred, an appropriate screw or other type of fastening mechanism 380 can be used to maintain the position of the distraction cones 372, 374. The advantage of this arrangement is that the implant 370 is self-distracting and also that the implant, being flexible, molds about the spinous processes as shown in FIG. 22.

Figure 24:
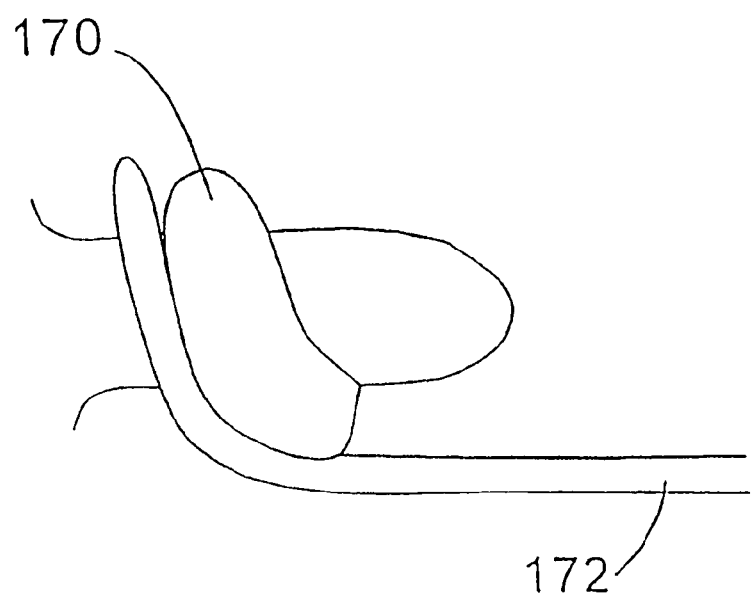
FIGS. 23, 24 and 25 depict another embodiment of the present invention.
Figure 23:
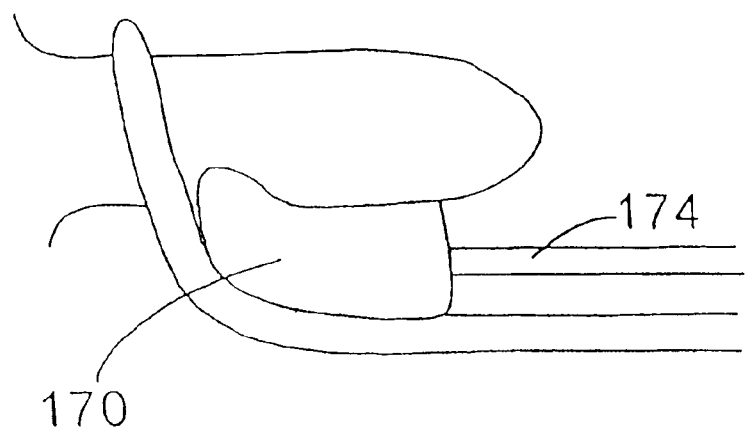
Figure 25:
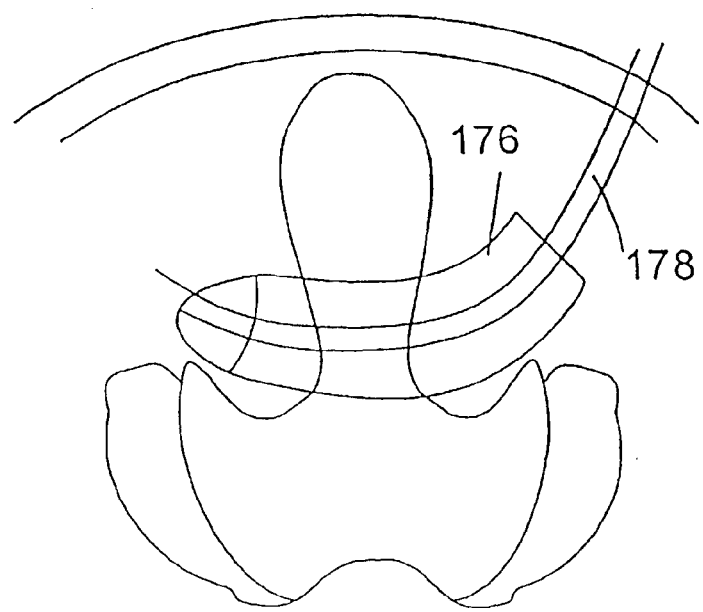

Embodiments of FIGS. 23, 24 and 25

In FIGS. 23 and 24, another embodiment of the implant 170 is depicted. This implant is guided in place using an L-shaped guide 172 which can have a concave cross-section such as the cross-section 52 of retraction tool 50 in FIG. 6 in order to cradle and guide the implant 170 in position. Preferably a small incision would be made into the back of the patient and the L-shaped guide tool 172 inserted between the adjacent spinous processes. The implant 170 would be mounted on the end of insertion tool 174 and urged into position between the spinous processes. The act of urging the implant into position could cause the spinous processes to be further distracted if that is required. Prior to the insertion of the L-shaped guide tool 172, a distraction tool such as shown in FIG. 13 could be used to initially distract the spinous processes.

Implant 170 can be made of a deformable material so that it can be urged into place and so that it can somewhat conform to the shape of the upper and lower spinous processes. This deformable material would be preferably an elastic material. The advantage of such a material would be that the load forces between the implant and the spinous processes would be distributed over a much broader surface area. Further, the implant would mold itself to an irregular spinous process shape in order to locate the implant relative to spinous processes.

With respect to FIG. 25, this implant 176 can be inserted over a guide wire, guide tool or stylet 178. Initially, the guide wire 178 is positioned through a small incision to the back of the patient to a position between the adjacent spinous processes. After this has occurred, the implant is threaded over the guide wire 178 and urged into position between the spinous processes. This urging can further distract the spinous processes if further distraction is required. Once the implant is in place, the guide tool 178 is removed and the incision closed. The insertion tools of FIGS. 23 and 24 can also be used if desired.

Figure 26:
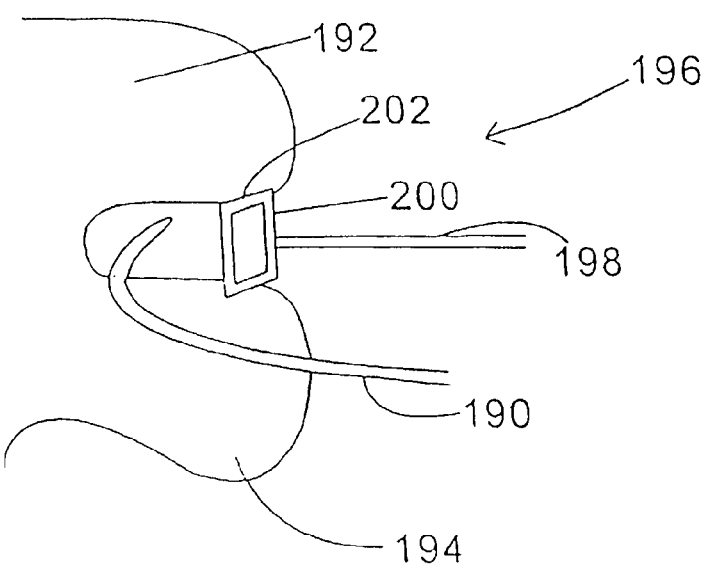

Embodiment of FIGS. 26, 27 and 28

The embodiment shown in FIGS. 26, 27 and 28 uses an implant similar to that depicted in FIGS. 8 and 9 with different insertion tools. As can be seen in FIG. 26, an L-shaped distraction tool 190 is similar to L-shaped distraction tool 80 (FIG. 12), is used to distract the first and second spinous processes 192, 194. After this has occurred, an insertion tool 196 is placed between the spinous processes 192, 194. Insertion tool 196 includes a handle 198 to which is mounted a square-shaped ring 200.

The distraction tool 190 can be inserted through a small incision in the back in order to spread apart the spinous processes. Through the same incision which has been slightly enlarged laterally, an upper end 202 of ring 200 can be initially inserted followed by the remainder of the ring 200. Once the ring is inserted, the ring can be rotated slightly by moving handle 198 downwardly in order to further wedge the spinous processes apart. Once this has been accomplished, an implant such as implant 204 can be inserted through the ring and properly positioned using implant handle 206. Thereafter, the implant handle 206 and the insertion tool 196 can be removed.

Embodiments of FIGS. 29, 30, 31, 32 and 33

As can be seen in FIGS. 29 and 30, the implants 210, 212, can have different shapes when viewed from the side. These implants are similar to the above-referenced implants 58 (FIG. 8) and 204 (FIG. 28). These implants have cross-sections similar to that shown in FIG. 10 which includes saddles in order to receive and hold the adjacent spinous processes.

Figure 33:
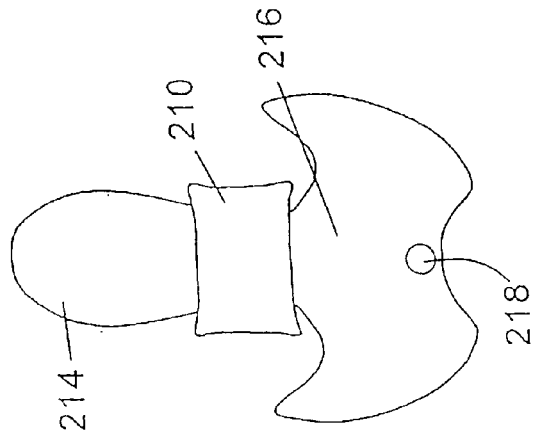
FIGS. 31, 32 and 33 depict various implant positions of an apparatus of the present invention.
Figure 32:
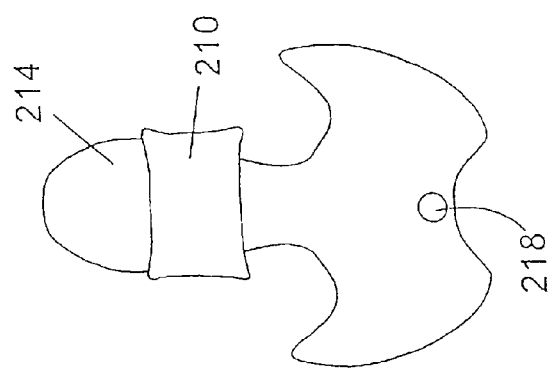
Figure 31:
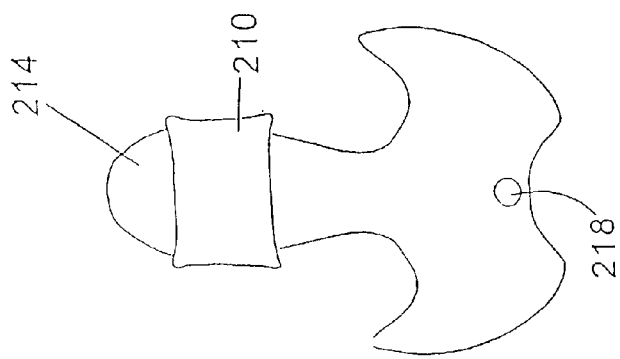

As can be seen in FIGS. 31, 32 and 33, these implants can be placed in different positions with respect to the spinous process 214. Preferably as shown in FIG. 33, the implant 210 is placed closest to the lamina 216. Being so positioned, the implant 210 is close to the instantaneous axis of rotation 218 of the spinal column, and the implant would experience least forces caused by movement of the spine. Thus, theoretically, this is the optimal location for the implant.

As can be seen in FIGS. 31 and 32, the implant can be placed midway along the spinous process (FIG. 32) and towards the posterior aspect of the spinous process (FIG. 31). As positioned shown in FIG. 31, the greatest force would be placed on the implant 210 due to a combination of compression and extension of the spinal column.

Embodiment of FIGS. 34 and 35

Another embodiment of the invention is shown in FIGS. 34 and 35. In these figures, implant 220 is comprised of a plurality of individual leaves 222 which are substantially V-shaped. The leaves include interlocking indentations or detents 224. That is, each leaf includes an indentation with a corresponding protrusion such that a protrusion of one leaf mates with an indentation of an adjacent leaf. Also associated with this embodiment is an insertion tool 226 which has a blunt end 228 which conforms to the shape of an individual leaf 222. For insertion of this implant into the space between the spinous processes as shown in FIG. 29, the insertion tool 226 first insert a single leaf 220. After that has occurred, the insertion tool then inserts a second leaf with the protrusion 224 of the second leaf snapping into corresponding indentation made by the protrusion 224 of the first leaf. This process would reoccur with third and subsequent leaves until the appropriate spacing between the spinous processes was built up. As can be seen in FIG. 29, the lateral edges 229 of the individual leaves 222 are slightly curved upwardly in order to form a saddle for receiving the upper and lower spinous processes.

Embodiments of FIGS. 36, 37 and 38

The embodiments of FIGS. 36, 37 and 38 which include implants 230, 232, and 234 respectively, are designed in such a manner so the implant locks itself into position once it is properly positioned between the spinous processes. Implant 220 is essentially a series of truncated cones and includes a plurality of ever expanding steps 236. These steps are formed by the conical bodies starting with the nose body 238 followed there behind by conical body 240. Essentially, the implant 234 looks like a fir tree placed on its side.

The implant 230 is inserted laterally throughout the opening between upper and lower spinous processes. The first body 238 causes the initial distraction. Each successive conical body distracts the spinous processes a further incremental amount. When the desired distraction has been reached, the spinous processes are locked into position by steps 236. At this point, if desired, the initial nose body 238 of the implant and other bodies 240 can be broken, snapped or sawed off if desired in order to minimize the size of the implant 230. In order for a portion of the implant 230 to be broken or snapped off, the intersection between bodies such as body 238 and 240, which is intersection line 242, would be somewhat weaken with the appropriate removal of material. It is noted that only the intersection lines of the initial conical bodies need to be so weakened. Thus, intersection line 244 between the bodies which remain between the spinous processes would not need to be weaker, as there would be no intention that the implant would be broken off at this point.

FIG. 37 shows implant 232 positioned between upper and lower spinous processes. This implant is wedge-shaped or triangular shaped in cross-sectioned and includes bore pluralities 245 and 246. Through these bores can be placed locking pins 248 and 250. The triangular or wedged-shaped implant can be urged laterally between and thus distract the upper and lower spinous processes. Once the appropriate distraction is reached, pins 248, 250 can be inserted through the appropriate bores of the bore pluralities 245 and 246 in order to lock the spinous processes in a V-shaped valley formed by pins 248, 250 on the one hand and the ramped surface 233, 235 on the other hand.

Turning to FIG. 38, the implant 234 has a triangular-shaped or wedge-shaped body similar to that shown in FIG. 32. In this embodiment, tab 252, 254 are pivotally mounted to the triangular shaped body 234. Once the implant 234 is appropriately positioned in order to distract the spinous processes to the desired amount, the tabs 252, 254 rotate into position in order to hold the implant 234 in the appropriate position.

Embodiment of FIGS. 39 and 40

In the embodiment of FIGS. 39 and 40, cannula 258 is inserted through a small incision to a position between upper and lower spinous processes. Once the cannula is properly inserted, an implant 260 is pushed through the cannula 258 using an insertion tool 262. The implant 260 includes a plurality of ribs or indentation 264 that assist in positioning the implant 260 relative to the upper and lower spinal processes. Once the implant 260 is in position, the cannula 258 is withdrawn so that the implant 260 comes in contact with and wedges between the spinous processes. The cannula 258 is somewhat conical in shape with the nose end 266 being somewhat smaller than the distal end 268 in order to effect the insertion of the cannula into the space between the spinous processes.

Further, a plurality of cannula can be used instead of one, with each cannula being slightly bigger than one before. In the method of the invention, the first smaller cannula would be inserted followed by successively larger cannula being placed over the previous smaller cannula. The smaller cannula would then be withdrawn from the center of the larger cannula. Once the largest cannula is in place, and the opening of the skin accordingly expanded, the implant, which is accommodated by only the larger cannula, is inserted through the larger cannula and into position.

Figure 43:
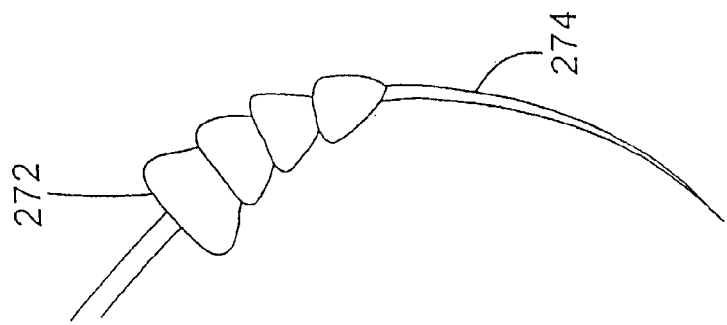
FIGS. 41, 42 and 43 depict yet further embodiments of an apparatus and method of the present invention.
Figure 42:
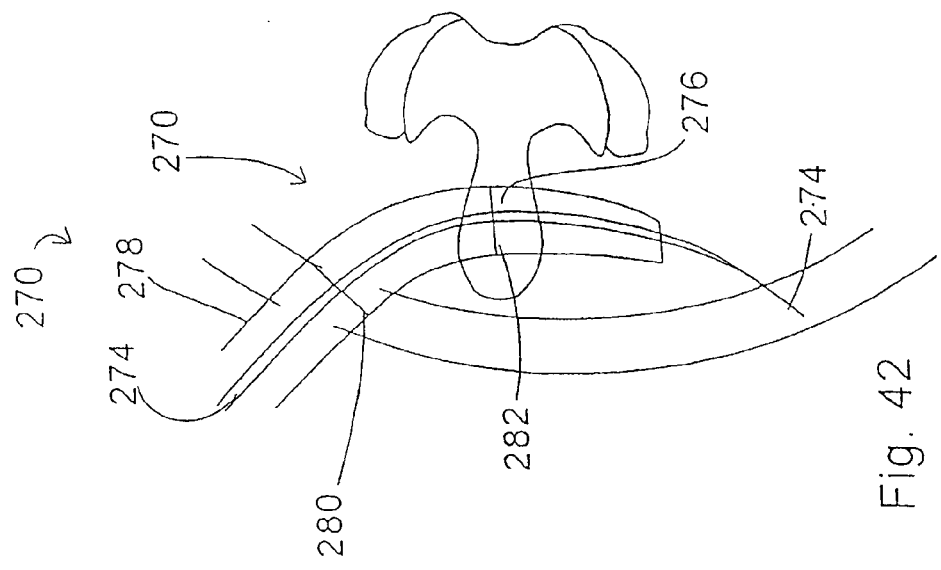
Figure 41:
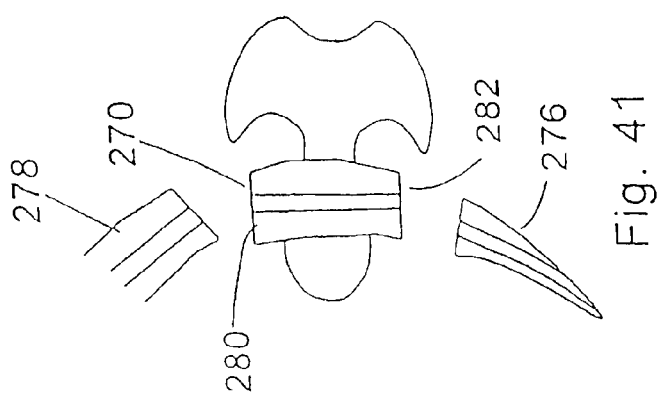

Embodiments of FIGS. 41, 42 and 43

The precurved implant 270 in FIGS. 41 and 42, and precurved implant 272 in FIG. 43 have common introduction techniques which includes a guide wire, guide tool, or stylet 274. For both embodiments, the guide wire 274 is appropriately positioned through the skin of the patient and into the space between the spinous processes. After this is accomplished, the implant is directed over the guide wire and into position between the spinous processes. The precurved nature of the implant assist in (1) positioning the implant through a first small incision in the patient's skin on one side of the space between two spinous processes and (2) guiding the implant toward a second small incision in the patient's skin on the other side of the space between the two spinous processes. With respect to the implant 270, the implant includes a conical introduction nose 276 and a distal portion 278. As the nose 276 is inserted between the spinous processes, this causes distraction of the spinous processes. Break lines 280, 282 are established at opposite sides of the implant 270. Once the implant is properly positioned over the guide wire between the spinous processes, the nose portion 276 and the distal portion 278 can be broken off along the break lines, through the above two incisions, in order to leave the implant 270 in position.

Although only two break lines 280, 282 are depicted, multiple break lines can be provided on implant 270 so that the implant can continue to be fed over the guide wire 278 until the appropriate width of the implant 270 creates the desired amount of distraction. As described hereinabove, the break lines can be created by perforating or otherwise weakening the implant 270 so that the appropriate portions can be snapped or sawed off.

With respect to the precurved implant 272, this implant is similar in design to the implant 230 shown in FIG. 36. This implant 272 in FIG. 47, however, is precurved and inserted over a guide wire 274 to a position between the spinous processes. As with implant 230 in FIG. 43, once the appropriate level of this distraction has been reached and if desired, sections of the implant 272 can be broken, snapped or sawed off as described hereinabove in order to leave a portion of the implant wedged between the upper and lower spinous processes.

Embodiment of FIG. 44

A further embodiment of the invention is shown in FIG. 44. This embodiment includes a combination insertion tool and implant 290. The insertion tool and implant 290 is in the shape of a ring which is hinged at point 292. The ring is formed by a first elongated and conically shaped member 294 and a second elongated and conically shaped member 296. Members 294 and 296 terminate in points and through the use of hinge 292 are aligned and meet. Through similar incisions on both sides of the spinous processes, first member and second member are inserted through the skins of the patient and are mated together between the spinous processes. After this has occurred, the implant 290 is rotated, for example clockwise, so that increasingly widening portions of the first member 292 are used to distract the first and second spinous processes. When the appropriate level of distraction has occurred, the remainder of the ring before and after the section which is located between the spinous processes can be broken off as taught hereinabove in order to maintain the desired distraction. Alternatively, with a small enough ring, the entire ring can be left in place with the spinous processes distracted.

Embodiment of FIG. 45

In FIG. 45, the implant 300 is comprised of a plurality of rods or stylets 302 which are inserted between the upper and lower spinous processes. The rods are designed much as described hereinabove so that they may be broken, snapped or cut off. Once these are inserted and the appropriate distraction has been reached, the stylets are broken off and a segment of each stylet remains in order to maintain distraction of the spinous process.

Embodiment of FIGS. 46 and 47

Implant 310 of FIGS. 46 and 47 is comprised of a shape memory material which coils upon being released. The material is straightened out in a delivery tool 312. The delivery tool is in position between upper and lower spinous processes 314, 316. The material is then pushed through the delivery tool. As it is released from the delivery end 318 of the delivery tool, the material coils, distracting the spinous processes to the desired amount. Once this distraction has been achieved, the material is cut and the delivery tool removed.

Embodiments of FIGS. 48, 49, 50 and 51

As can be seen in FIG. 48, the implant 320 is delivered between upper and lower spinous processes 322 and 324, by delivery tool 326. Once the implant 320 is in place between the spinous processes, the delivery tool is given a 90° twist so that the implant goes from the orientation as shown in FIG. 49, with longest dimension substantially perpendicular to the spinous processes, to the orientation shown in FIG. 50 where the longest dimension is in line with and parallel to the spinous processes. This rotation causes the desired distraction between the spinous processes. Implant 320 includes opposed recesses 321 and 323 located at the ends thereof. Rotation of the implant 320 causes the spinous processes to become lodged in these recesses.

Alternatively, the insertion tool 326 can be used to insert multiple implants 320, 321 into the space between the spinous processes 322, 324 (FIG. 51). Multiple implants 320, 321 can be inserted until the appropriate amount of distraction is built up. It is to be understood in this situation that one implant would lock to another implant by use of, for example, a channel arrangement wherein a projection from one of the implants would be received into and locked into a channel of the other implant. Such a channel arrangement is depicted with respect to the other embodiment.

Embodiment of FIGS. 52, 53, 54, 55a and 55b

The embodiment of FIGS. 52 through 55b is comprised of a fluid-filled dynamic distraction implant 350. This implant includes a membrane 352 which is placed over pre-bent insertion rod 354 and then inserted through an incision on one side of the spinous process 356. The bent insertion rod, with the implant 350 thereover, is guided between appropriate spinous processes. After this occurs, the insertion rod 354 is removed leaving the flexible implant in place. The implant 350 is then connected to a source of fluid (gas, liquid, gel and the like) and the fluid is forced into the implant causing it to expand as shown in FIG. 54, distracting the spinal processes to the desired amount. Once the desired amount of distraction has occurred, the implant 350 is closed off as is shown in FIG. 55a. The implant 350 being flexible, can mold to the spinous processes which may be of irregular shape, thus assuring positioning. Further, implant 350 acts as a shock absorber, damping forces and stresses between the implant and the spinous processes.

A variety of materials can be used to make the implant and the fluid which is forced into the implant. By way of example only, viscoelastic substances such as methylcellulose, or hyaluronic acid can be used to fill the implant. Further, materials which are initially a fluid, but later solidify, can be inserted in order to cause the necessary distraction. As the materials solidify, they mold into a custom shape about the spinous processes and accordingly are held in position at least with respect to one of two adjacent spinous processes. Thus, it can be appreciated that using this embodiment and appropriate insertion tools the implant can be formed about one spinous process in such a manner that the implant stays positioned with respect to that spinous process (FIG. 55b). With such an embodiment, a single implant can be used as an extension stop for spinous process located on either side, without restricting flexion of the spinal column.

It is to be understood that many of the other implants disclosed herein can be modified so that they receive a fluid in order to establish and maintain a desired distraction much in the manner as implant 350 receives a fluid.

Figure 58:
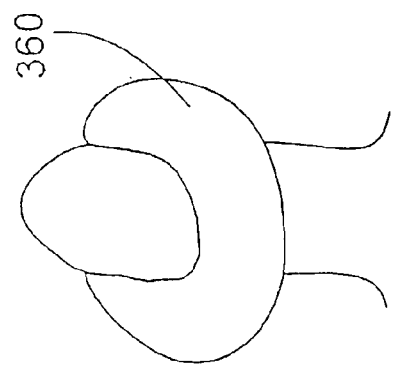
FIGS. 56, 57 and 58 depict yet a further apparatus and method of the invention.
Figure 57:
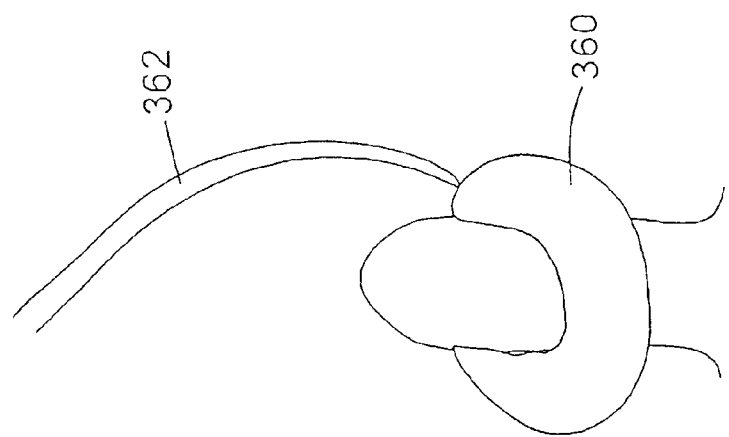
Figure 56:
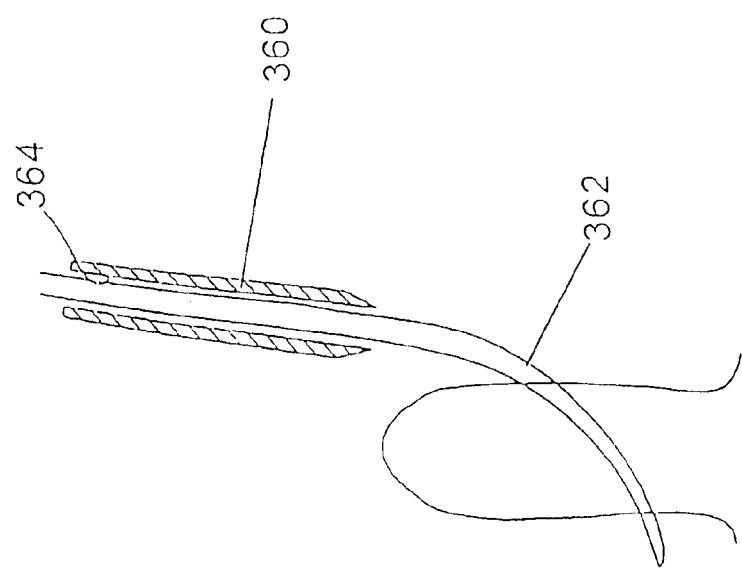

Embodiment of FIGS. 56, 57 and 58

The implant 360 as shown in FIG. 56 is comprised of a shape memory material such as a plastic or a metal. A curved introductory tool 362 is positioned between the appropriate spinous processes as described hereinabove. Once this has occurred, bore 364 of the implant is received over the tool. This act can cause the implant to straighten out. The implant is then urged into position and thereby distracts the spinous processes. When this has occurred, the insertion tool 362 is removed, allowing the implant to assume its pre-straightened configuration and is thereby secured about one of the spinous processes. Such an arrangement allows for an implant that is an extension stop and does not inhibit flexion of the spinous column. Alternatively, the implant can be temperature sensitive. That is to say that the implant would be more straightened initially, but become more curved when it was warmed by the temperature of the patient's body.

Embodiments of FIGS. 59 and 60

In this embodiment, the implant 380 is comprised of a plurality of interlocking leaves 382. Initially, a first leaf is positioned between opposed spinous processes 384, 386. Then subsequently, leafs 382 are interposed between the spinous processes until the desired distraction has been built up. The leaves are somewhat spring-like in order to absorb the shock and can somewhat conform to the spinous processes.

Embodiment of FIG. 61

The implant 390 of FIG. 61 includes the placement of shields 392, 394 over adjacent spinous processes 396, 398.

The shields are used to prevent damage to the spinous processes. These shields include apertures which receives a self-tapping screw 400, 402. In practice, the shields are affixed to the spinous processes and the spinous processes are distracted in the appropriate amount. Once this has occurred, a rod 404 is used to hold the distracted position by being screwed into each of the spinous processes through the aperture in the shields using the screws as depicted in FIG. 61.

Figure 62:
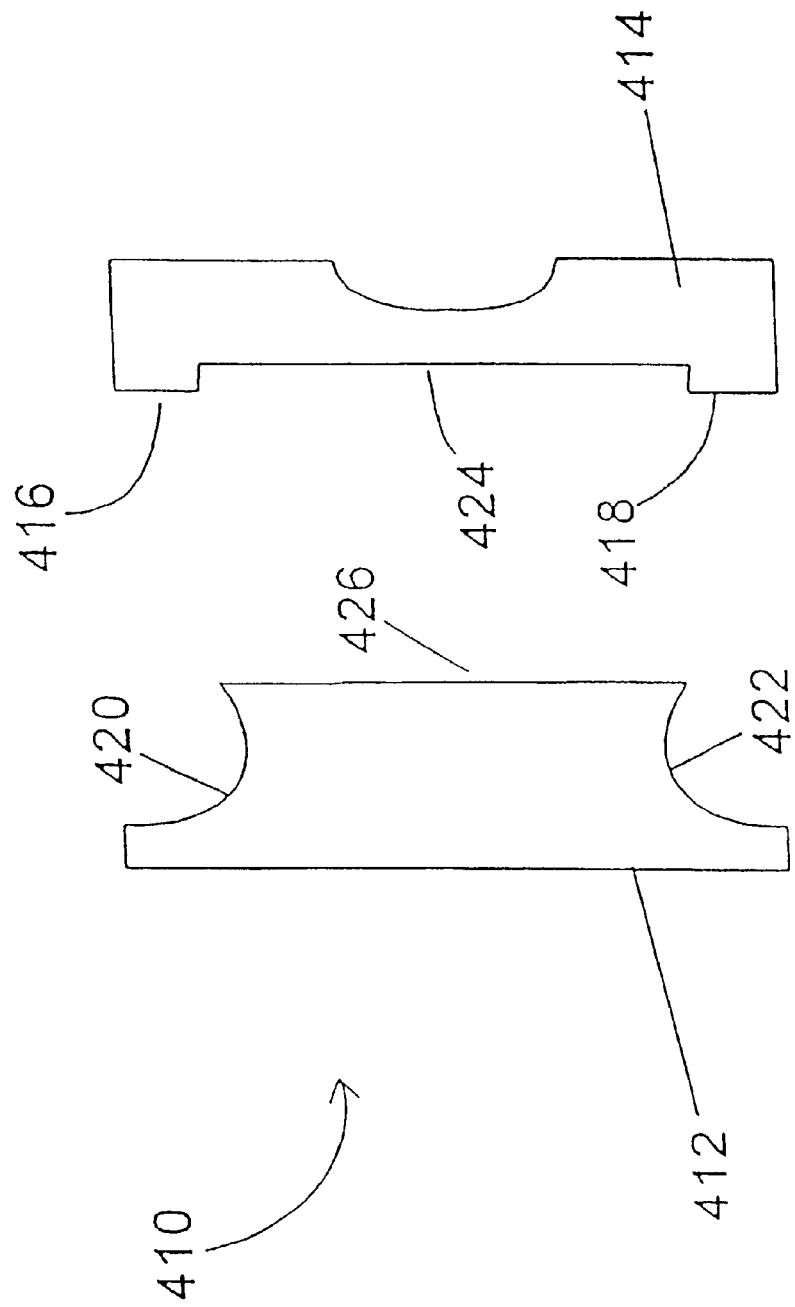

Embodiment of FIGS. 62 and 63

Figure 64:
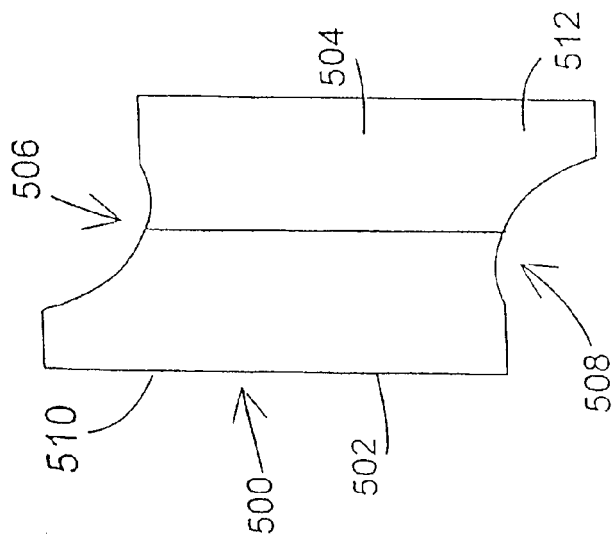

Implant 410 of FIGS. 62, 63 is comprised of first and second members 412, 414 which can be mated together using an appropriate screw and threaded bore arrangement to form the implant 410. Main member 412 and mating member 414 form implant 410. Accordingly, the implant 410 would have a plurality of members 414 for use with a standardized first member 412. FIGS. 62 and 64 show different types of mating members 414. In FIG. 62, the mating member 414 includes projections 416 and 418 which act like shims. These projections are used to project into the space of saddles 420, 422 of the first member 412. These projections 416, 418 can be of varying lengths in order to accommodate different sizes of spinous processes. A groove 424 is placed between the projections 416, 418 and mates with an extension 426 of the first member 412.

As shown in FIG. 63, the projections of the embodiment shown in FIG. 62 are removed and recesses 428, 430 are substituted therefor. These recesses expand the area of the saddles 420, 422 in order to accommodate larger spinous processes.

Figure 66:
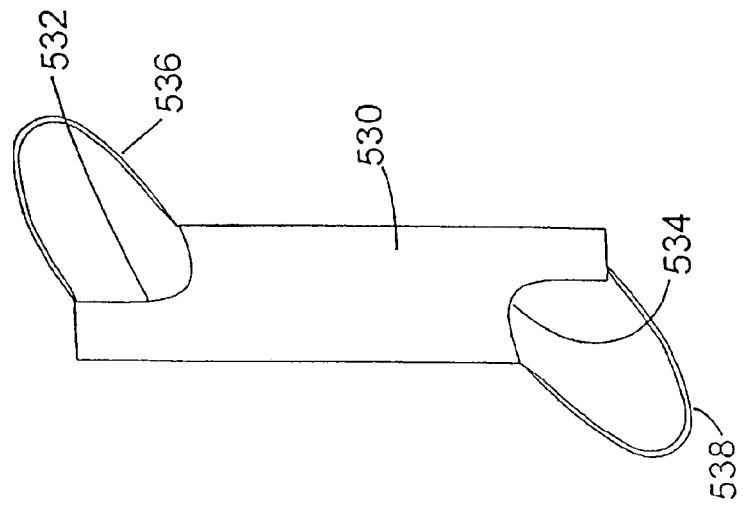
FIG. 66 depicts another embodiment of the invention.
Figure 65:
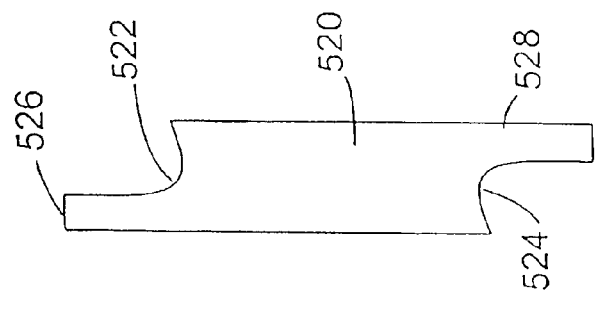
FIGS. 64 and 65 depict still a further embodiment of the present invention.

Embodiment of FIGS. 64, 65 and 66

The embodiments of FIGS. 64, 65 and 66 are similar in design and concept to the embodiment of FIGS. 62 and 63. In FIG. 64, the implant 500 includes the first and second members 502, 504. These members can be secured together with appropriate screws or other fastening means as taught in other embodiments. Implant 500 includes first and second saddles 506, 508 which are formed between the ends of first and second members 502, 504. These saddles 506, 508 are used to receive and cradle the adjacent spinous processes. As can be seen in FIG. 64, each saddle 506, 508 is defined by a single projection or leg 510, 512, which extends from the appropriate first and second members 502, 504. Unlike the embodiment found in FIGS. 62 and 63, each of the saddles is defined by only a single leg as the ligaments and other tissues associated with the spinous processes can be used to ensure that the implant is held in an appropriate position. With the configuration of FIG. 64, it is easier to position the implant relative to the spinous processes as each saddle is defined by only a single leg and thus the first and second members can be more easily worked into position between the various tissues.

In the embodiment of FIG. 65, the implant 520 is comprised of a single piece having saddles 522 and 524. The saddles are defined by a single leg 526, 528 respectively. In order for this implant 520 to be positioned between the spinous processes, an incision is made between lateral sides of adjacent spinous processes. The single leg 526 is directed through the incision to a position adjacent to an opposite lateral side of the spinous process with the spinous process cradled in the saddle 522. The spinous processes are then urged apart until saddle 524 can be pivoted into position into engagement with the other spinous process in order to maintain the distraction between the two adjacent spinous processes.

The embodiment of FIG. 66 is similar to that of FIG. 65 with an implant 530 and first and second saddles 532 and 534. Associated with each saddle is a tether 536, 538 respectively. The tethers are made of flexible materials known in the trade and industry and are positioned through bores in the implant 530. Once appropriately positioned, the tethers can be tied off. It is to be understood that the tethers are not meant to be used to immobilize one spinous process relative to the other, but are used to guide motion of the spinous processes relative to each other so that the implant 530 can be used as an extension stop and a flexion non-inhibitor. In other words, the saddles 532, 534 are used to stop spinal column backward bending and extension. However, the tethers do not inhibit forward bending and spinal column flexion.

Figure 68:
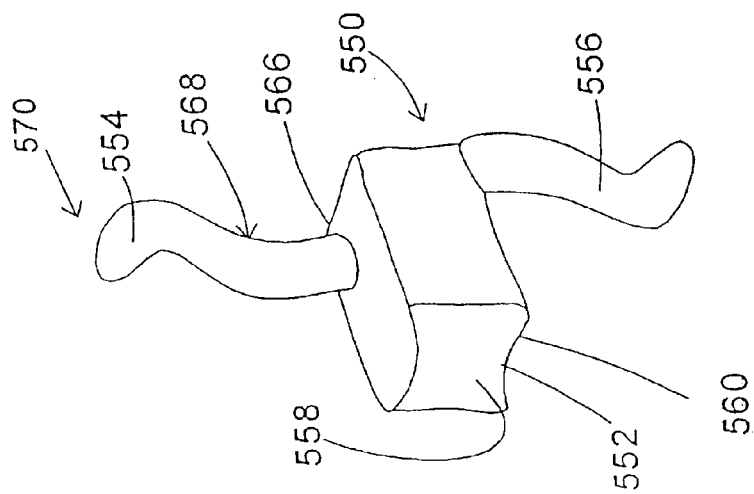
FIGS. 67 and 68 depict yet another embodiment of the present invention.
Figure 67:
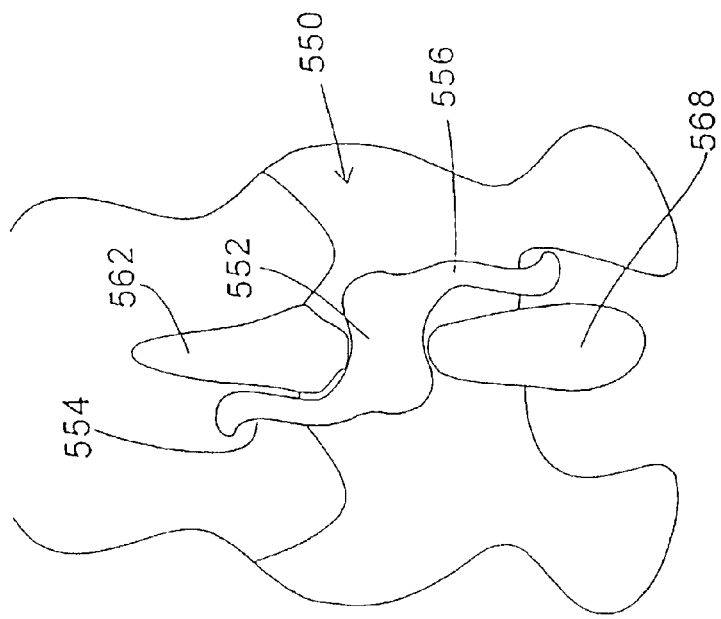

Embodiments of FIGS. 67, 68

The implant 550 is Z-shaped and includes a central body 552 and first and second arms 554, 556, extending in opposite directions therefrom. The central body 552 of the implant 550 includes first and second saddles 558 and 560. The first and second saddles 558 and 560 would receive upper and lower spinous processes 562, 568. The arms 554, 556 are accordingly located adjacent the distal end 566 (FIG. 68) of the central body 552. The first and second arms 554, 556, act to inhibit forward movement, migration or slippage of the implant 550 toward the spinal canal and keep the implant in place relative to the first and second spinal processes. This prevents the implant from pressing down on the ligamentum flavum and the dura. In a preferred embodiment, the central body would have a height of about 10 mm with each of the arms 554, 556 have a height of also about 10 mm. Depending on the patient, the height of the body could vary from about less than 10 mm to about greater than 24 mm. As can be seen in FIGS. 67 and 68, the first and second arms 554, 556 are additionally contoured in order to accept the upper and lower spinous processes 556, 558. In particular, the arms 554, 556 as can be seen with respect to arm 554 have a slightly outwardly bowed portion 568 (FIG. 68) with a distal end 570 which is slightly inwardly bowed. This configuration allows the arm to fit about the spinous process with the distal end 570 somewhat urged against the spinous process in order to guide the motion of the spinous process relative to the implant. These arms 554, 556 could if desired to be made more flexible than the central body 552 by making arms 554, 556 thin and/or with perforations, and/or other material different than that of the central body 550. As with the last embodiment, this embodiment can be urged into position between adjacent spinous processes by directing an arm into a lateral incision so that the central body 552 can be finally positioned between spinous processes.

Embodiment of FIGS. 69, 70, 71 and 71a

Figure 71:
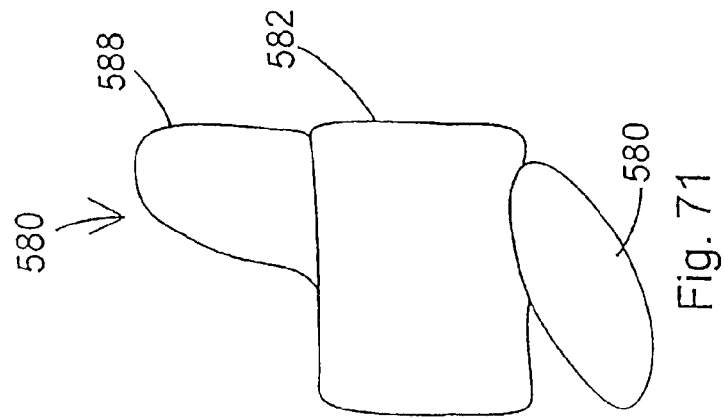
FIGS. 69, 70, 71 and 71a depict a further embodiment of the present invention.
Figure 70:
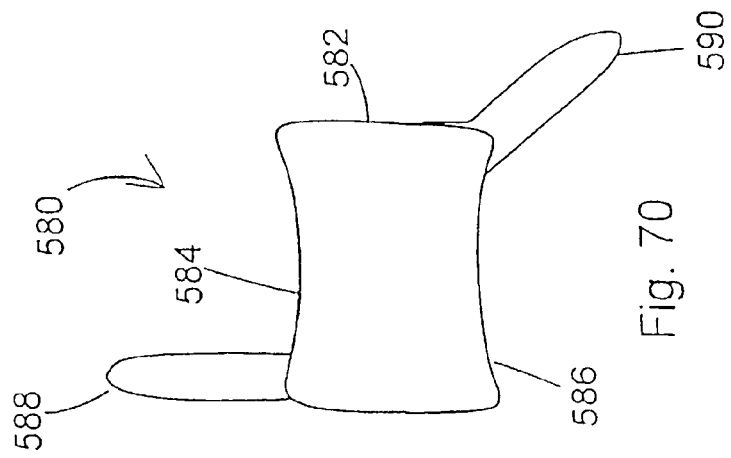
Figure 69:
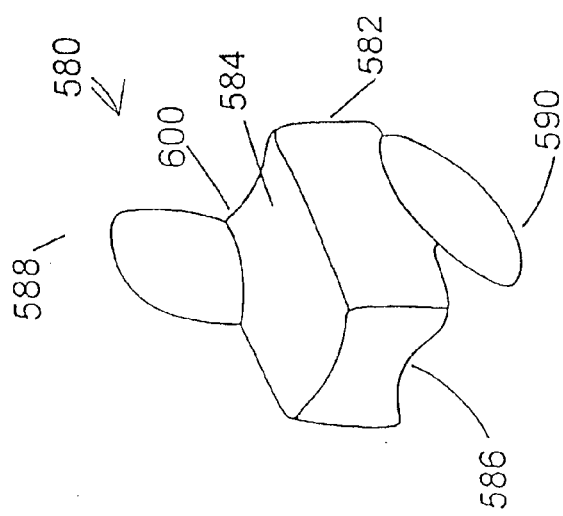

FIGS. 69, 70 and 71 are perspective front, end, and side views of implant 580 of the invention. This implant includes a central body 582 which has first and second saddles 584, 586 for receiving adjacent spinous processes. Additionally, the implant 580 includes first and second arms 588 and 590. The arms, as with the past embodiment, prevent forward migration or slippage of the implant toward the spinal canal. First arm 588 projects outwardly from the first saddle 584 and second arm 590 projects outwardly from the second saddle 586. In a preferred embodiment, the first arm 588 is located adjacent to the distal end 600 of the central body 582 and proceeds only partly along the length of the central body 582. The first arm 588 is substantially perpendicular to the central body as shown in FIG. 70. Further, the first arm 588, as well as the second arm 590, is anatomically rounded.

The second arm 590, projecting from second saddle 586, is located somewhat rearward of the distal end 600, and extends partially along the length of the central body 582. The second arm 590 projects at a compound angle from the central body 582. As can be seen in FIGS. 70 and 71, the second arm 590 is shown to be at about an angle of 45° from the saddle 586 (FIG. 70). Additionally, the second arm 590 is at an angle of about 45° relative to the length of the central body 580 as shown in FIG. 71. It is to be understood that other compound angles are within the spirit and scope of the invention as claimed.

In a preferred embodiment, the first and second arms 588, 590 have a length which is about the same as the width of the central body 582. Preferably, the length of each arm is about 10 mm and the width of the central body is about 10 mm. However, the bodies with the widths of 24 mm and greater are within the spirit and scope of the invention, along with first and second arms ranging from about 10 mm to greater than about 24 mm. Further, it is contemplated that the embodiment could include a central body having a width of about or greater than 24 mm with arms being at about 10 mm.

It is to be understood that the embodiment of FIGS. 69, 70 and 71 as well as the embodiment of FIGS. 67 and 68 are designed to preferably be positioned between the L4-L5 and the L5-S1 vertebral pairs. The embodiment of FIGS. 69, 70, 71 is particularly designed for the L5-S1 position with the arms being designed to conform to the sloping surfaces found therebetween. The first and second arms are thus contoured so that they lie flat against the lamina of the vertebra which has a slight angle.

The embodiment of FIGS. 69, 70, and 71 as with the embodiment of FIGS. 67 and 68 is Z-shaped in configuration so that it may be inserted from one lateral side to a position between adjacent spinous processes. A first arm, followed by the central body, is guided through the space between the spinous processes. Such an arrangement only requires that a incision on one side of the spinous process be made in order to successfully implant the device between the two spinous processes.

Figure 71A:
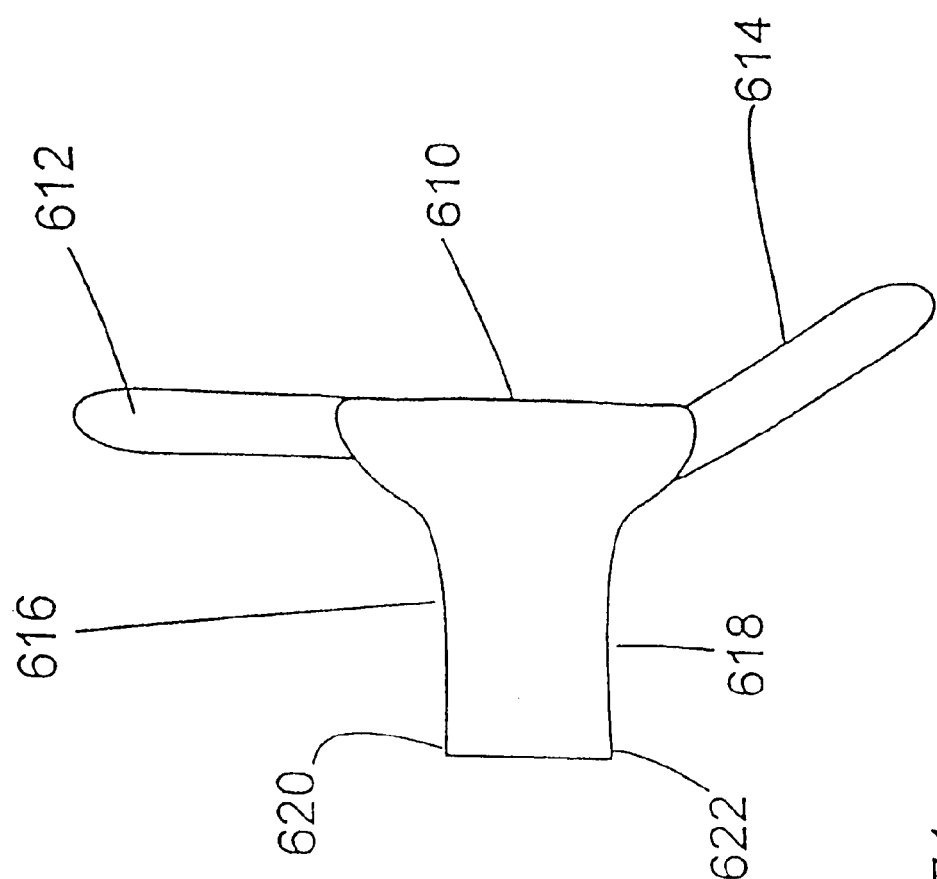

The implant 610 of FIG. 71a is similar to that immediately above with the first arm 612 located on the same side of the implant as the second arm 614. The first and second saddle 616, 618 are slightly modified in that distal portion 620, 622 are somewhat flattened from the normal saddle shape in order to allow the implant to be positioned between the spinous processes from one side. Once in position, the ligaments and tissues associated with the spinous processes would hold the implant into position. Tethers also could be used if desired.

Figure 72:
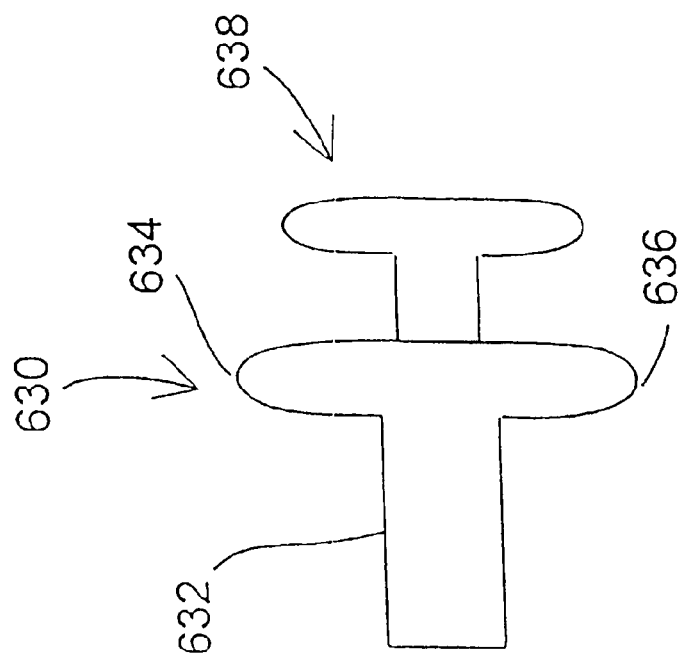
FIGS. 72 and 73 depict still another embodiment of the invention.
Figure 73:
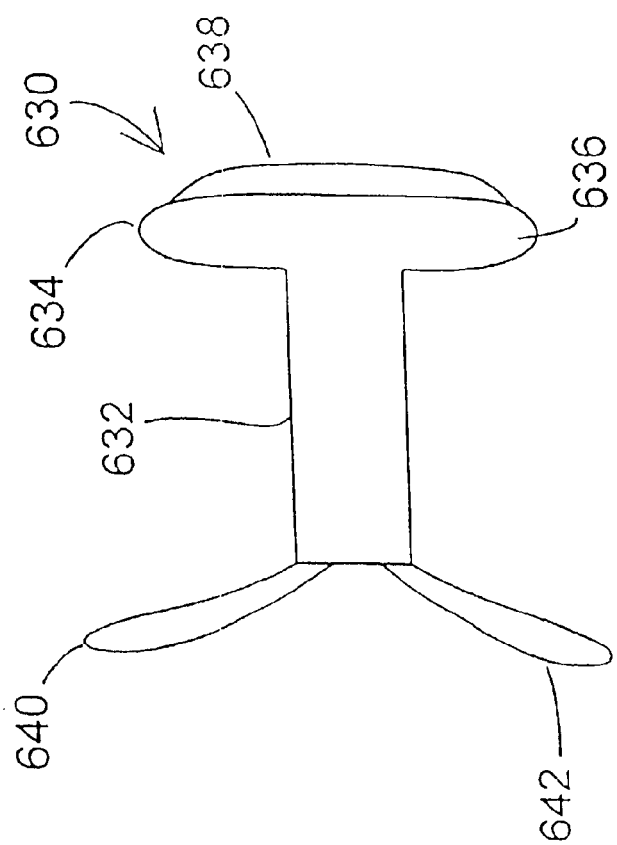

Embodiment of FIGS. 72, 73

Implant 630 is also designed so that it can be inserted from one side of adjacent spinous processes. This insert 630 includes a central body 632 with the first and second arms 634, 636 extending on either side thereof. As can be seen in FIG. 72, a plunger 638 is positioned to extend from an end of the central body 632. As shown in FIG. 72, the plunger 638 is fully extended and as shown in FIG. 73, the plunger 638 is received within the central body 632 of the implant 630. With the plunger received into the implant 632, the third and fourth arms or hooks 640, 642 can extend outwardly from the central body 632. The third and fourth arms or hooks 640, 642 can be comprised of a variety of materials, such as for example, shape memory metal materials or materials which have a springy quality.

For purposes of positioning the implant 630 between adjacent spinous processes, the plunger 638 is pulled outwardly as shown in FIG. 72. The central body 632 is then positioned between adjacent spinous processes and the plunger 638 is allowed to move to the position of FIG. 73 so that the third and fourth arms 640, 642 can project outwardly from the central body 632 in order to hold the implant 630 in position between the spinous processes.

Plunger 638 can be spring biased to the position as shown in FIG. 73 or can include detents or other mechanisms which lock it into that position. Further, the third and fourth arms themselves, as deployed, can keep the plunger in the position as shown in FIG. 73.

Embodiments of FIGS. 74, 75, 76, 77, and 78

Figure 74:
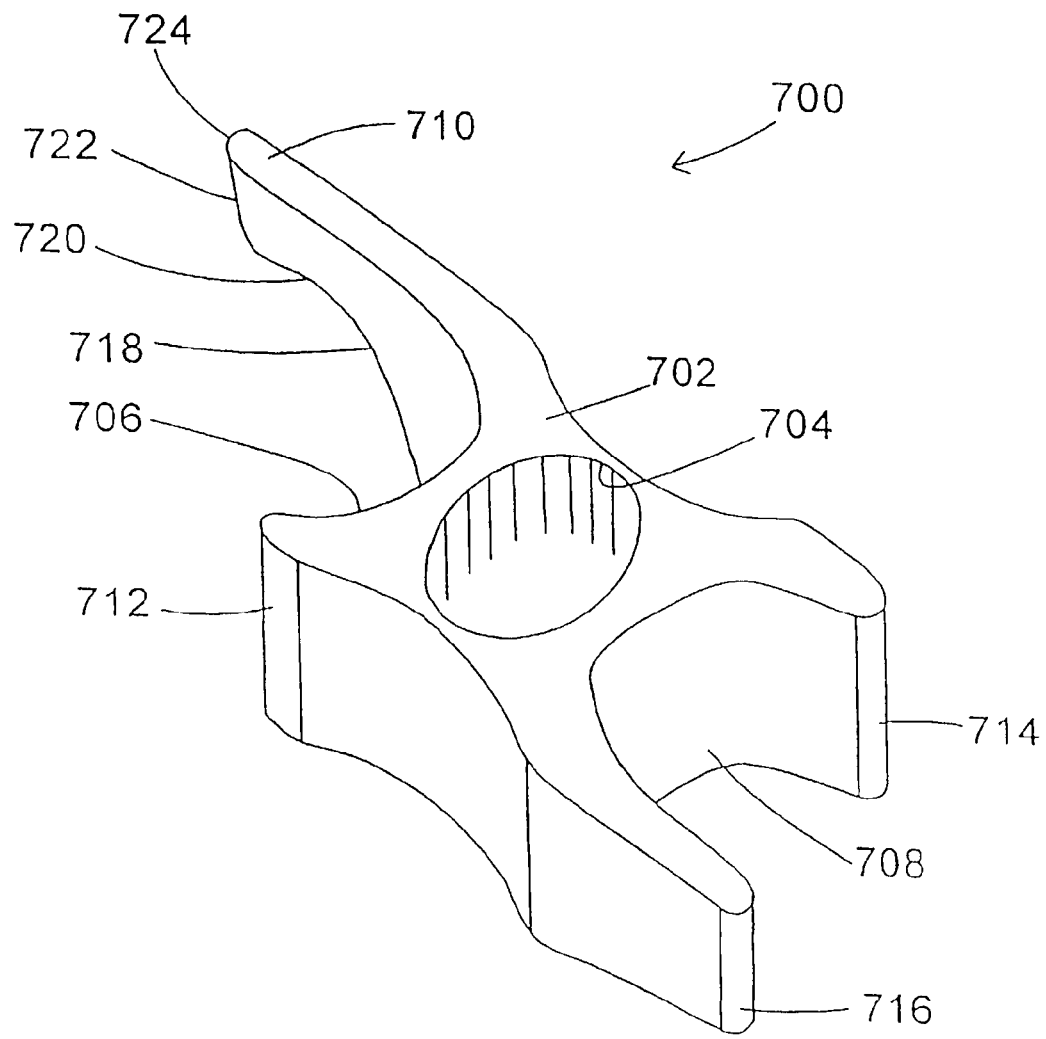
FIGS. 74, 75, 76, 77, and 78 depict still other embodiments of the invention.
Figure 75:
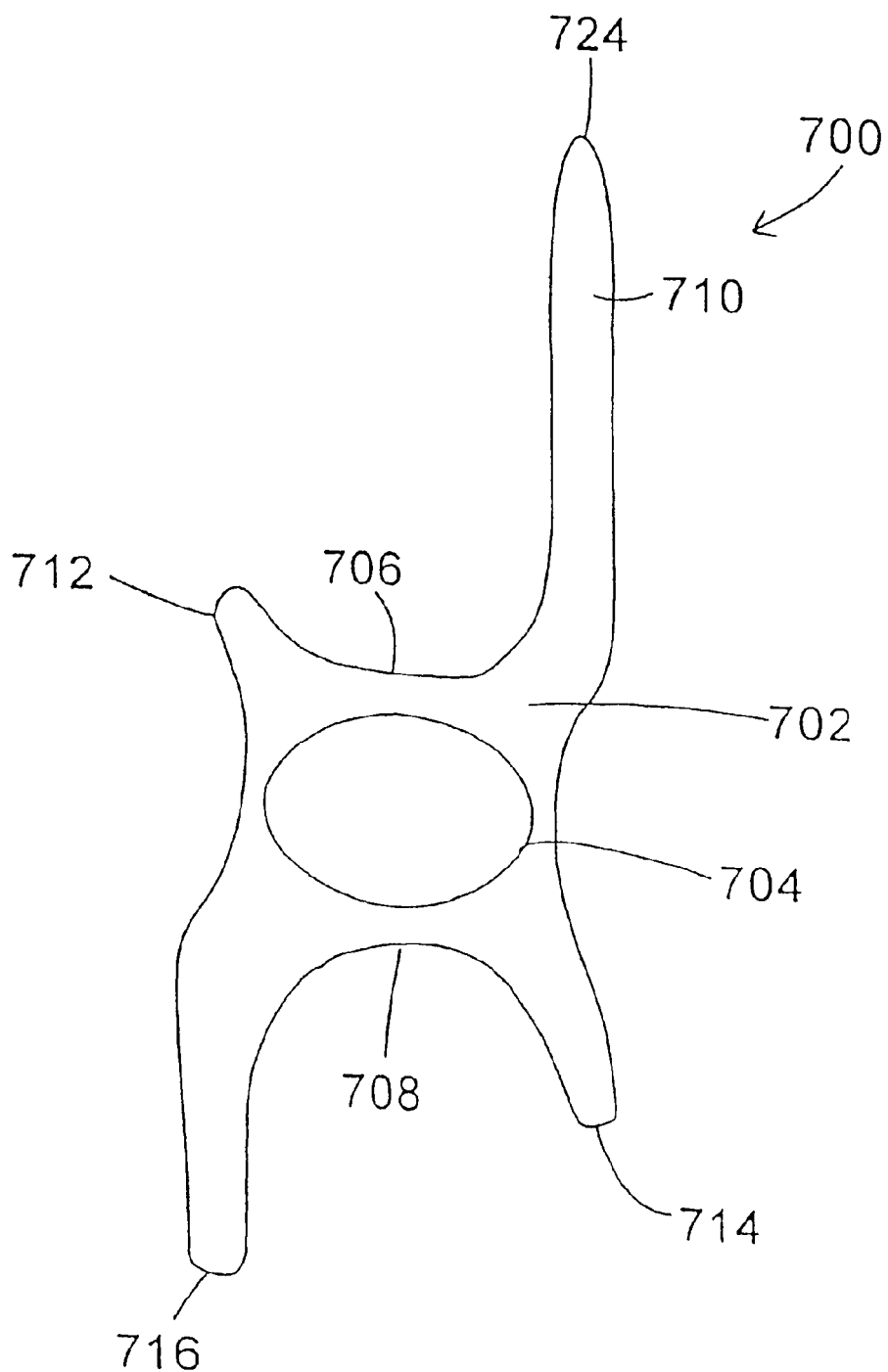
Figure 76:
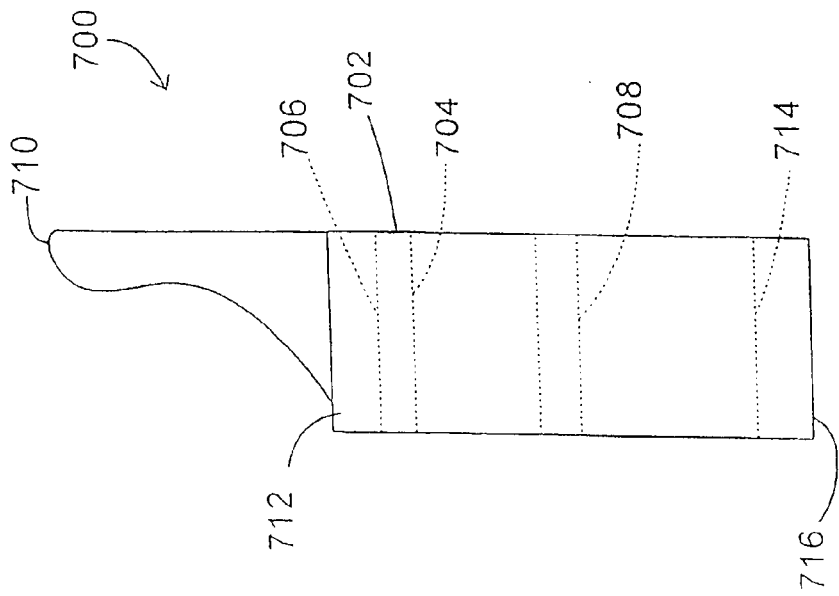

Other embodiments of the invention are shown in FIGS. 74 through 78. FIGS. 74, 75 and 76 disclose implant 700. Implant 700 is particularly suited for implantation between the L4-L5 and L5-S1 vertebra. As can be seen in FIG. 74, the implant 700 includes a central body 702 which has a bore 704 provided therein. Bore 704 is used in order to adjust the modulus of elasticity of the implant so that it is preferably approximately two times the anatomical load placed on the vertebra in extension. In other words, the implant 700 is approximately two times stiffer than the normal load placed on the implant. Such an arrangement is made in order to ensure that the implant is somewhat flexible in order to reduce potential resorption of the bone adjacent to the implant. Other modulus values can be used and be within the spirit of the invention.

Implant 700 includes first and second saddle 706, 708 which are used to receive and spread the load from the upper and lower spinous processes. The saddle 706 is defined by first and second arms 710 and 712. The second saddle 708 is defined by third and fourth arms 714 and 716. As can be seen in FIG. 74, the first arm 710, in a preferred embodiment, is approximately two times the length of the body 702 with the second arm being approximately less than a quarter length of the body. Third arm 714 is approximately one times the length of the body 702 with the fourth arm 716 being, in this preferred embodiment, approximately one and a half times the length of the body 702. The arms are designed in such a way that the implant (1) can be easily and conveniently inserted between the adjacent spinous processes, (2) will not migrate forwardly toward the spinal canal, and (3) will hold its position through flexion and extension as well as lateral bending of the spinal column.

Figure 77:
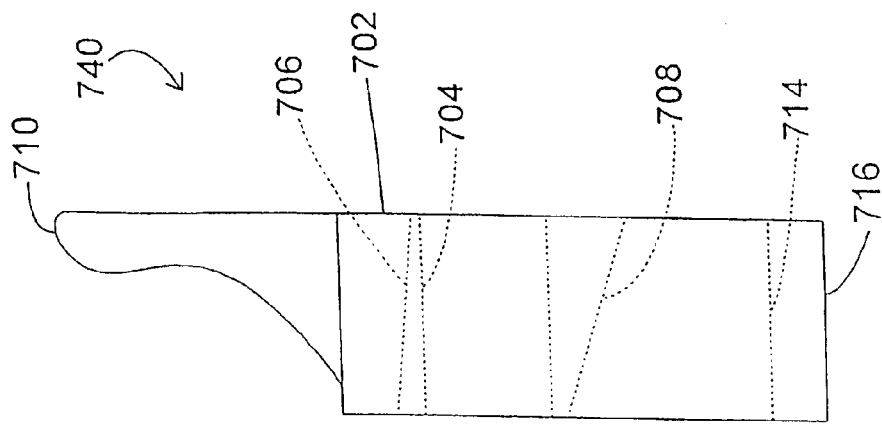
Figure 78:
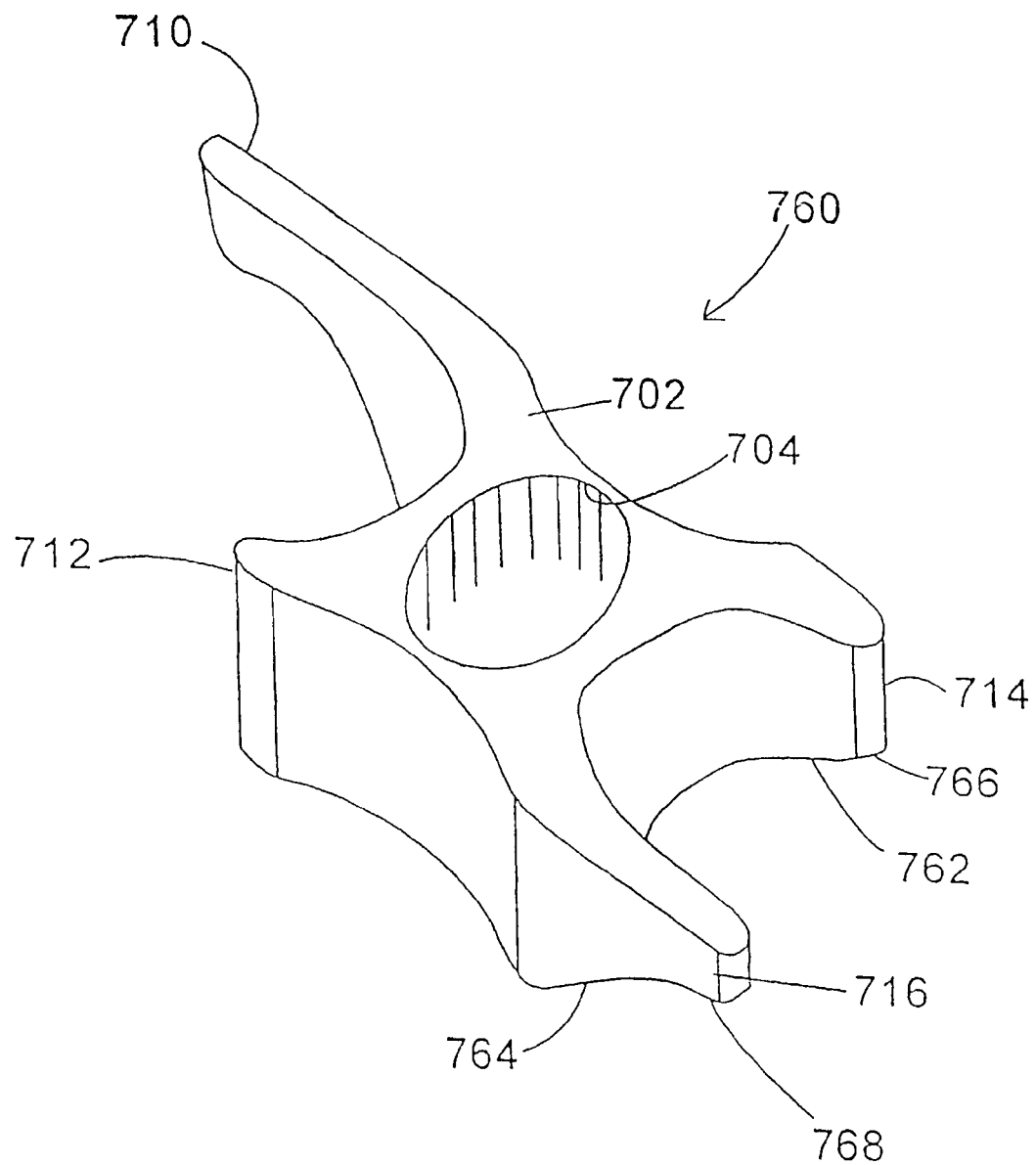
Figure 81:
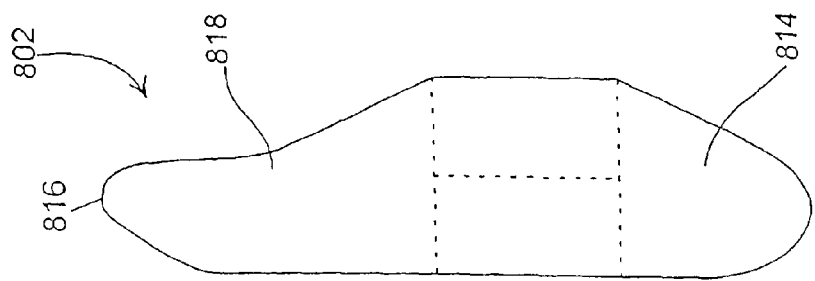

First arm 710 is in addition designed to accommodate the shape of the vertebra. As can be seen in FIG. 74, the first arm 710 becomes narrower as it extends away from the body 702. The first arm 710 includes a sloping portion 718 followed by a small recess 720 ending in a rounded portion 722 adjacent to the end 724. This design is provided to accommodate the anatomical form of for example the L4 vertebra. It is to be understood that these vertebra have a number of surfaces at roughly 30° angles and that the sloping surfaces of this embodiment and the embodiments shown in FIGS. 77 and 78 are designed to accommodate these surfaces. These embodiments can be further modified in order to accommodate other angles and shapes.

The second arm 712 is small so that it is easy to insert between the spinous processes, yet still define the saddle 706. The fourth arm 716 is larger than the third arm 714, both of which are smaller than the first arm 710. The third and fourth arms are designed so that they define the saddle 706, guide the spinous processes relative to the implant 700 during movement of the spinal column, and yet are of a size which makes the implant easy to position between the spinous processes.

The procedure, by way of example only, for implanting the implant 700 can be to make an incision laterally between two spinous processes and then initially insert first arm 710 between the spinous processes. The implant and/or appropriate tools would be used to distract the spinous processes allowing the third leg 714 and the central body 702 to fit through the space between the spinous processes. The third leg 714 would then come to rest adjacent the lower spinous processes on the opposite side with the spinous processes resting in the first and second saddle 706, 708. The longer fourth leg 716 would then assist in the positioning of the implant 700.

FIG. 77 includes an implant 740 which is similar to implant 700 and thus have similar numbering. The saddle 706, 708 of implant 740 have been cantered or sloped in order to accommodate the bone structure between, by way of example, the L4-L5 and the L5-S1 vertebra. As indicated above, the vertebra in this area have a number of sloping surfaces in the range of about 30°. Accordingly, saddle 706 is sloped at less than 30° and preferably about 20° while saddle 708 is sloped at about 30° and preferably more than 30°.

The implant 760 as shown in FIG. 78 is similar to implant 700 in FIG. 74 and is similarly numbered. Implant 760 includes third and fourth legs 714, 716 which have sloping portions 762, 764 which slope toward ends 766, 768 of third and fourth arm 714, 716 respectively. The sloping portions accommodate the form of the lower vertebra against which they are positioned. In the preferred embodiment, the sloping portions are of about 30°. However, it is to be understood that sloping portions which are substantially greater and substantially less than 30° can be included and be within the spirit and scope of the invention.

Embodiment of FIGS. 79, 80, 80a, 81, 82, 83, 83a, 84, 85, 86 and 87

Figure 80:
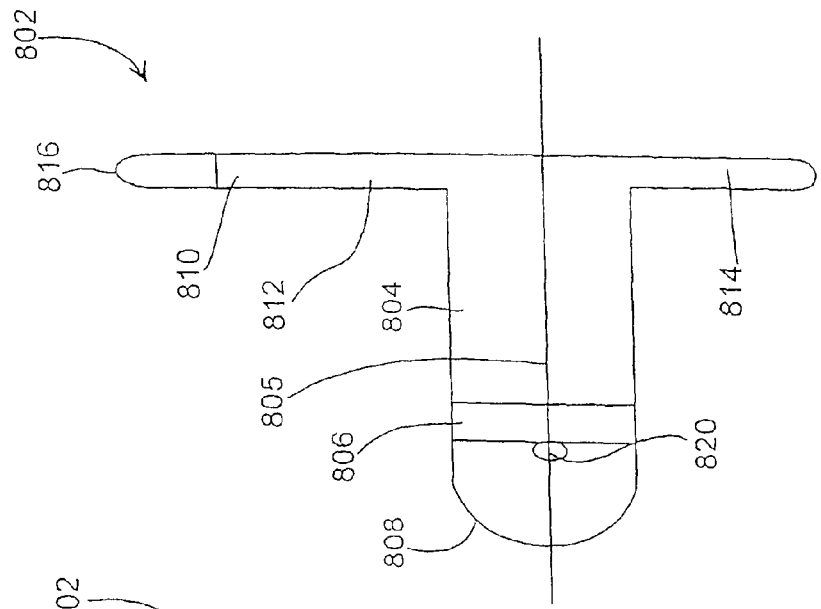
Figure 79:
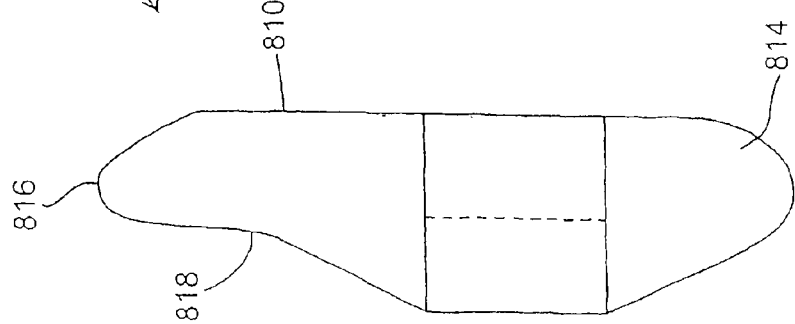
Figure 86:
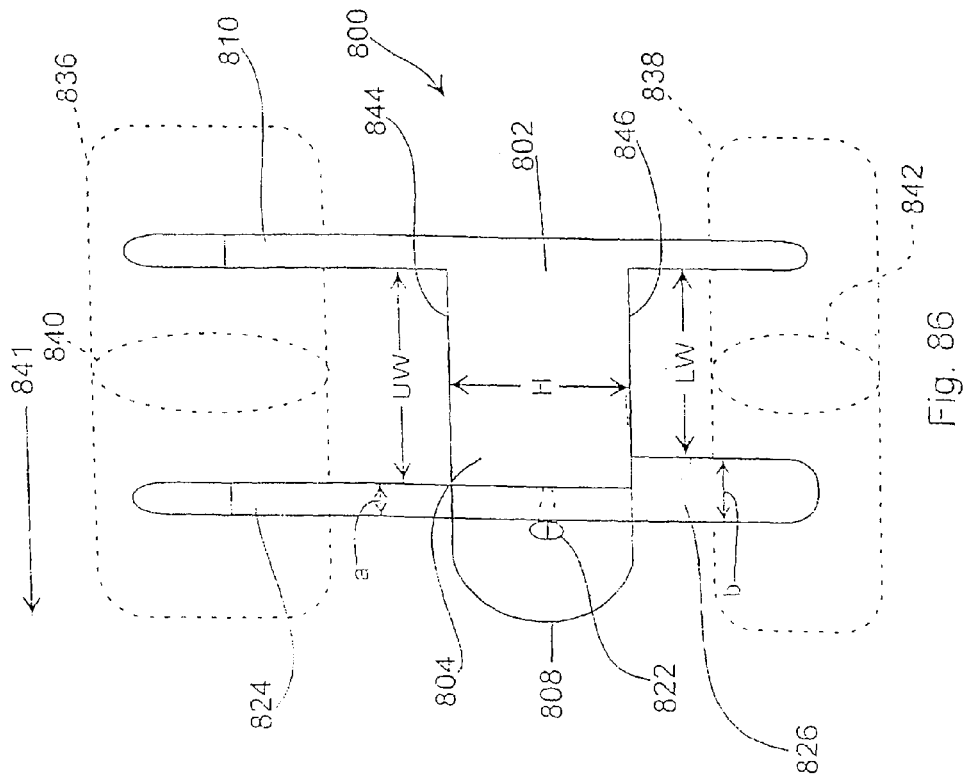
Figure 83A:
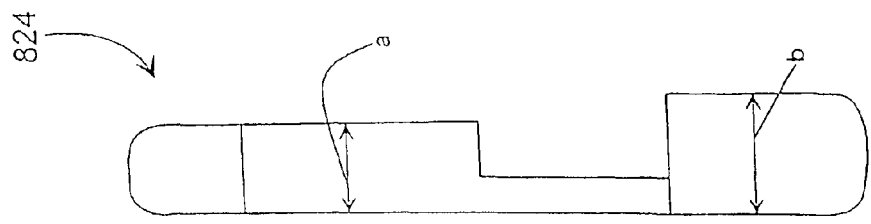
Figure 83:
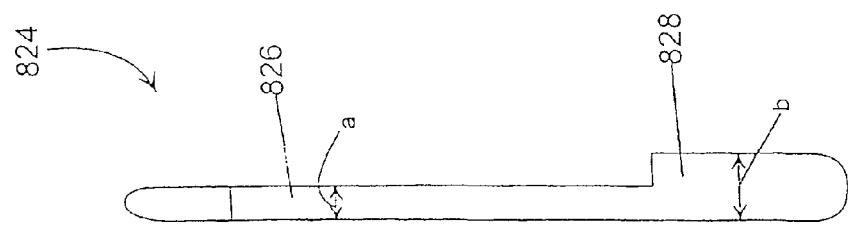
Figure 84:
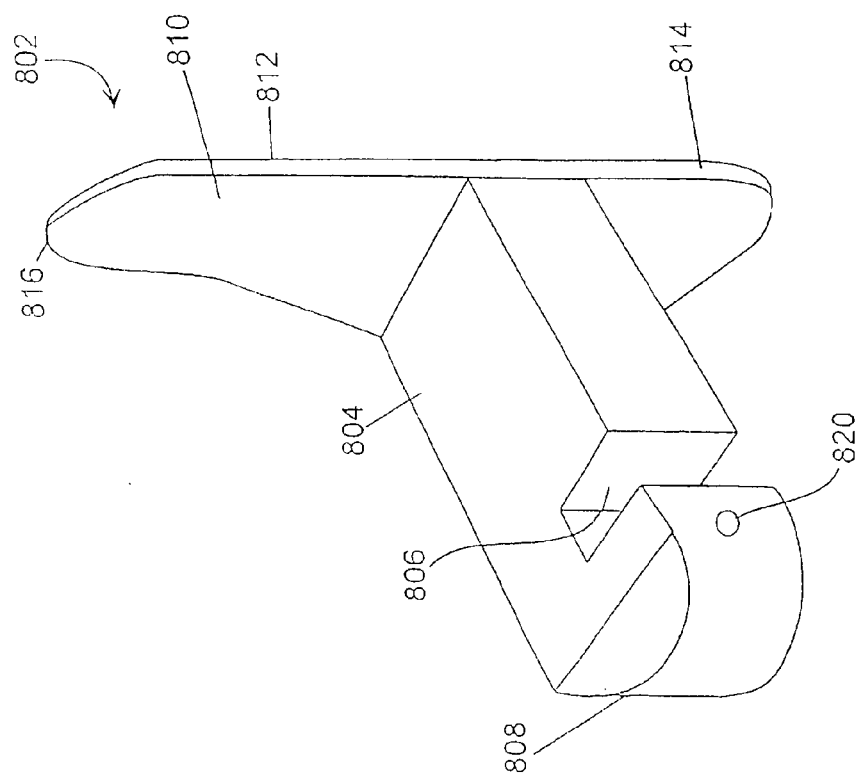
Figure 91:
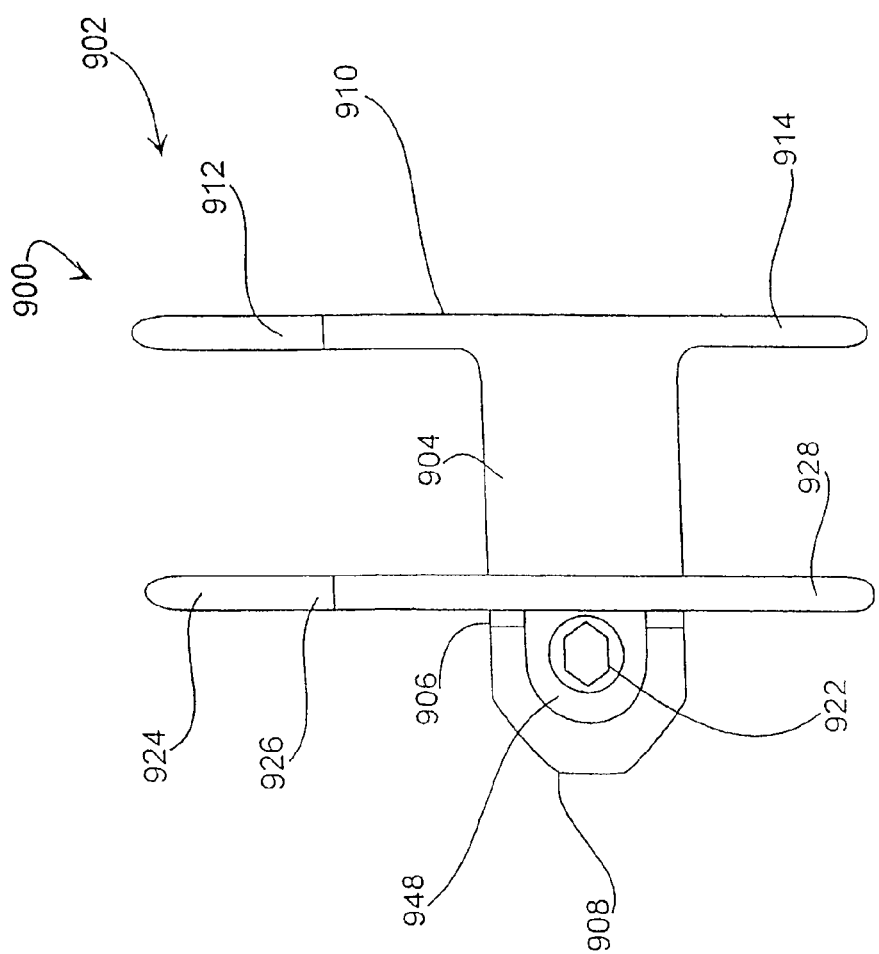

Another embodiment of the invention is shown in FIGS. 79-87 and includes implant 800 (FIG. 86). Implant 800 includes a distracting unit 802 which is shown in left side, plan, and right side views of FIGS. 79, 80 and 81. A perspective view of the distraction unit is shown in FIG. 84. The distracting unit as can be seen in FIG. 80 includes a distracting body 804, with longitudinal axis 805, which body 804 has a groove 806 and a rounded or bulbous end 808 which assist in the placement of the distracting body between adjacent spinous process so that an appropriate amount of distraction can be accomplished. Extending from the distracting body 804 is a first wing 810 which in FIG. 80 is substantially perpendicular to the distracting body 804. Such wings which are not perpendicular to the body are within the spirit and scope of the invention. First wing 810 includes a upper portion 812 and a lower portion 814. The upper portion 810 (FIG. 79) includes a rounded end 816 and a small recess 818. The rounded end 816 and the small recess 818 in the preferred embodiment are designed to accommodate the anatomical form or contour of the L4 (for a L4-L5 placement) or L5 (for a L5-S1 placement) superior lamina of the vertebra. It is to be understood that the same shape or variations of this shape can be used to accommodate other lamina of any vertebra. The lower portion 814 is also rounded in order to accommodate in the preferred embodiment in order to accommodate the vertebrae. The distracting unit further includes a threaded bore 820 which in this embodiment accepts a set screw 822 (FIG. 86) in order to hold a second wing 824 (FIGS. 82, 83) in position as will be discussed hereinbelow.

The threaded bore 820 in this embodiment slopes at approximately 45° angle and intersects the slot 806. With the second wing 824 in position, the set screw 822 when it is positioned in the threaded bore 820 can engage and hold the second wing 824 in position in the slot 806.

Figure 82:
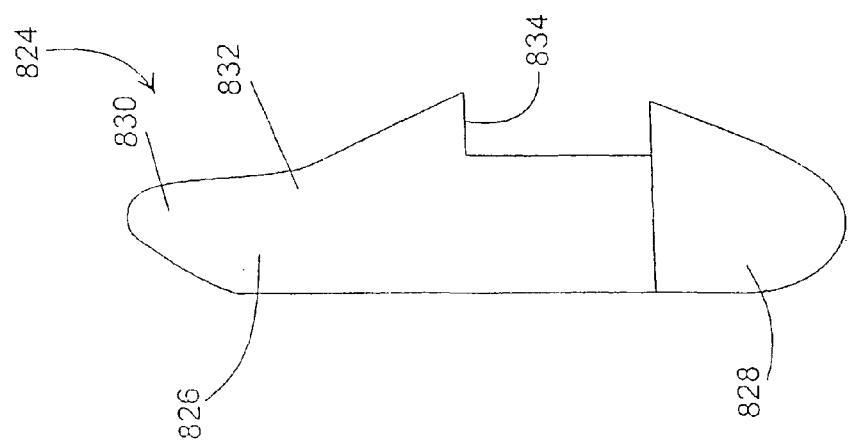
Figure 85:
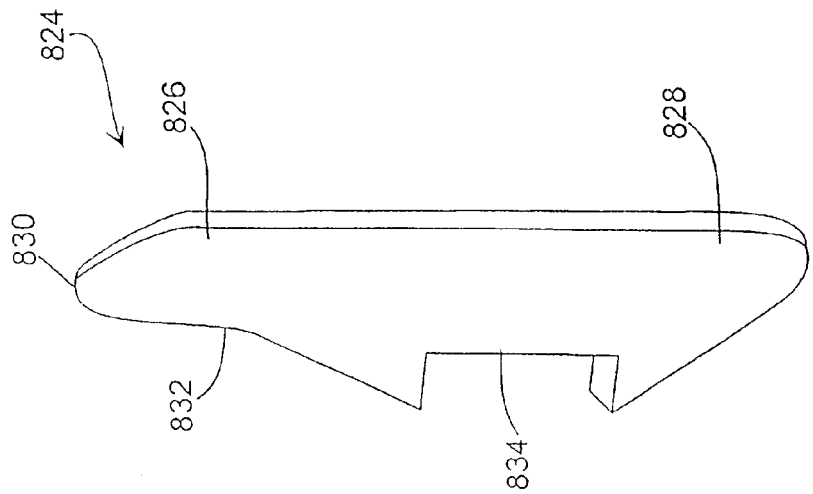

Turning to FIGS. 82, 83 and 85, left side, plan and perspective views of the second wing 824 are depicted. The second wing 824 is similar in design to the first wing. The second wing includes an upper portion 826 and a lower portion 828. The upper portion includes a rounded end 830 and a small recess 832. In addition, the second wing 824 includes a slot 834 which mates with the slot 806 of the distracting unit 802. The second wing 824 is the retaining unit of the present embodiment.

As can be seen in FIGS. 83 and 86, the second wing or retaining unit 824 includes the upper portion 826 having a first width "a" and the lower portion 828 having a second width "b". In the preferred embodiment, the second width "b" is larger than first width "a" due to the anatomical form or contour of the L4-L5 or L5-S1 laminae. As can be seen in FIG. 83a in second wing or retaining unit 824, the widths "a" and "b" would be increased in order to, as described hereinbelow, accommodate spinous processes and other anatomical forms or contours which are of different dimensions. Further, as appropriate, width "a" can be larger than width "b". Thus, as will be described more fully hereinbelow, the implant can include a universally-shaped distracting unit 802 with a plurality of retaining units 824, with each of the retaining units having different widths "a" and "b". During surgery, the appropriately sized retaining unit 824, width with the appropriate dimensions "a" and "b" can be selected to match to the anatomical form of the patient.

FIG. 86 depicts an assembled implant 800 positioned adjacent to upper and lower laminae 836, 838 (which are shown in dotted lines) of the upper and lower vertebrae. The vertebrae 836, 838 are essentially below the implant 800 as shown in FIG. 86. Extending upwardly from the vertebrae 836, 838, and between the first and second wings 810, 824, are the upper and lower spinous processes 840, 842. It is to be understood that in a preferred embodiment, the fit of the implant between the spinous processes can be such that the wings do not touch the spinous processes, as shown in FIG. 86, and be within the spirit and scope of the invention.

The implant 800 includes, as assembled, an upper saddle 844 and the lower saddle 846. The upper saddle 844 has an upper width identified by the dimension "UW". The lower saddle 846 has a lower width identified by the dimension "LW". In a preferred embodiment, the upper width is greater than the lower width. In other embodiments, the "UW" can be smaller than the "LW" depending on the anatomical requirements. The height between the upper and lower saddles 844, 846 is identified by the letter "h". These dimensions are carried over into FIG. 87 which is a schematic representation of the substantially trapezoidal shape which is formed between the upper and lower saddles. The table below gives sets of dimensions for the upper width, lower width, and height as shown in FIG. 87. This table includes dimensions for some variations of this embodiment.

| Variation | 1 | 2 | 3 |
|---|---|---|---|
| Upper Width | 8 | 7 | 6 |
| Lower Width | 7 | 6 | 5 |
| Height | 10 | 9 | 8 |

For the above table, all dimensions are given in millimeters.

For purposes of surgical implantation of the implant 800 into a patient, the patient is preferably positioned on his side (arrow 841 points up from an operating table) and placed in a flexed (tucked) position in order to distract the upper and lower vertebrae.

In a preferred procedure, a small incision is made on the midline of the spinous processes. The spinous processes are spread apart or distracted with a spreader. The incision is spread downwardly toward the table, and the distracting unit 802 is preferably inserted upwardly between the spinous processes 840 and 842 in a manner that maintains the distraction of spinous processes. The distracting unit 802 is urged upwardly until the distracting or bulbous end 808 and the slot 806 are visible on the other wide of the spinous process. Once this is visible, the incision is spread upwardly away from the table and the retaining unit or second wing 824 is inserted into the slot 806 and the screw 822 is used to secure the second wing in position. After this had occurred, the incisions can be closed.

An alternative surgical approach requires that small incisions be made on either side of the space located between the spinous processes. The spinous processes are spread apart or distracted using a spreader placed through the upper incision. From the lower incision, the distracting unit 802 is preferably inserted upwardly between the spinous processes 840 and 842 in a manner that urges the spinous processes apart. The distracting unit 802 is urged upwardly until the distracting or bulbous end 808 and the slot 806 are visible through the second small incision in the patient's back. Once this is visible, the retaining unit or second wing 824 is inserted into the slot 806 and the screw 822 is used to secure the second wing in position. After this has occurred, the incisions can be closed.

The advantage of either of the above present surgical procedures is that a surgeon is able to observe the entire operation, where he can look directly down onto the spinous processes as opposed to having to view the procedure from positions which are to the right and to the left of the spinous processes. Generally, the incision is as small as possible and the surgeon is working in a bloody and slippery environment. Thus, an implant that can be positioned directly in front of a surgeon is easier to insert and assemble than an implant which requires the surgeon to shift from side to side. Accordingly, a top-down approach, as an approach along a position to anterior line is preferred so that all aspects of the implantation procedure are fully visible to the surgeon at all times. This aides in the efficient location of (i) the distracting unit between the spinous processes, (ii) the retaining unit in the distracting unit, and (iii) finally the set screw in the distracting unit.

Figure 80A:
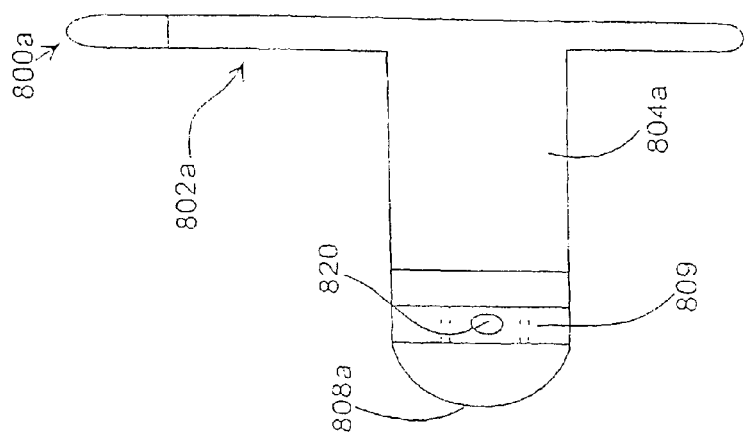

FIG. 80a shows an alternative embodiment of the distracting unit 802a. This distracting unit 802a is similar to distracting unit 802 in FIG. 80 with the exception that the bulbous end 808a is removable from the rest of the distracting body 804a as it is screwed into the threaded bore 809. The bulbous end 808a is removed once the distracting unit 802a is positioned in the patient in accordance with the description associated with FIG. 86. The bulbous end 808a can extend past the threaded bore 820 by about 1 cm in a preferred embodiment.

Embodiment of FIGS. 88, 89, 90 and 91

Another embodiment of the invention is shown in FIGS. 88, 89, 90 and 91. In this embodiment, the implant is identified by the number 900. Other elements of implant 900 which are similar to implant 800 are similarly numbered but in the 900 series. For example, the distracting unit is identified by the number 902 and this is in parallel with the distracting unit 802 of the implant 800. The distracting body is identified by the number 904 in parallel with the distracting body 804 of the implant 800. Focusing on FIG. 90, the distracting unit 902 is depicted in a perspective view. The distracting unit includes slot 906 which is wider at the top than at the bottom. The reason for this is that the wider upper portion of the slot 906, which is wider than the second wing 924 (FIG. 89), is used to, allow the surgeon to easily place the second wing 924 into the slot 906 and allow the wedge-shaped slot 906 to guide the second wing 924 to its final resting position. As can be see in FIG. 91, in the final resting position, the largest portion of the slot 906 is not completely filled by the second wing 924.

The end 908 of implant 900 is different in that it is more pointed, having sides 909 and 911 which are provided at about 45° angles (other angles, such as by way of example only, from about 30° to about 60° are within the spirit of the invention), with a small flat tip 913 so that the body 904 can be more easily urged between the spinous processes.

The distracting unit 902 further includes a tongue-shaped recess 919 which extends from the slot 906. Located in the tongue-shaped recess is a threaded bore 920.

As can be seen in FIG. 89, a second wing 924 includes a tongue 948 which extends substantially perpendicular thereto and between the upper and lower portions 926, 928. The tab 948 includes a bore 950. With the second wing 924 positioned in the slot 906 of the distracting unit 902 and tab 948 positioned in recess 919, a threaded set screw 922 can be positioned through the bore 950 and engage the threaded bore 920 in order to secure the second wing or retaining unit 924 to the distracting unit 902. The embodiment 900 is implanted in the same manner as embodiment 800 previously described. In addition, as the bore 922 is substantially perpendicular to the distracting body 904 (and not provided at an acute angle thereto), the surgeon can even more easily secure the screw in place from a position directly behind the spinous processes.

Embodiment of FIGS. 92, 92a, 92b, 93, 93a, 93b, 93c, 93d, 94, 94a, 94b, 95, 95a, and 96

Figure 92:
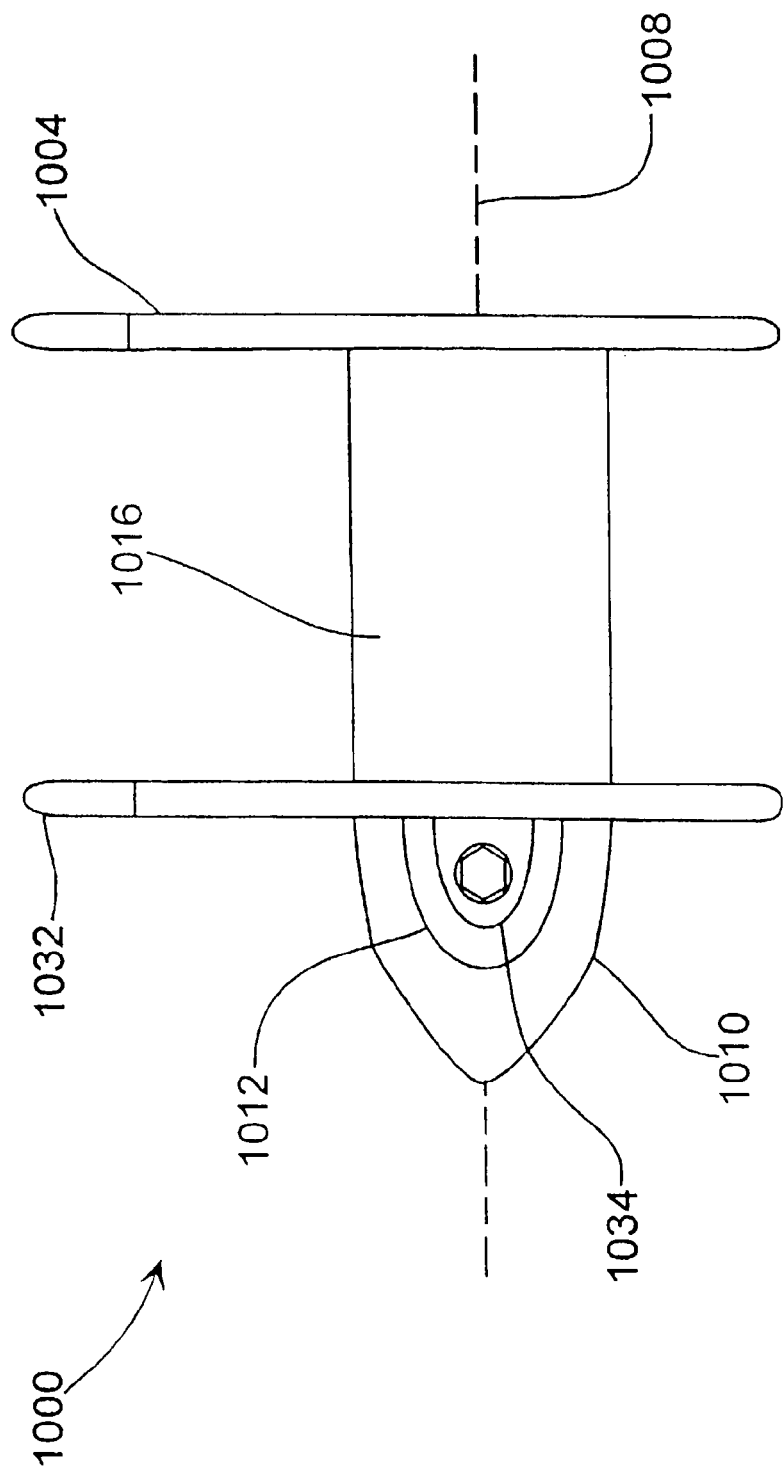

Still a further embodiment of the invention is depicted in FIGS. 92, and 92a. In this embodiment, the implant 1000 as can be seen in FIG. 92a includes a central elongated body 1002 which has positioned at one end thereof a first wing 1004. Wing 1004 is similar to the first wing previously described with respect to the embodiment of FIG. 88. Bolt 1006 secures wing 1004 to body 1002 in this embodiment. Bolt 1006 is received in a bore of the body 1002 which is along the longitudinal axis 1008 of body. It is to be understood that in this embodiment, the first unit is defined by the central body 1002, the first wing 1004, and the guide 1010.

Figure 93C:
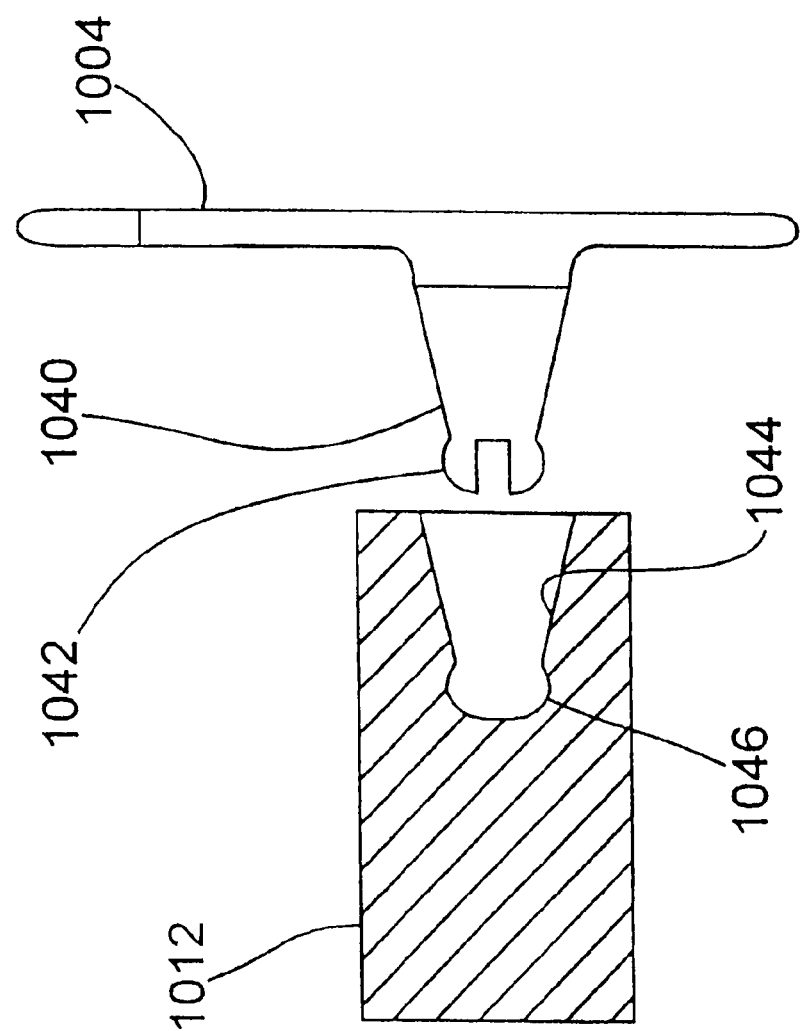

Alternatively, the first wing can be secured to the central body with a press fit and detent arrangement as seen in FIG. 93c. In this arrangement, the first wing has a protrusion 1040 extending preferably about perpendicularly from the first wing, with a flexible catch 1042. The protrusion and flexible catch are press fit into a bore 1044 of the central body with the catch received in a detent 1046.

Figure 93D:
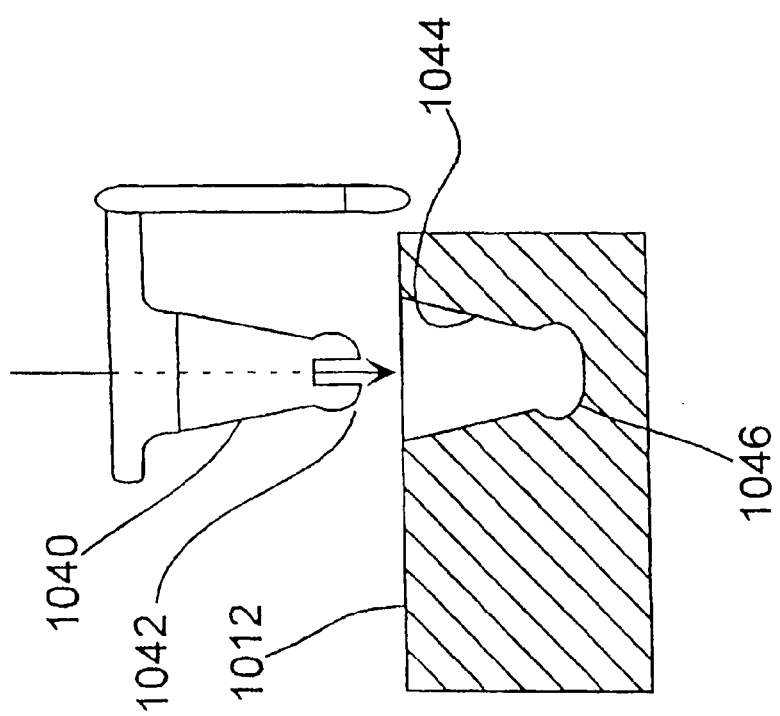

In yet another alternative embodiment, the first wing can be designed as shown in FIG. 93d with the protrusion directed substantially parallel to the first wing from a member that joins the first wing to the protrusion. Thus in this embodiment, the first wing is inserted into the body along the same direction as the second wing is inserted.

Positioned at the other end of the central body 1002 is a guide 1010. In this particular embodiment, guide 1010 is essentially triangularly-shaped so as to be a pointed and arrow-shaped guide. Alternatively, guide 1010 could be in the shape of a cone with lateral truncated sides along the longitudinal axis 1008. Guide 1010 includes a recess 1012 having a threaded bore 1014. Recess 1012 is for receiving a second wing 1032 as will be described hereinbelow.

Additionally, it is also to be understood that the guide 1010 can be bulbous, cone-shaped, pointed, arrow-shaped, and the like, in order to assist in the insertion of the implant 1000 between adjacent spinous processes. It is advantageous that the insertion technique disturb as little of the bone and surrounding tissue or ligaments as possible in order to (1) reduce trauma to the site and facilitate early healing, and (2) not destabilize the normal anatomy. It is to be noted that with the present embodiment, there is no requirement to remove any of the bone of the spinous processes and depending on the anatomy of the patient, there may be no requirement to remove or sever ligaments and tissues immediately associated with the spinous processes.

The implant 1000 further includes a sleeve 1016 which fits around and is at least partially spaced from the central body 1002. As will be explained in greater detail below, while the implant may be comprised of a bio-compatible material such as titanium, the sleeve is comprised preferably of a superelastic material which is by way of example only, a nickel titanium material (NiTi), which has properties which allow it to withstand repeated deflection without fatigue, while returning to its original shape. The sleeve could be made of other materials, such as for example titanium, but these materials do not have the advantages of a super-elastic material.

FIG. 93a is a cross-section through the implant 1000 depicting the central body 1002 and the sleeve 1016. As can be seen from the cross-section of FIG. 93a in a preferred embodiment, both the central body 1002 and the sleeve 1016 are substantially cylindrical and oval or ecliptically-shaped. An oval or elliptical shape allows more of the spinous process to be supported by the sleeve, thereby distributing the load between the bone and the sleeve more evenly. This reduces the possibility of fracture to the bone or bone resorption. Additionally, an oval or elliptical shape enhances the flexibility of the sleeve as the major axis of the sleeve, as described below, is parallel to the longitudinal direction of the spinous process. However, other shapes such as round cross-sections can come within the spirit and scope of the invention.

In this particular embodiment, the central body 1002 includes elongated grooves 1018, along axis 1008, which receives elongated spokes 1020 extending from the internal surface of the cylinder 1016.

In a preferred embodiment, both the cross-section of the central body and the sleeve have a major dimension along axis 1022 and a minor dimensional along axis 1024 (FIG. 93a). The spokes 1020 are along the major dimension so that along the minor dimension, the sleeve 1016 can have its maximum inflection relative to the central body 1002. It is to be understood that the central body along the minor dimension 1024 can have multiple sizes and can, for example, be reduced in thickness in order to increase the ability of the sleeve 1016 to be deflected in the direction of the central body 1002.

Alternatively as can be seen in FIG. 93b, the central body 1002 can include the spokes 1020 and the sleeve 1016 can be designed to include the grooves 1018 in order to appropriately space the sleeve 1016 from the central body 1002.

In other embodiments, the sleeve can have minor and major dimensions as follows:

| Minor Dimension | Major Dimension |
|---|---|
| 6 mm | 10 mm |
| 8 mm | 10.75 mm |
| 12 mm | 14 mm |
| 6 mm | 12.5 mm |
| 8 mm | 12.5 mm |
| 10 mm | 12.5 mm |

In one preferred embodiment, said sleeve has a cross-section with a major dimension and a minor dimension and said major dimension is greater than said minor dimension and less than about two times said minor dimension. In said embodiment, said guide has a cross-section which is adjacent to said sleeve with a guide major dimension about equal to said sleeve major dimension and a guide minor dimension about equal to said sleeve minor dimension. Further in said embodiment, said guide extends from said central body with a cross-section which reduces in size in a direction away from said central body.

In another preferred embodiment, said guide is cone-shaped with a base located adjacent to said sleeve. Further, said guide has a base cross-section about the same as the oval cross-section of said sleeve.

Thus, from the above, it is evident that preferably a major dimension of the sleeve correspond with a major dimension of the central body and a minor dimension of the sleeve corresponds with a minor dimension of the central body. Additionally, it is evident that the major dimension of the sleeve 1016 is substantially perpendicular to a major dimension of the first wing 1004 along longitudinal axis 1030 (FIG. 92*a*). This is so that as discussed above, when the implant 1000 is properly positioned between the spinous processes, a major portion of the sleeve comes in contact with both the upper and lower spinous processes in order to distribute the load of the spinous processes on the sleeve 1016 during spinal column extension.

As indicated above, the preferred material for the sleeve 1016 is a super-elastic material and more preferably one comprised of an alloy of nickel and titanium. Such materials are available under the trademark Nitinol. Other super-elastic materials can be used as long as they are bio-compatible and have the same general characteristics of super-elastic materials. In this particular embodiment, a preferred super-elastic material is made up of the following composition of nickel, titanium, carbon, and other materials as follows:

| Nickel | 55.80% by weight |
|---|---|
| Titanium | 44.07% by weight |
| Carbon | <0.5% by weight |
| Oxygen | <0.5% by weight |

Figure 118:
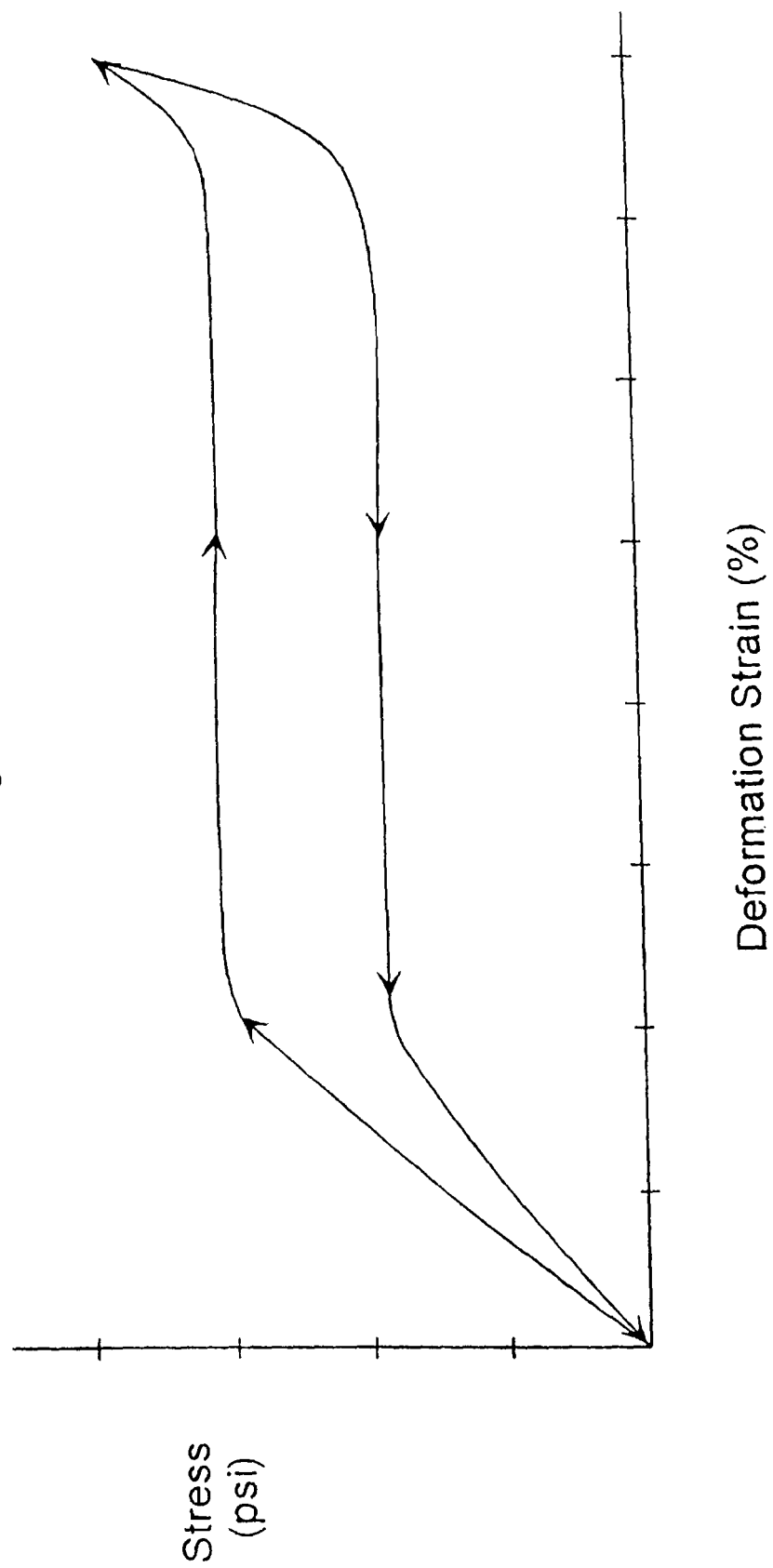
FIG. 118 depicts a graph showing characteristics of a preferred material usable with several of the embodiments of the present invention.

In particular, this composition of materials is able to absorb about 8% recoverable strain. Of course, other materials which can absorb greater and less than 8% can come within the spirit and scope of the invention. This material can be repeatably deflected toward the central body and returned to about its original shape without fatigue. Preferably and additionally, this material can withstand the threshold stress with only a small amount of initial deforming strain and above the threshold stress exhibit substantial and about instantaneous deformation strain which is many times the small amount of initial deforming strain. Such a characteristic is demonstrated in FIG. 118 where it is shown that above a certain threshold stress level, deformation strain is substantially instantaneous up to about 8%. FIG. 118 shows a loading and unloading curve between stress and deformation strain for a typical type of super-elastic material as described above.

Preferably, the above super-elastic material is selected to allow deformation of up to about, by way of example only, 8%, at about 20 lbs. to 50 lbs. force applied between a spinous processes. This would cause a sleeve to deflect toward the central body absorbing a substantial amount of the force of the spinous processes in extension. Ideally, the sleeves are designed to absorb 20 lbs. to 100 lbs. before exhibiting the super-elastic effect (threshold stress level) described above. Further, it is possible, depending on the application of the sleeve and the anatomy of the spinal column and the pairs of spinous processes for a particular individual, that the sleeve can be designed for a preferable range of 20 lbs. to 500 lbs. of force before the threshold stress level is reached. Experimental results indicate that with spinous processes of an older individual, that at about 400 pounds force, the spinous process may fracture. Further, such experimental results also indicate that with at least 100 pounds force, the spinous process may experience some compression. Accordingly, ideally the super-elastic material is designed to deform or flex at less than 100 pounds force.

In a preferred embodiment, the wall thickness of the sleeve is about 1 mm or $^{40}/_{1000}$ of an inch (0.040 in.). Preferably the sleeve is designed to experience a combined 1 mm deflection. The combined 1 mm deflection means that there is ½ mm of deflection at the top of the minor dimension and a ½ mm deflection at the bottom of the minor dimension. Both deflections are toward the central body.

In a particular embodiment where the sleeve is more circular in cross-section, with an outer dimension of 0.622 in. and a wall thickness of 0.034 in., a 20 lb. load causes a 0.005 in. deflection and a 60 lb. load causes a 0.020 in. deflection (approximately ½ mm). A 100 lb. load would cause a deflection of about 0.04 in. or approximately 1 mm.

Thus in summary, the above preferred super-elastic material means that the sleeve can be repeatedly deflected and returned to about its original shape without showing fatigue. The sleeve can withstand a threshold stress with a small amount of deforming strain and at about said threshold stress exhibit about substantially instantaneous deformation strain which is many times the small amount of the forming strain. In other words, such super-elastic qualities mean that the material experiences a plateau stress where the material supports a constant force (stress) over very large strain range as exhibited in FIG. 118.

It is to be understood that for this particular embodiment, bar stock of the super-elastic material is machined into the appropriate form and then heat treated to a final temperature to set the shape of the material by increasing the temperature of the material to 932° Fahrenheit and holding that temperature for five (5) minutes and then quickly quenching the sleeve in water. It is also to be understood that preferably the present nickel titanium super-elastic alloy is selected to have a transition temperature $A_f$ of about 59° Fahrenheit (15° C.). Generally for such devices the transition temperature can be between 15° C. to 65° C. (59° F. to 149° F.), and more preferably 10° C. to 40° C. (50° F. to 104° F.). Preferably, the material is maintained in the body above the transition temperature in order to exhibit optimal elasticity qualities.

Alternatively, and preferably, the sleeve can be fabricated by wire Electrical Discharge Machining (EDM) rather than machined. Additionally, the sleeve can be finished using a shot blast technique in order to increase the surface strength and elasticity of the sleeve.

Figure 94B:
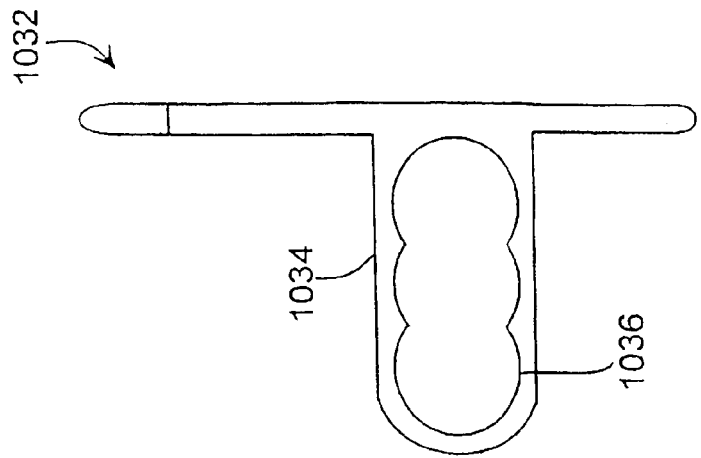
Figure 94A:
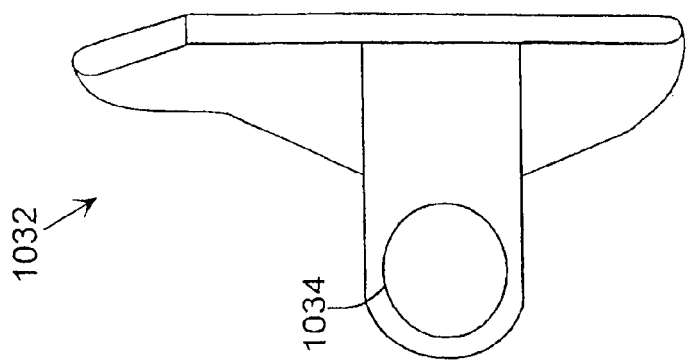
Figure 94:
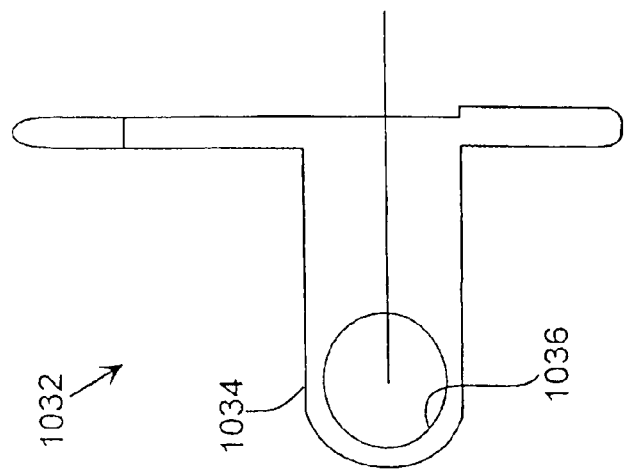
Figure 96:
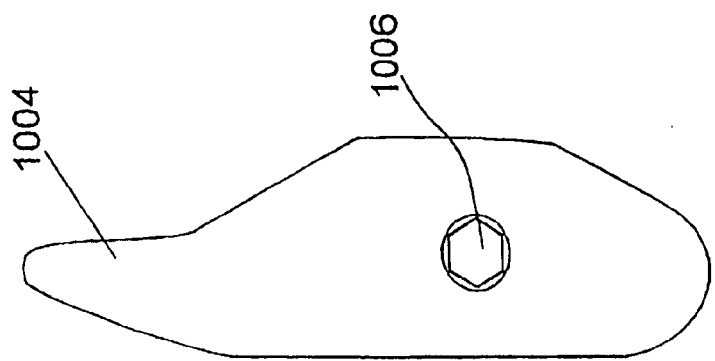
Figure 95A:
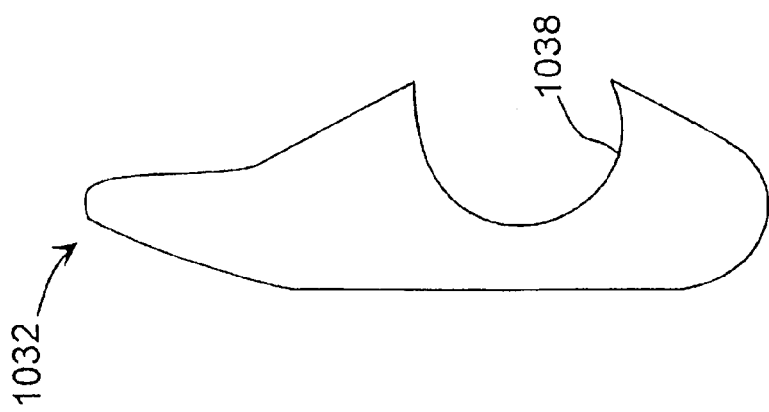
Figure 95:
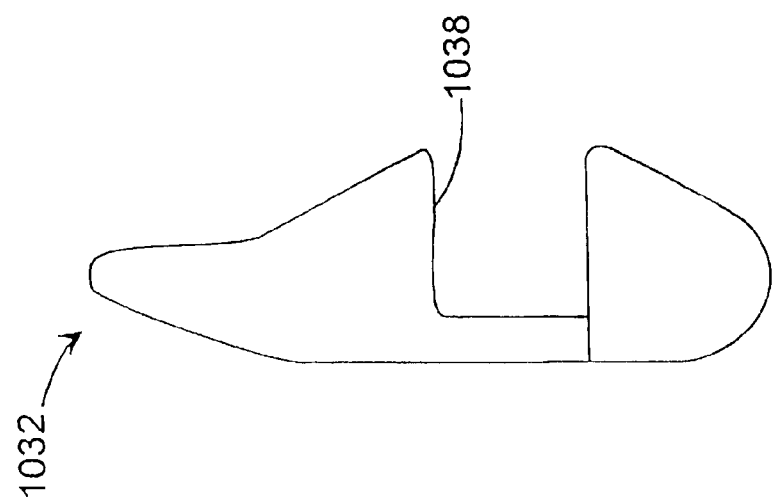

Top and side views of the second wing 1032 are shown in FIGS. 94 and 95. Second wing 1032 as in several past embodiments includes a tab 1034 with a bore 1036 which aligns with the bore 1014 of the guide 1010. In this particular embodiment, the second wing 1032 includes a cut-out 1038 which is sized to fit over the guide 1010, with the tab 1034 resting in the recess 1012 of the guide 1010.

An alternative configuration of the second wing 1032 is depicted in FIG. 94*a*. In this configuration, the second wing 1032 is held at acute angle with respect to the tab 1034. This is different from the situation in the embodiment of FIGS. 94 and 95 where the second wing is substantially perpendicular to the tab. For the embodiment of the second wing in FIG. 94*a*, such embodiment will be utilized as appropriate depending on the shape of the spinous processes.

With respect to the alternative second wing 1032 depicted in FIGS. 94*b* and 95*a*, elongated tab 1034 has a plurality of closely positioned bores 1036. The bores, so positioned, appear to form a scallop shape. Each individual scallop portion of the bore 1036 can selectively hold the bolt in order to effectively position the second wing 1032 in three different positions relative to the first wing 1004. The cut-out 1038 (FIG. 95*a* of this alternative embodiment) is enlarged over that of FIG. 95 as in a position closest to the first wing 1004, the second wing 1032 is immediately adjacent and must conform to the shape of the sleeve 1016.

Figure 97:
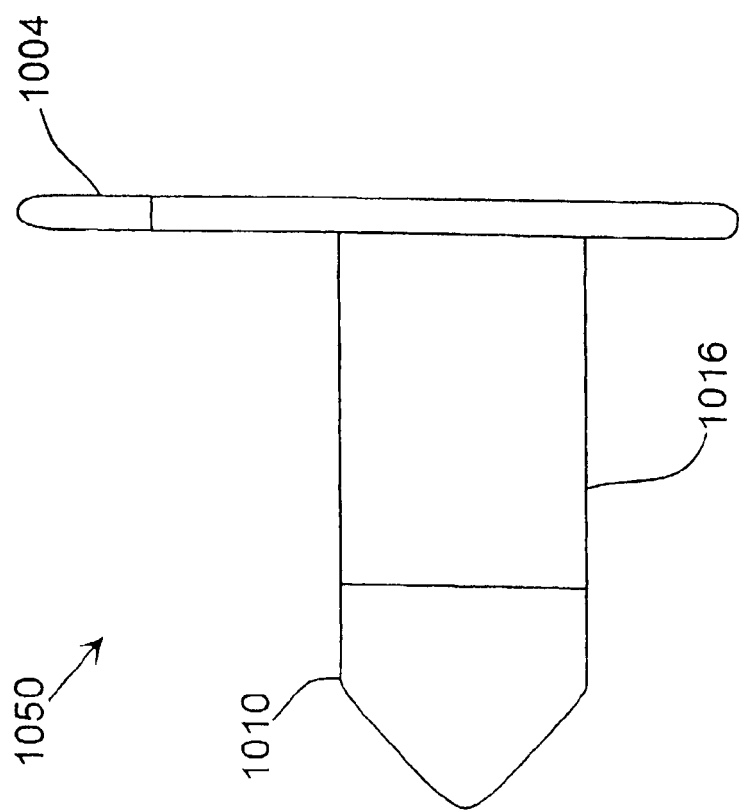
FIG. 97 depicts still another embodiment of the present invention.

Embodiment of FIG. 97

Implant 1050 of FIG. 97 is similar to the implant 1000 in FIG. 92 with the major difference being that a second wing is not required. The implant 1050 includes a central body as does implant 1000. The central body is surrounded by a sleeve 1016 which extends between a first wing 1004 and a guide 1010. The guide 1010 in this embodiment is substantially cone-shaped without any flats and with no bore as there is no need to receive a second wing. The sleeve and the central body as well as the first wing and guide act in a manner similar to those parts of the implant 1000 in FIG. 92. It is to be understood a cross-section of this implant 1050 through sleeve 1016 can preferably be like FIG. 93*a*. This particular embodiment would be utilized in a situation where it was deemed impractical or unnecessary to use a second wing. This embodiment has the significant advantages of the sleeve being comprised of super-elastic alloy materials as well as the guide being utilized to guide the implant between spinous processes while minimizing damage to the ligament and tissue structures found around the spinous processes.

Figure 98:
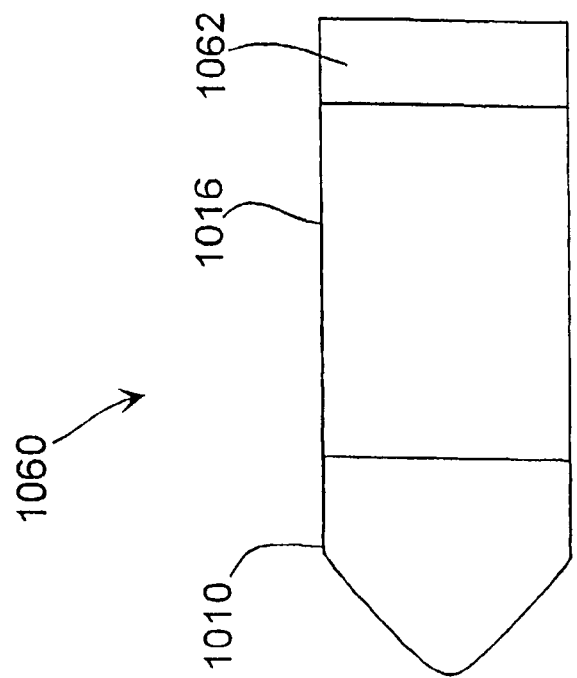
FIG. 98 depicts yet a further embodiment of the present invention.

Embodiment of FIG. 98

Implant 1060 is depicted in FIG. 98. This implant is similar to the implants 1000 of FIG. 92 and the implant 1050 of FIG. 97, except that this implant does not have either first or second wings. Implant 1060 includes a sleeve 1016 which surrounds a central body just as central body 1002 of implant 1000 in FIG. 93. It is to be understood that a cross-section of this implant 1060 through sleeve 1016 can preferably be like FIG. 93*a*. Implant 1060 includes a guide 1010 which in this preferred embodiment is cone-shaped. Guide 1010 is located at one end of the central body. At the other end is a stop 1062. Stop 1062 is used to contain the other end of the sleeve 1016 relative to the central body. This embodiment is held together with a bolt such as bolt 1006 of FIG. 93 that is used for the immediate above two implants. For the implant 1060 of FIG. 98, such a device would be appropriate where the anatomy between the spinous processes was such that it would be undesirable to use either a first or second wing. However, this embodiment affords all the advantageous described hereinabove (FIGS. 92 and 97) with respect to the guide and also with respect to the dynamics of the sleeve.

Figure 99:
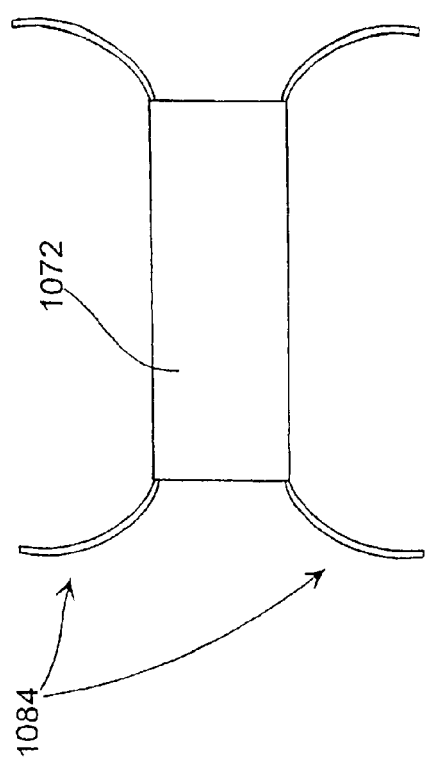
FIGS. 99 and 100 depict still another embodiment of the present invention including an insertion tool.
Figure 100:
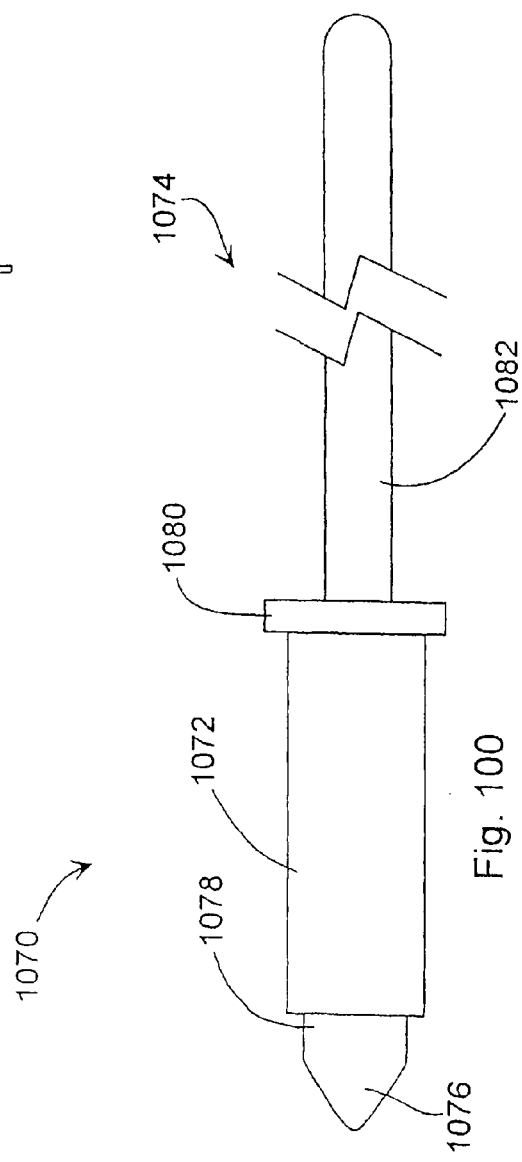

Embodiment of FIGS. 99 and 100

FIGS. 99 and 100 depict an implant system 1070. Implant system 1070 includes a sleeve 1072 which is similar to and has the advantageous of sleeve 1016 of the embodiment in FIG. 92. Sleeve 1072 does not, however, have any spokes. Additionally, implant system 1070 includes an insertion tool 1074. Insertion tool 1074 includes a guide 1076 which in a preferred embodiment is substantially cone-shaped. Guide 1076 guides the insertion of the sleeve 1072 and the insertion tool 1074 between adjacent spinous processes. The insertion tool 1074 further includes a central body 1078, a stop 1080, and a handle 1082. The guide 1076 at its base has dimensions which are slightly less than the internal dimensions of the sleeve 1074 so that the sleeve can fit over the guide 1076 and rest against the stop 1080. The tool 1074 with the guide 1076 is used to separate tissues and ligaments and to urge the sleeve 1072 in the space between the spinous processes. Once positioned, the guide insertion tool 1074 can be removed leaving the sleeve 1072 in place. If desired, after the sleeve is positioned, position maintaining mechanisms such as springy wires 1084 made out of appropriate material such as the super-elastic alloys and other materials including titanium, can be inserted using a cannula through the center of the sleeve 1072. Once inserted, the ends of the retaining wires 1084 (FIG. 99) extend out of both ends of the sleeve 1072, and due to this springy nature, bent at an angle with respect to the longitudinal axis of the sleeve 1072. These wires help maintain the position of the sleeve relative to the spinous processes.

Embodiment of FIGS. 101, 102, 102*a*, 103, 104, 105, 106, and 107

Figure 101:
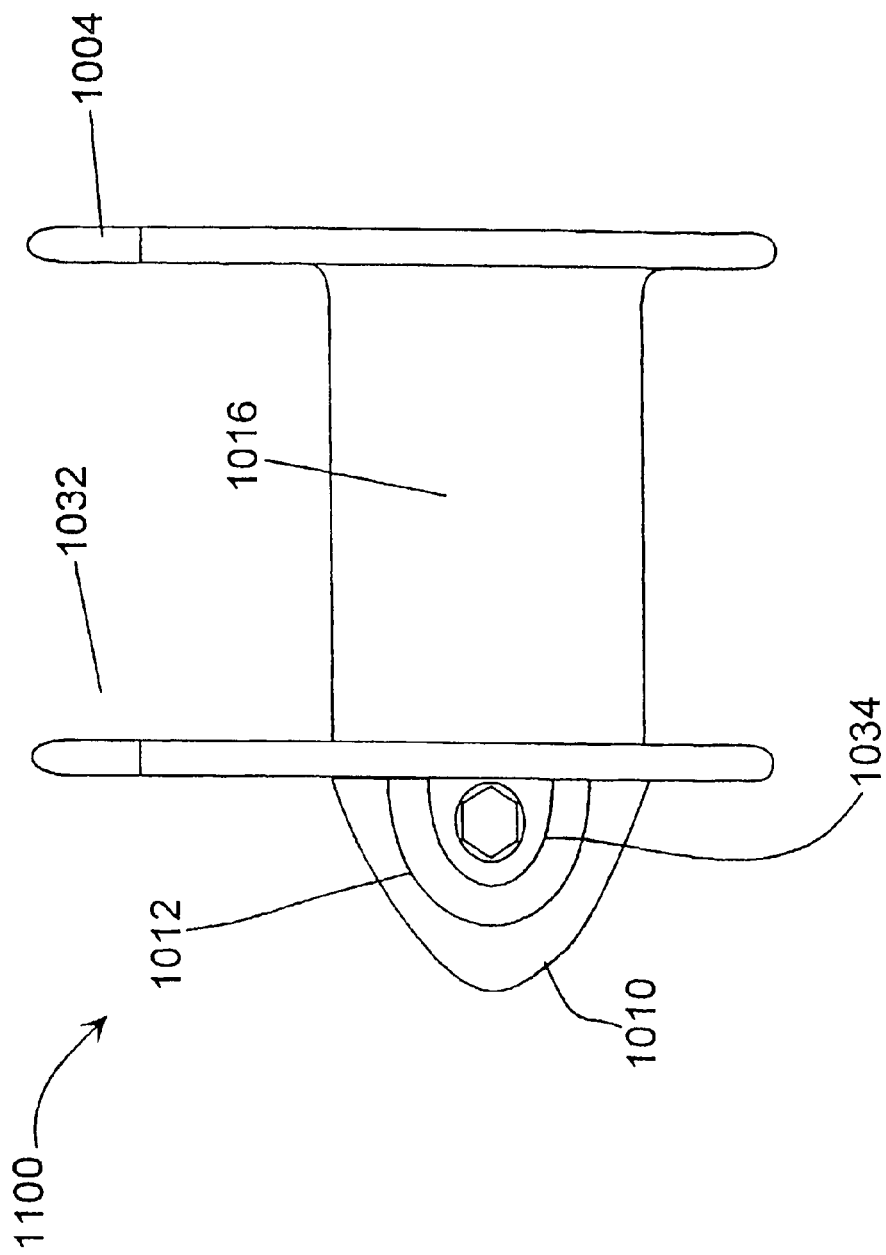
FIGS. 101, 102, 102a, 103, 104, 105, 106, and 107 depict still a further embodiment of the present invention.

Another embodiment of the invention can be seen in FIG. 101 which includes implant 1100. Implant 1100 has many similar features that are exhibited with respect to implant 1000 in FIG. 92. Accordingly, elements with similar features and functions would be similarly numbered. Additionally, features that are different from implant 1100 can be, if desired, imported into and become a part of the implant 1000 of FIG. 92.

As with implant 1000, implant 1100 includes a central body 1002 (FIG. 102) with a first wing 1004 and a bolt 1006 which holds the first wing and the central body together. In this particular embodiment, the central body is made in two portions. The first portion 1102 is in the shape of a truncated cone with an oval or elliptical base and a second portion 1104 includes a cylindrical central portion with a distal end in the shape of a truncated cone 1103 with an oval or elliptical base. In addition, in this particular embodiment, formed with the central body is the guide 1010 which has an oval or elliptical base. Bolt 1006 is used to secure the first wing through the second portion 1104 with the first portion 1102 held in-between. In this particular embodiment, the guide 1010 in addition to including recess 1012 and bore 1014 includes a groove 1106 which receives a portion of the second wing 1032.

Figure 102A:
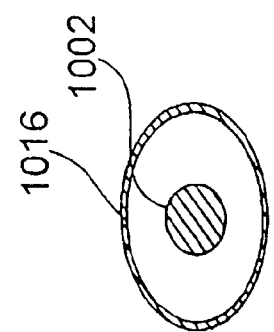
Figure 102:
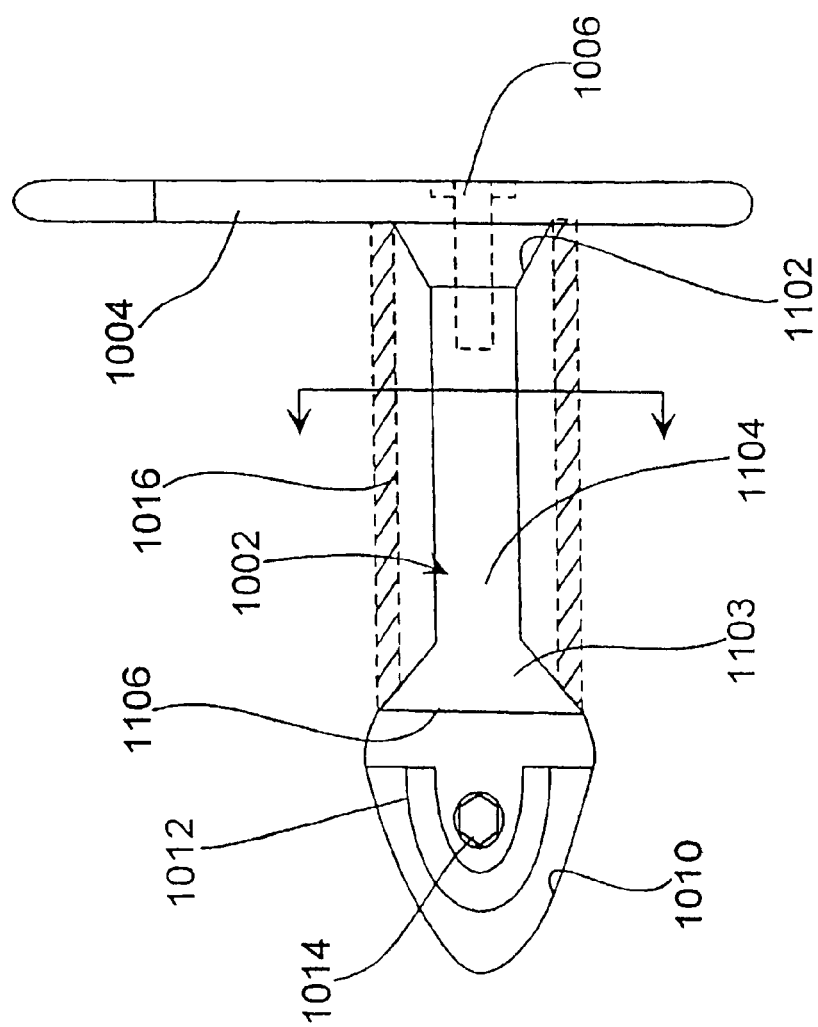

In this particular embodiment, the sleeve 1016 is preferably oval or elliptical in shape as can be seen in FIG. 102*a*.

The central body can be oval, elliptical or circular in cross-section, although other shapes are within the spirit and scope of the invention. The sleeve 1016 held in position due to the fact that the truncated conical portion 1102 and the corresponding truncated conical portion 1103 each have a base that is elliptical or oval in shape. Thus, the sleeve is held in position so that preferably the major dimension of the elliptical sleeve is substantially perpendicular to the major dimension of the first wing. It is to be understood that if the first wing is meant to be put beside the vertebrae so that the first wing is set at an angle other than perpendicular with respect to the vertebrae and that the sleeve may be held in a position so that the major dimension of the sleeve is at an angle other than perpendicular to the major dimension of the first wing and be within the spirit and scope of the invention. This could be accomplished by tightening bolt 1006 with the first wing 1004 and sleeve 1016 so positioned. In such a configuration, the major dimension of the sleeve would be preferably positioned so that it is essentially parallel to the length of the adjacent spinous processes. So configured, the elliptical or oval shape sleeve would bear and distribute the load more evenly over more of its surface.

It is to be understood that the sleeve in this embodiment has all the characteristics and advantages described hereinabove with respect to the above-referenced super-elastic sleeves.

Figure 105:
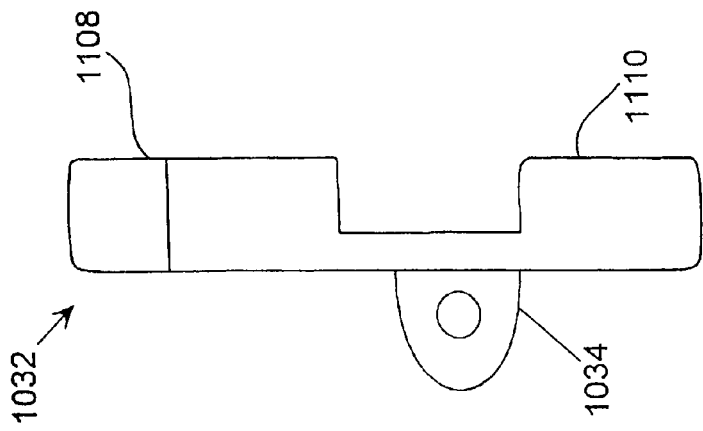
Figure 104:
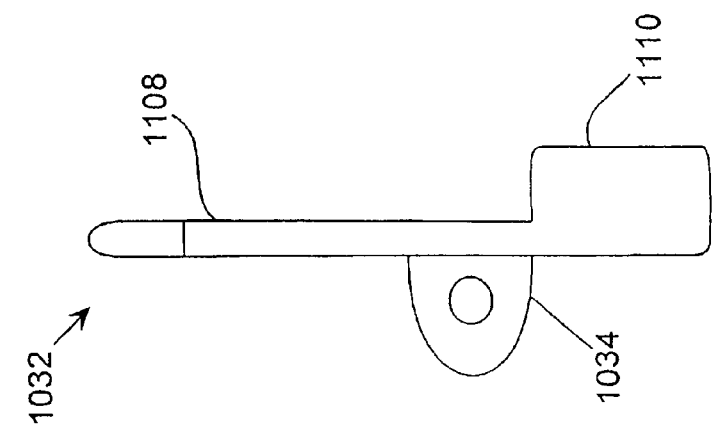
Figure 103:
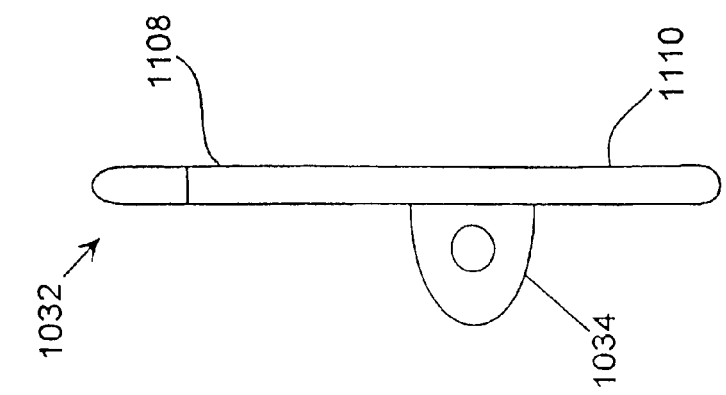

The second wing as discussed above, can come in a variety of shapes in order to provide for variations in the anatomical form of the spinous processes. Such shapes are depicted in FIGS. 103, 104, 105, 106, and 107. In each configuration, the second wing 1032 has a upper portion 1108 and a lower portion 1110. In FIG. 104, the lower portion is thicker than the upper portion in order to accommodate the spinous process, where the lower spinous process is thinner than the upper spinous process. In FIG. 105, both the upper and lower portions are enlarged over the upper and lower portions of FIG. 103 to accommodate both the upper and lower spinous processes being smaller. That is to say that the space between the upper and lower portions of the first and second wings are reduced due to the enlarged upper and lower portions of the second wing.

Figure 107:
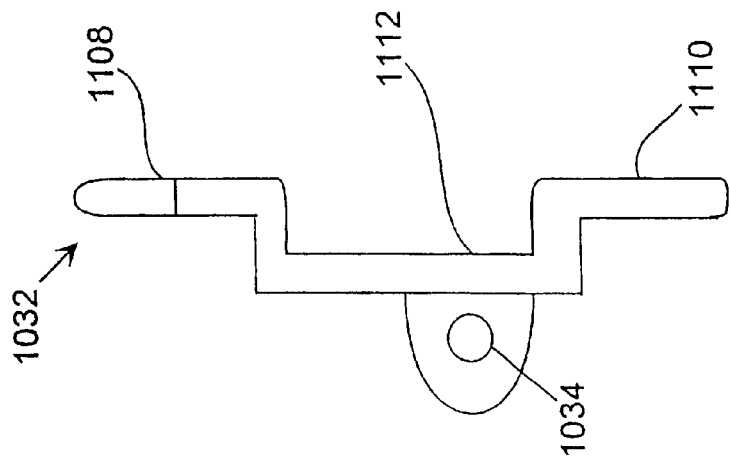
Figure 106:
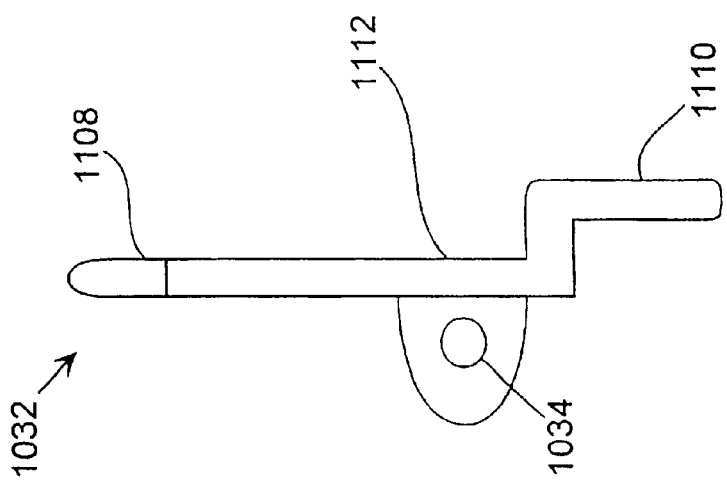

Alternative embodiments of second wings, as shown in FIGS. 104 and 105, are depicted in FIGS. 106 and 107. In these FIGS. 106 and 107, the second wing 1032 accommodates the same anatomical shape and size of the spinous processes as does the second wing in FIGS. 104 and 105 respectively. However, in the embodiments of the second wing 1032 of FIGS. 106 and 107, substantial masses have been removed from the wings. The upper and lower portions 1108 and 1110 are essentially formed or bent in order to extend from the central portion 1112 of the second wing 1032.

It is to be understood that in this embodiment, if desired, the second wing may not have to be used, depending on the anatomy of the spinal column of the body, and this embodiment still has the significant advantages attributable to the guide 1010 and the functionality of the sleeve 1016.

Figure 108:
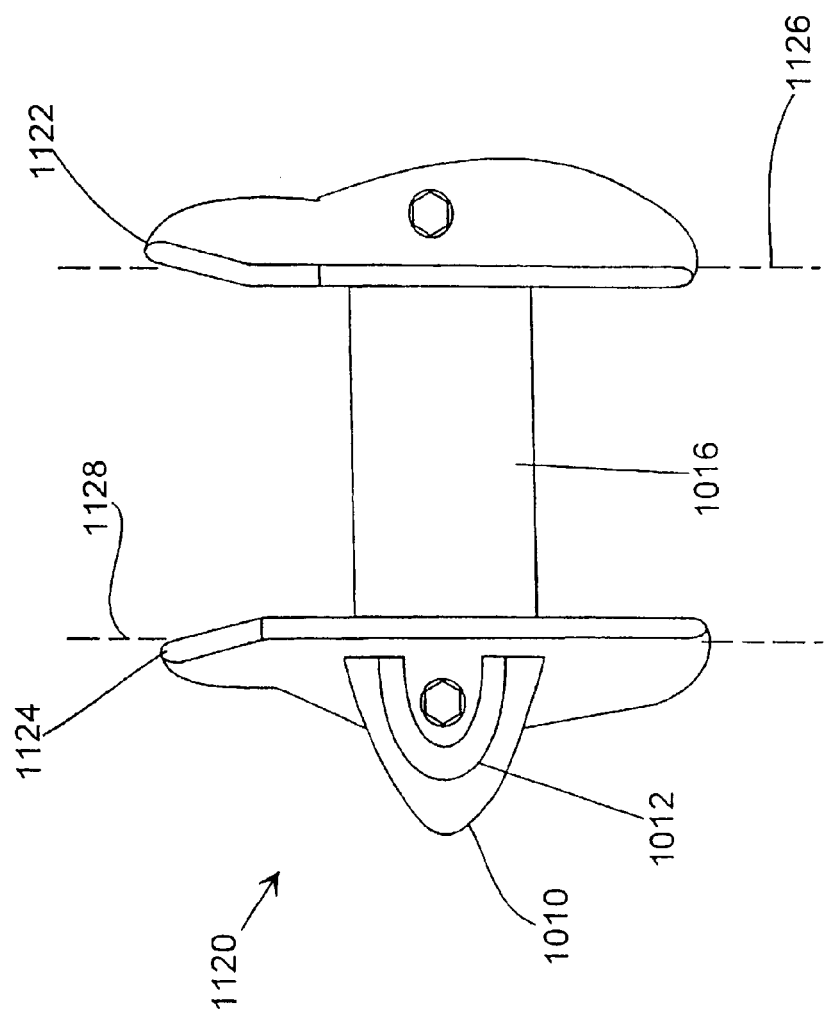
FIGS. 108, 109, and 110 depict still another embodiment of the present invention.
Figure 109:
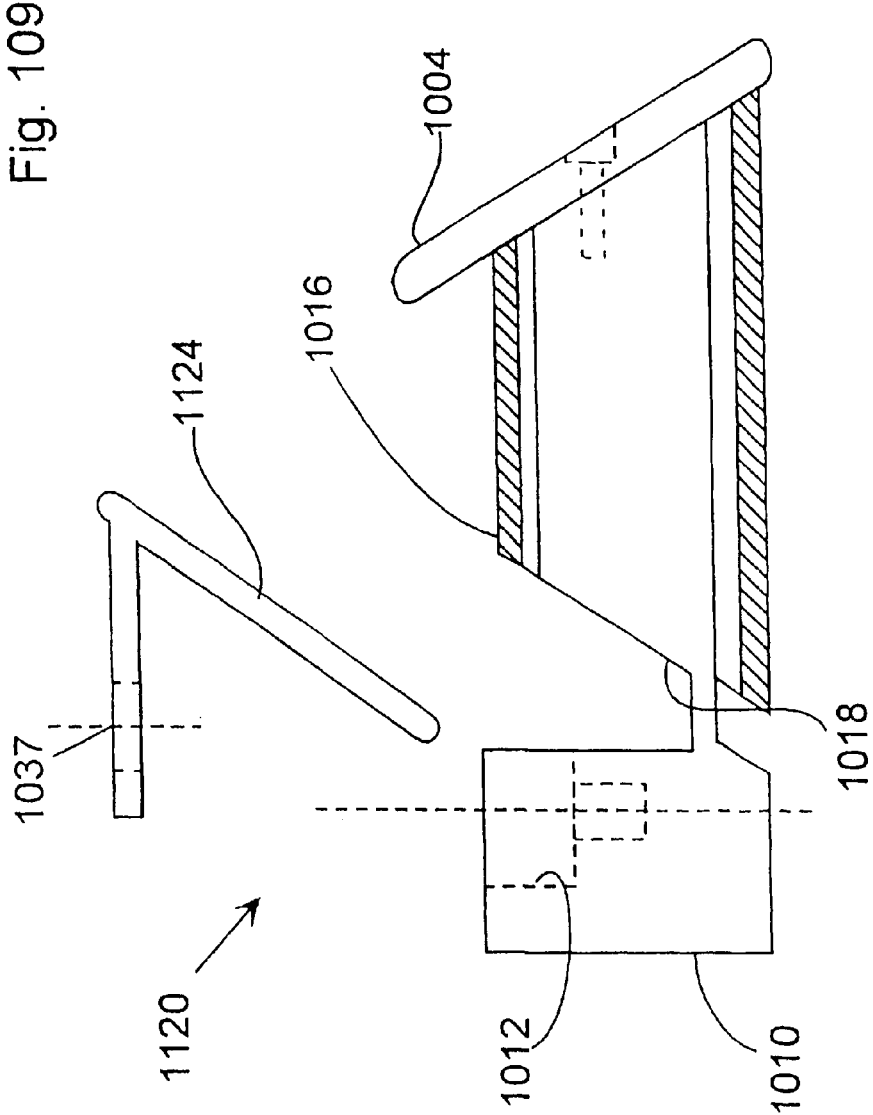
Figure 110:
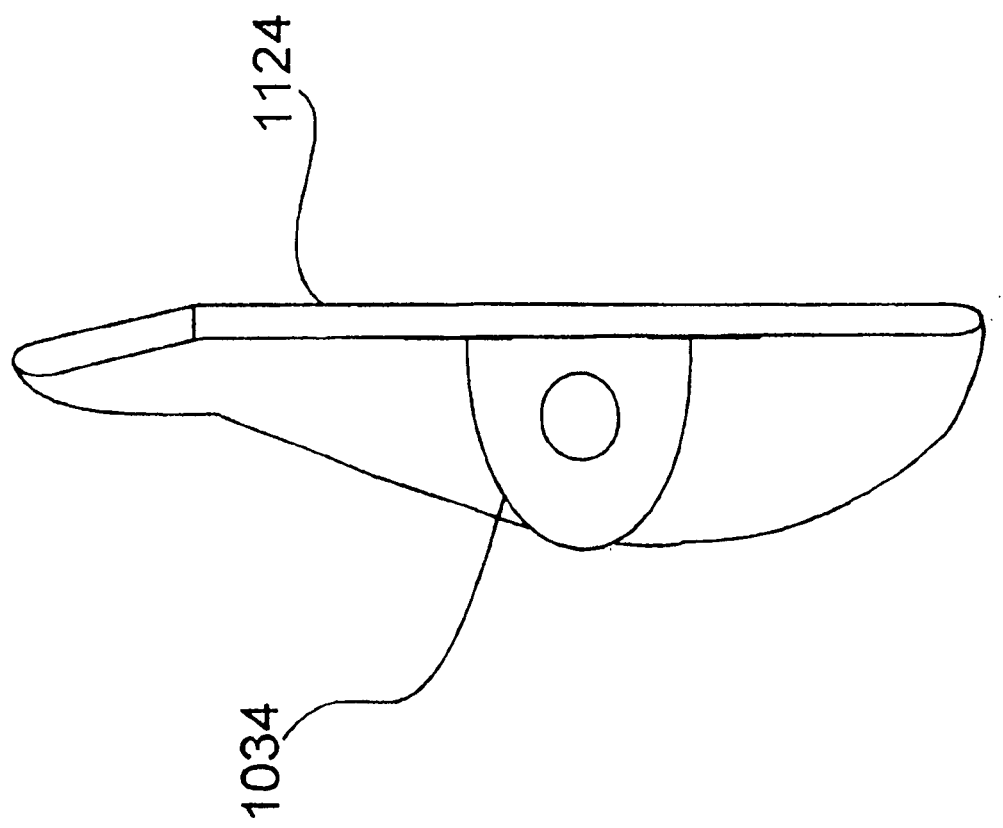

Embodiment of FIGS. 108, 109, and 110

The implant 1120 as shown in FIGS. 108 and 109, is similar to implant 1100 which is in turn similar to implant 1000. Such similar details have already been described above and reference here is made to the unique orientation of the first and second wings 1122 and 1124. These wings have longitudinal axis 1126 and 1128 respectfully. As can be seen in these figures, the first and second wings 1122, 1124 have been rotated so that they both slope inwardly and if they were to continue out of the page of the drawing of FIG. 108, they would meet to form an A-frame structure as is evident from the end view of FIG. 109. In this particular embodiment, as can be seen in FIGS. 109 and 110, the tab 1034 is provided an acute angle to the remainder of the second wing 1124. Further, the groove 1018 formed in the implant is sloped in order to accept the second wing 1124. Accordingly, this present implant 1120 is particularly suited for an application where the spinous process is wider adjacent to the vertebral body and then narrows in size at least some distance distally from the vertebral body. It is to be understood that a cross-section of this implant 1120 through sleeve 1016 can preferably be like FIG. 93a.

Embodiment of FIGS. 111, 112, 113, 114, 115, 116, and 117

An additional embodiment of the implant 1150 is shown in FIG. 111. Implant 1150 has features similar to those described with respect to FIG. 94b.

Implant 1150 includes a central body 1152 with a first wing 1154, where central body 1152 includes elongated groove 1156 which extends to the guide 1158. A screw 1160 is received in a threaded bore located in the elongated groove 1156.

The second wing 1162 includes a central body 1164 which is substantially perpendicular to the second wing 1162.

The central body 1164 includes a plurality of bores 1166 provided therein. These bores are formed adjacent to each other in order to define a plurality of scallops, each scallop capable of retaining bolt 1160 therein. As can be seen in FIG. 114, the second wing includes a cut-out 1168 such that with the central body 1164 of the second wing received in the groove 1156 of the central body associated with the first wing, the remainder of the second wing is received over the central body 1152 of the implant 1150. With this implant 1150, the distance between the first and second wings can be adjusted by selectively placing the bolt 1160 through one of the five specified bores defined by the scalloped plurality of bores 1166. Accordingly, FIG. 112 depicts the implant where the first and second wings are widest apart in order to accommodate spinous processes of greater thickness. FIG. 111 shows the middle position between the first and second wings in order to accommodate average size spinous processes.

It is to be understood that preferably during the surgical process, the central body 1152 is urged between spinous processes. After this has occurred, the second wing is guided by the other sides of the spinous processes from a path which causes the plane of the second wing to move substantially parallel to the plane of the first wing until the central body 1164 associated with the second wing 1162 is received in the groove of 1156 of the central body 1152 associated with the first wing 1154. After this has occurred, the bolt 1160 is positioned through aligned bores associated with the second wing 1162 and the central body 1152 in order to secure the second wing to the central body.

While embodiment 1150 does not depict a sleeve such as sleeve 1016, such a sleeve 1016 could be placed over body 1152 and be within the spirit of the invention.

INDUSTRIAL APPLICABILITY

From the above, it is evident that the present invention can be used to relieve pain caused by spinal stenosis in the form of, by way of example only, central canal stenosis or foraminal (lateral) stenosis. These implants have the ability to flatten the natural curvature of the spine and open the neural foramen and the spacing between adjacent vertebra to relieve problems associated with the above-mentioned lateral and central stenosis. Additionally, the invention can be used to relieve pain associated with facet arthropathy. The present invention is minimally invasive and can be used on an outpatient basis.

Additional aspects, objects and advantages of the invention can be obtained through a review of the appendant claims and figures.

It is to be understood that other embodiments can be fabricated and come within the spirit and scope of the claims.

What is claimed is:

1. A method, comprising:
    inserting a cannula from a lateral side of adjacent spinous processes such that at least a first portion of the cannula fits directly between adjacent spinous processes;
    inserting an implant through the cannula from the lateral side while the first portion of the cannula is disposed directly between the adjacent spinous processes such that at least a portion of the implant is disposed between the adjacent spinous processes; wherein the inserting includes pushing the implant through the cannula via an insertion tool while a distal end face of the insertion tool abuts a proximal end portion of the implant;
    removing the cannula after the inserting the implant such that at least a portion of the implant remains disposed between the adjacent spinous processes; and wherein the implant is configured to limit extension of a spinal column including the adjacent spinous processes and configured to allow flexion of the spinal column.

2. The method of claim 1, wherein the implant has a plurality of indentations configured to position the implant relative to the adjacent spinous processes.

3. The method of claim 1, wherein the cannula defines a longitudinally curved path between an incision in skin laterally spaced from the spine and a space between the adjacent spinous processes.

4. The method of claim 1, wherein the cannula is a first cannula from a plurality of cannulas, the method further comprising:
    inserting a second cannula from the plurality of cannulas from a lateral side of adjacent spinous processes such that at least a first portion of the cannula is disposed directly between adjacent spinous processes;
    wherein the inserting the first cannula comprises inserting the first cannula over the second cannula;
    the second cannula having a cross-sectional size smaller than a cross-sectional size of the first cannula.

5. The method of claim 1, wherein the inserting includes inserting the implant such that at least the portion of the implant is disposed within a space between the adjacent spinous processes, the space bounded by a first spinous process, a second spinous process adjacent the first spinous process, and a supraspinous ligament coupled to the adjacent spinous processes.

6. The method of claim 1, wherein the implant has a rib that substantially circumscribes an outer surface of the implant, the rib configured to indicate a position of the implant relative to the adjacent spinous processes.

7. The method of claim 1, wherein a shape of the implant substantially corresponds to a shape of the cannula.

8. A method of inserting a spinal implant, comprising:
    inserting a cannula from a lateral side of adjacent spinous processes such that a distal opening of the cannula is disposed adjacent to and facing an interspinous space directly between adjacent spinous processes; the opening being smaller than the interspinous space;
    inserting an implant through the cannula from the lateral side while the distal opening is disposed adjacent to and facing the interspinous space such that at least a portion of the implant is disposed between the adjacent spinous processes; wherein the inserting includes pushing the implant through the cannula via an insertion tool while a distal end face of the insertion tool abuts a proximal end portion of the implant;
    removing the cannula after the inserting the implant such that at least a portion of the implant remains disposed between the adjacent spinous processes; and wherein the implant is configured to limit extension of a spinal column including the adjacent spinous processes and configured to allow flexion of the spinal column.

9. The method of claim 8 wherein the implant has a plurality of indentations configured to position the implant relative to the adjacent spinous processes.

10. The method of claim 8 wherein the cannula defines a longitudinally curved path between an incision in skin laterally spaced from the spine and the interspinous space.

11. The method of claim 8 wherein the cannula is a first cannula from a plurality of cannulas, the method further comprising:
    inserting a second cannula from the plurality of cannulas from a lateral side of adjacent spinous processes such that a distal opening of the second cannula is disposed adjacent to and facing the interspinous space;
    wherein the inserting the first cannula comprises inserting the first cannula over the second cannula;
    the second cannula having a cross-sectional size smaller than a cross-sectional size of the first cannula.

12. The method of claim 8 wherein the implant has a rib that substantially circumscribes an outer surface of the implant, the rib configured to indicate a position of the implant relative to the adjacent spinous processes.

13. The method of claim 8 wherein a shape of the implant substantially corresponds to a shape of the cannula.

* * * * *